(12) United States Patent
Radtkey et al.

(10) Patent No.: US 8,772,467 B2
(45) Date of Patent: Jul. 8, 2014

(54) METHODS AND APPARATUS FOR SCREENING AND DETECTING MULTIPLE GENETIC MUTATIONS

(75) Inventors: Ray R. Radtkey, San Diego, CA (US); Lance C. Held, San Marcos, CA (US); Robert B. Wallace, Escondido, CA (US); Karen Menge, San Diego, CA (US); David Canter, San Diego, CA (US)

(73) Assignee: Gamida for Life B.V., Rotterdam (NL)

( * ) Notice: Subject to any disclaimer, the term of this patent is extended or adjusted under 35 U.S.C. 154(b) by 147 days.

(21) Appl. No.: 12/574,875

(22) Filed: Oct. 7, 2009

(65) Prior Publication Data

US 2010/0167960 A1 Jul. 1, 2010

Related U.S. Application Data

(62) Division of application No. 10/627,950, filed on Jul. 24, 2003, now Pat. No. 7,601,493.

(60) Provisional application No. 60/443,989, filed on Jan. 30, 2003, provisional application No. 60/398,992, filed on Jul. 26, 2002.

(51) Int. Cl.
| | |
|---|---|
| *C07H 21/04* | (2006.01) |
| *C07H 21/02* | (2006.01) |
| *C12Q 1/68* | (2006.01) |
| *C12P 19/34* | (2006.01) |
| *C12M 1/34* | (2006.01) |
| *C12M 3/00* | (2006.01) |
| *G01N 33/00* | (2006.01) |
| *G01N 33/556* | (2006.01) |

(52) U.S. Cl.
USPC ....... 536/24.3; 536/23.1; 536/24.33; 435/6.1; 435/6.11; 435/91.1; 435/287.2; 436/94; 436/501

(58) Field of Classification Search
USPC ............. 435/6, 91.1, 91.2, 183, 287.1, 287.2; 436/94, 501; 536/23.1, 24.3, 24.33, 536/25.3
See application file for complete search history.

(56) References Cited

U.S. PATENT DOCUMENTS

| | | |
|---|---|---|
| 3,950,738 A | 4/1976 | Hayashi et al. |
| 3,995,190 A | 11/1976 | Saigo |
| 4,283,773 A | 8/1981 | Daughton et al. |
| 4,563,419 A | 1/1986 | Ranki et al. |
| 4,580,895 A | 4/1986 | Patel |
| 4,584,075 A | 4/1986 | Goldstein et al. |
| 4,594,135 A | 6/1986 | Goldstein |
| 4,731,325 A | 3/1988 | Palva et al. |
| 4,751,177 A | 6/1988 | Stabinsky |
| 4,787,963 A | 11/1988 | MacConnell |
| 4,807,161 A | 2/1989 | Comfort et al. |
| 4,816,418 A | 3/1989 | Mack et al. |
| 4,822,566 A | 4/1989 | Newman |
| 4,828,979 A | 5/1989 | Klevan et al. |
| 4,883,750 A | 11/1989 | Whiteley et al. |
| 4,908,112 A | 3/1990 | Pace |
| 4,988,617 A | 1/1991 | Landegren et al. |
| 5,030,557 A | 7/1991 | Hogan et al. |
| 5,063,081 A | 11/1991 | Cozzette et al. |
| 5,074,977 A | 12/1991 | Cheung et al. |
| 5,075,077 A | 12/1991 | Durley, III et al. |
| 5,096,669 A | 3/1992 | Lauks et al. |
| 5,096,807 A | 3/1992 | Leaback |
| 5,114,674 A | 5/1992 | Stanbro et al. |
| 5,125,748 A | 6/1992 | Bjornson |
| 5,126,022 A | 6/1992 | Soane et al. |
| 5,143,854 A | 9/1992 | Pirrung et al. |
| 5,164,319 A | 11/1992 | Hafeman et al. |
| 5,166,063 A | 11/1992 | Johnson |
| 5,200,051 A | 4/1993 | Cozzette et al. |
| 5,202,231 A | 4/1993 | Drmanac et al. |
| 5,219,726 A | 6/1993 | Evans |
| 5,227,265 A | 7/1993 | DeBoer et al. |
| 5,234,566 A | 8/1993 | Osman et al. |
| 5,242,797 A | 9/1993 | Hirschfeld |
| 5,304,487 A | 4/1994 | Wilding et al. |
| 5,312,527 A | 5/1994 | Mikkelsen et al. |
| 5,433,819 A | 7/1995 | McMeen |
| 5,434,049 A | 7/1995 | Okano et al. |
| 5,436,129 A | 7/1995 | Stapleton |

(Continued)

FOREIGN PATENT DOCUMENTS

| | | |
|---|---|---|
| EP | 0228075 B1 | 4/1991 |
| EP | 0320308 B1 | 11/1993 |

(Continued)

OTHER PUBLICATIONS

The definition for "genetic marker". Printed on Jan. 8, 2013.*
AAAC, "Hemochromotosis More Prevalent Than Previously Believed", Clinical Laboratory News 1999, vol. 25, No. 2.
Abrams et al., "Comprehensive Detection of Single Base Changes in Human Genomic DNA Using Denaturing Gradient Gel Electrophoresis & GC Clamp", Genomics, Aug. 1990, 463-475, vol. 7, No. 4.
Anand et al., "Pulsed Field Gel Electrophoresis", Gel Electrophoresis of Nucleic Acids—A Practical Approach, 1990, 101-123, Eds. D. Rickwood & B.D. Hames (New York: IRL Press).

(Continued)

*Primary Examiner* — Frank Lu

(74) *Attorney, Agent, or Firm* — John P. White; Cooper & Dunham LLP

(57) ABSTRACT

An assay system and methods are described where patient samples containing genomic DNA are analyzed for the presence of known genetic polymorphisms using a universal reporter strategy. In a preferred embodiment, the amplified DNA is localized at test sites in an array of sites on a microchip followed by a series of hybridization reactions that screen for the presence of a single mutation from among a number of mutations, and allow the identification of specific mutations. In addition to universal reporters, the assay may use blockers and discriminators for screening and identification of known polymorphisms.

7 Claims, 9 Drawing Sheets

(56) References Cited

U.S. PATENT DOCUMENTS

| | | | |
|---|---|---|---|
| 5,445,525 A | 8/1995 | Broadbent et al. |
| 5,445,934 A | 8/1995 | Fodor et al. |
| 5,464,517 A | 11/1995 | Hjerten et al. |
| 5,468,646 A | 11/1995 | Mattingly et al. |
| 5,474,895 A | 12/1995 | Ishii et al. |
| 5,516,641 A | 5/1996 | Ullman et al. |
| 5,516,698 A | 5/1996 | Begg et al. |
| 5,527,670 A | 6/1996 | Stanley |
| 5,552,270 A | 9/1996 | Khrapko et al. |
| 5,573,907 A | 11/1996 | Carrino et al. |
| 5,593,838 A | 1/1997 | Zanzucchi et al. |
| 5,602,240 A | 2/1997 | DeMesmaeker et al. |
| 5,605,662 A | 2/1997 | Heller et al. |
| 5,632,957 A | 5/1997 | Heller et al. |
| 5,635,352 A | 6/1997 | Urdea et al. |
| 5,653,939 A | 8/1997 | Hollis et al. |
| 5,660,701 A | 8/1997 | Grushka et al. |
| 5,681,751 A | 10/1997 | Begg et al. |
| 5,750,015 A | 5/1998 | Soane et al. |
| 5,766,960 A | 6/1998 | Cornell et al. |
| 5,770,365 A | 6/1998 | Lane et al. |
| 5,780,233 A | 7/1998 | Guo et al. |
| 5,789,167 A | 8/1998 | Konrad |
| 5,795,714 A | 8/1998 | Cantor et al. |
| 5,811,269 A | 9/1998 | Nadeau et al. |
| 5,849,486 A | 12/1998 | Heller et al. |
| 5,849,489 A | 12/1998 | Heller et al. |
| 5,849,544 A | 12/1998 | Harris et al. |
| 5,853,993 A | 12/1998 | Dellinger et al. |
| 5,908,745 A | 6/1999 | Mirzabekov et al. |
| 5,965,452 A | 10/1999 | Kovacs |
| 6,004,752 A | 12/1999 | Loewy et al. |
| 6,013,166 A | 1/2000 | Heller |
| 6,017,696 A | 1/2000 | Heller |
| 6,048,690 A | 4/2000 | Heller et al. |
| 6,051,380 A | 4/2000 | Sosnowski et al. |
| 6,054,270 A | 4/2000 | Southern |
| 6,068,818 A | 5/2000 | Ackley et al. |
| 6,071,394 A | 6/2000 | Cheng et al. |
| 6,099,803 A | 8/2000 | Ackley et al. |
| 6,129,828 A | 10/2000 | Sheldon, III et al. |
| 6,150,095 A | 11/2000 | Southern et al. |
| 6,207,373 B1 | 3/2001 | Sosnowski et al. |
| 6,306,348 B1 | 10/2001 | Havens et al. |
| 6,309,602 B1 | 10/2001 | Ackley et al. |
| 6,309,823 B1 | 10/2001 | Cronin et al. |
| 6,403,367 B1 | 6/2002 | Cheng et al. |
| 6,458,584 B1 | 10/2002 | Mirzabekov et al. |
| 6,468,742 B2 | 10/2002 | Nerenberg et al. |
| 7,601,493 B2 | 10/2009 | Radtkey et al. |

FOREIGN PATENT DOCUMENTS

| | | |
|---|---|---|
| GB | 2247889 A | 3/1992 |
| WO | WO 86/03782 A1 | 7/1986 |
| WO | WO 90/01564 A1 | 2/1990 |
| WO | WO 96/15271 A1 | 5/1996 |
| WO | WO 00/58522 A1 | 10/2000 |
| WO | WO 00/61803 A1 | 10/2000 |

OTHER PUBLICATIONS

Anderson et al., "Quantitative Filter Hybridization", Nucleic Acid Hybridization—A Practical Approach, 1985, 73-111, Eds. B.D. Hames & S.J. Higgins (Washington, D.C.: IRL Press).

Bains, Setting a Sequence to Sequence a Sequence, Bio/Technology, 1992, 757-758, vol. 10.

Barinaga, "Will 'DNA Chip' Speed Genome Initiative?", Science, 1991, 1489, vol. 253.

Beattie et al., "Genosensor Technology", The 1992 San Diego Conference: Genetic Recognition, Nov. 1992, 1-5.

Beltz et al., "Isolation of Multigene Families & Determination of Homologies by Filter Hybridization Methods", Methods in Enzymology, 1983, 266-285, vol. 100.

Bertina, "Mutation in Blood Coagulation Factor V Associated With Resistance to Activated Protein C", Nature, 1994, 64-67, vol. 369.

Broude, N.E. et al., "Enhanced DNA Sequencing by Hybridization", Proc. Natl. Acad. Sci., 1994, 3072-3076, vol. 91.

Brown et al., "Electrochemically Induced Adsorption of Radio-Labelled DNA on Gold & HOPG Substrates for STM Investigations", Ultramicroscopy, 1991, 253-264, vol. 38.

Fodor et al., "Multiplexed Biochemical Assays with Biological Chips", Nature, 1993, 555-556, vol. 364.

Fodor et al., "Light Directed, Spatially Addressable Parallel Chemical Synthesis", Science, 1992, 767-773, vol. 251.

Gills et al., "Single Nucleotide Polymorphic Discrimination by an Electronic Dot Blot Assay on Semiconductor Microchips", Nature Biotechnology, Apr. 1999, 365-370, vol. 17.

Gryaznov et al., "Enhancement of Selectivity in Recognition of Nucleic Acids Via Chemical Autoligation", Nucleic Acids Research, 1994, 2366-2369, vol. 22, No. 12 (University Press).

Guschin et al., "Manual Manufacturing of Oligonucleotide DNA, and Protein Microchips", Anal. Biochem., Aug. 1, 1997, 203-211, vol. 250, No. 2.

Holland, "Detection of Specific Polymerase Chain Reaction Product by Utilizing the 5'→3' Exonuclease Activity of Thermus Aquaticus DNA Polymerase", Proc. Natl. Acad. Sci. USA, 1991, 7276-7280, vol. 88.

Horejsi, "Some Theoretical Aspects of Affinity Electrophoresis", Journal of Chromatography, 1979, 1-13, vol. 178.

Horesji et al., "Determination of Dissociation Constants of Lectin Sugar Complexes by Means of Affinity Electrophoresis", Biochimica at Biophysica Acta, 1977, 200-300, vol. 499.

Howell, "Dynamic Allele-Specific Hybridization: A New Method for Scoring Single Nucleotide Polymorphisms", Nature Biotechnology, 1999, 87, vol. 17.

Kakerow et al., "A Monolithic Sensor Array of Individually Addressable Microelectrodes", Sensors & Actuators A, 1994, 296-301, vol. 43.

Khrapko, "An Oligonucleotide Hybridization Approach to DNA Sequencing" FEBS, 1989, 118-122, vol. 256 (1&2).

Khrapko et al., "A Method for DNA Sequencing by Hybridization With Oligonucleotide Matrix", DNA Seq., 1991, 375, vol. 1, No. 6.

Kieleczawa, "DNA Sequencing by Primer Walking With Strings of Contiguous Hexamers", Science, 1992, 1787, vol. 258.

Kotler, "DNA Sequencing: Modular Primers Assembled From a Library of Hexamers or Pentamers", Proc. Natl. Acad. Sci. USA, 1993, 4241-4245, vol. 90.

Landegren, "Reading Bits of Genetic Information: Methods for Single Nucleotide Polymorphism Analysis", Genome Research, 1998, 769-776, vol. 8.

Maldonado-Rodrequez et al., "Hybridization of Glass-Tethered Oligonucleotide Probes to Target Strands Preannealed with labeled Auxiliary Oligonucleotides", Mol. Biotechnol., 1999, 1-12, vol. 11, No. 1.

Maldonado-Rodrequez et al., "Mutation Detection by Stacking Hybridization on Genosensor Arrays", Mol. Biotechnol., 1999, 13-25, vol. 11, No. 1.

Mathews et al., "Analytical Strategies for the Use of DNA Probes", Analytical Biochemistry, 1988, 1-25, vol. 169.

Meade et al., "Electron Transfer Through DNA: Site-Specific Modification of Duplex DNA With Ruthenium Donors & Acceptors", Angew. Chem. Int. Ed. Engl., 1995, 353-354, vol. 34, No. 3.

Newton, "Analysis of Any Point Mutation in DNA. The Amplification Refractory Mutation System (ARMS)", 1989, Nucleic Acids Research, 2503, vol. 17, No. 7.

Norberg, "Solvent Influence on Base Stacking", Biophysical Journal, 1998, 394-402, vol. 74.

Orita, "Detection of Polymorphisms of Human DNA by Gel Electrophoresis as Single Strand Conformation Polymorphisms", Proc. Natl. Acad. Sci. USA, 1989, 2776-2770, vol. 86.

Ornstein, "An Optimized Potential Function for the Calculation of Nucleic Acid Interaction Energies. I. Base Stacking", Biopolymers, 1978, 2341-2360, vol. 17.

Palecek, "New Trends in Electrochemical Analysis of Nucleic Acids", Bioelectrochemistry & Bioenergetics, 1988, 179-194, vol. 20.

(56) References Cited

OTHER PUBLICATIONS

Parinov, "DNA Sequencing by Hybridization to Microchip Octa- and Decanucleotides Extended by Stacked Pentanucleotides", Nucleic Acid research, 1996, 2998-3004, vol. 24, No. 15.
Paton, Heterogeneity of the Amino Acid Sequence of *Escherichica coli* Shiga-like Toxin Type-1 Operons, Gene, 1995, 71-74, vol. 153.
Pieters, "Conformational & Thermodynamic Consequences of the Introduction Introduction of a Nick in Duplexed DNA Fragments: An NMR Study Augmented by Biochemical Experiments", Nucleic Acid Research, 1989, 4551, vol. 17, No. 12.
Ranki et al., "Sandwich Hybridization as a Convenient Method for the Detection of Nucleic Acids in Crude Samples", Gene, 1983, 77-85, vol. 21.
Saiki, "An Amplification of Genomic DNA", PCR Protocols: A Guide to Methods & Applications, 1990, 13-20, (Academic Press, Inc.).
Sinden, "Introduction to the Structure, Properties & Reaction of DNA", DNA Structure & Function, 1994, Chapter 1, (Academic Press).
Washizu, "Electrostatic Manipulation of Biological Objects", Journal of Electrostatics, 1990, 109-123, vol. 25.
Washizu et al., "Electrostatic Manipulation of DNA in Microfabricated Structures", IEEE Transactions on Industry Applications, 1990, 1165-1172, vol. 26.
Wu, "Specificity of the Nick-closing Activity of Bateriophage T4 DNA Ligase", Gene, 1989, 245-254, vol. 76.
Yershov et al., "DNA Analysis & Diagnostics on Oligonucleotide Microchips", Proc. Natl. Acad. Sci. USA, May 1996, 4913-4918, vol. 93.
Affymetrix, Data Sheet, GeneChip® Human Genome Arrays, 2003, 1-4.
Scouten et al., "Enzyme or Protein Immobilization Techniques for Applications in Biosensor Design", TIBTECH, vol. 13, May 1995, 178-185.
Halperin et al (2004) "Hybridization Isotherms of DNA Microarrays and the Qualification of Mutational Studies" Clinical Chemistry 50:12, 2254-2262.
Strachan and Read (1999) Human Molecular Genetics. $2^{nd}$ edition. New York: Wiley Liss; Bookshelf ID: NBK7567, Chapter 5, "Nucleic acid hybridization assays" pp. 1-11.
Aboul-ela et al (1985) "Base-Base mismatches. Thermodynamics of double helix formation for dCA3XA3G + dCT3YT3G (X, Y=A,C,G,T)" Nucleic Acids Research, 13(3)4811-4824.
Li and Liu (2003) "DNA Microarray Technology in Microbial Ecology Studies—Principle Applications and Current Limitations" Microbes Environ., 18(4):175-187.
Conner et al., "Detection of Sickle Cell $\beta^3$—Globin Allele by Hybridization With Synthetic Oligonucleotides", Proc. Natl. Acad. Sci. USA, 1983, 278-282, vol. 80.
Day, "Electrophoresis for Genotyping: Microtiter Array Diagonal Gel Electrophoresis on Horizontal Polyacrylamide Gels, Hydrolink, Agarose", Analytical Biochemistry, 1994, 389-395, vol. 222.
Drmanac et al., "Sequencing of Megabase Plus DNA by Hybridization: Theory of the Method", Genomics, 1989, 114-128, vol. 4.
Drmanac et al., "DNA Sequence Determination by Hybridization: A Strategy for Efficient Large Scale Sequencing", Science, 1993, 1649-1652, vol. 260.
Drobyshev et al., "Sequence Analysis by Hybridization With Oligonucleotide Microchip: Identification of β-Thalassemia Mutations", Gene 1997, 45-52, 188.
Drobyshev et al., "Massive Parallel Analysis of DNA-Hoeschst 33258 Binding Specificity with a Generic Oligodeoxyribonucleotide Microchip", Nucleic Acids Research, 1999, 4100-4105, vol. 27, No. 20.
Edman, C.F. et al., "Electric Field Directed Nucleic Acid Hybridization on Microchips", Nucleic Acids Research, 1997, 4907-4914, vol. 25, No. 24.
Eggers et al., "Biochip Technology Development", BioChip Technology Development, Lincoln Laboratory Technical Report 901, Nov. 9, 1990.
Feder, "The Hemochromatosis Founder Mutation in HLA-H Disrupts β2 Microglobulin Interaction & Cell Surface Expression", J. Biological Chemistry, 1997, 14025-14028, vol. 272, No. 22.
Fiaccabrino et al., "Array of Individually Addressable Microelectrodes", Sensors & Actuators B, 1994, 675-677, vol. 18-19.
Sosnowski, "Rapid Determination of Single Base Mismatch Mutations in DNA Hybrids by Direct Electric Field Control", Proc. Natl. Acad. Sci. USA, 1997, 1119-1123, vol. 94.
Southern, "Analyzing & Comparing Nucleic Acid Sequences by Hybridization to Oligonucleotides: Evaluation Using Experimental Models", Genomics, 1992, 1008-1017, vol. 13.
Southern, "DNA Chips: Analysing Sequence by Hybridization to Oligonucleotides on a Large Scale", Trends in Genetics, Mar. 1998, 110-115, vol. 12, No. 3.
Strezoska, "DNA Sequencing by Hybridization: 100 Bases Read by a Non-Gel Based Method", Proc. Natl. Acad. Sci. USA, 1991, 10089-10093, vol. 88.
Syvanen et al., "Fast Quantification of Nucleic Acid Hybrids by Affinity-Based Hybrid Collection", Nucleic Acids Research, 1986, 5037-5048, vol. 14, No. 12.
Syvanen et al., "Quantification of Polymerase Chain Reaction Products by Affinity Based Hybrid Collection", Nucleic Acids Research, 1988, 11327-11338, vol. 16, No. 23.
Syvanen et al., "A Primer Guided Nucleotide Incorporation Assay in Genotyping of Apolipoprotein E", Genomics, 1990, 684-692, vol. 8.
Tyagi, "Molecular Beacons: Probes That Fluoresce Upon Hybridization", Nature Biotechnology, 1996, 303, vol. 14.
Wallace et al., "Hybridization of Synthetic Oligodexribonucleotides to Φx174 DNA: The Effect of Single Base Pair Mismatch", Nucleic Acids Research, 1979, 3543-3557, vol. 6.
Wang, Large Scale Identification, Mapping & Genotyping of Single Nucleotide Polymorphisms in the Human Genome, Science, 1998, 1077, vol. 280.

\* cited by examiner

METHODS AND APPARATUS FOR SCREENING AND DETECTING MULTIPLE GENETIC MUTATIONS

This application is a divisional application and claims the benefit of U.S. patent application Ser. No. 10/627,950, entitled "Methods and Apparatus for Screening and Detecting Multiple Genetic Mutations," filed Jul. 24, 2003, now U.S. Pat. No. 7,601,493, which claims the benefit of U.S. Provisional Application Ser. No. 60/443,989, filed Jan. 30, 2003, and U.S. Provisional Application Ser. No. 60/398,992, filed Jul. 26, 2002, all of which are expressly incorporated herein by reference in their entirety.

FIELD OF THE INVENTION

The methods, apparatus, systems and reagents of these inventions relate to screening patient samples for genetic polymorphisms and for identifying specific polymorphisms within a known set. Particularly, the invention enables both high throughput screening and identification of known polymorphisms or mutations that relate to disease.

BACKGROUND

Many diseases are caused by known genetic alterations or mutations that occur in specific, identified regions in the DNA of a patient. Detection of a disease by direct analysis of DNA offers significant advantages in certainty and accuracy over other diagnostic techniques but requires an assay device and methodology that accurately detects and identifies the genetic alterations in a patient sample. When specific disease-related alterations or mutations can be detected and identified as markers of a disease, the DNA-based assays can be used both to diagnose an individual patient for disease and to screen patient groups for the presence of known genetic markers that may be correlated with disease. In some cases, populations of patients are uniquely susceptible to certain diseases or groups of diseases and DNA-based assays can be used to screen patients for any number of a group of diseases based on the detection of mutations in a patient's DNA.

In recent years, scientists have developed numerous techniques to analyze genetic material. Together with research that uncovered the specific genetic markers underlying certain diseases, researchers have developed techniques to detect the presence of specific alterations occurring in identified regions in a patient's DNA. Several analytical techniques are available to detect genetic alterations when present, however, the detection of small differences within the entirety of a patient's DNA requires a sophisticated test regimen and requires highly specialized biochemical reagents. For this and other reasons, much of the instrumentation and testing methods can only be performed in research environments and requires highly skilled technicians to conduct the analyses and interpret the results. Also, the testing of subtle genetic alterations is often time consuming and expensive to perform. The situation is complicated by the fact that many diseases have dozens of potential underlying genetic factors that play a role in the onset or progression of the disease, and as the number increases, the cost and complexity of an assay to test a patient's genetic material substantially increases.

In a clinical environment, a single patient can be tested for the presence of a large number of mutations or polymorphisms potentially underlying a suspected disease. When a screening approach is desired, the design of the assay technique becomes even more critical. If available, a screening assay would be highly desirable in several circumstances, including, to analyze the genetic basis for disease by detecting polymorphisms in patients and correlating the results to the presence, absence, or onset of one or more diseases, to screen susceptible groups of patients for genetic markers that exist for any of a group of diseases that are known to be passed from parent to child within ethnic groups, and to locate asymptomatic carriers of diseases who can pass the underlying mutation to offspring. An assay that is useful for a screening must be sufficiently reliable and cost-effective so that multiple tests can be efficiently performed on a large patient group.

For screening, an ideal testing system would be automated and capable of screening a large number of patient samples simultaneously and determining whether any one of a large number of mutations is present. Such a "high throughput" system would also require specially designed data processing so that assay results could be efficiently processed, correlated to patient data, and presented in a useful format for interpretation by clinical laboratory personnel. For analyzing patient samples, it is often desirable to test a large number of samples to first determine whether any one of a set of genetic markers is present, followed by analyzing individual samples to determine which member of the set of markers is present. In this fashion, multiple samples are screened to identify patients who are "positive" for a member of a set of markers, followed by identifying the specific mutation or polymorphism in the patient sample that yielded the positive signal. Furthermore, many diseases feature one or more of a small number of predominant mutations that occur with very high frequency. The existence of one or more predominant mutations may dictate that a testing assay should separately analyze selected mutations individually in a patient sample. Thus, the ideal screening and assay system would rapidly indicate, for an individual patient, whether or not any one or more of a set of known markers are present and would then offer the capability to identify, when a positive signal was generated in this screening process, the specific mutation or polymorphism that yielded the positive signal from among the larger set tested in the screening process.

Currently, a number of different techniques exist for direct analysis of a patient DNA sample. In one technique, synthetic strands of DNA are produced that have sequences that may or may not contain a mutation that are complementary to a select group of mutations and that can be used as probes to detect the mutation in a patient sample. These synthetic sequences are exposed to a patient sample, and when the mutation is present, the synthetic DNA becomes attached to the patient's DNA by hybridization. Once hybridized, the probe can be detected by several known techniques. Also, specific segments of patient DNA that may or may not contain a mutation can be amplified and the amplified DNA can be localized on an electronic microchip for further testing.

Cystic fibrosis (CF) is an example of a genetic disease that is caused, individually or collectively, by any of a number of different mutations. Cystic fibrosis afflicts approximately 30,000 children and adults in the United States; afflicted patients typically die in their thirties. One in 31 Americans (one in 28 Caucasians)—more than 10 million people—is an unknowing, symptom-free carrier of a mutation that leads to the disease. An afflicted patient must have inherited two defective copies of a specific gene—one from each parent—to have CF. Each time two CF carriers conceive a child, there is a 25 percent chance that the child will have CF, a 50 percent chance that the child will be an asymptomatic carrier; and a 25 percent chance that the child will be a non-carrier.

CF has a variety of symptoms that are manifested clinically. CF causes the body to produce an abnormally thick sticky mucus, due to the faulty transport of sodium chloride (salt) within cells lining organs such as the lungs and pancreas, to their outer surfaces. The thick CF mucus also obstructs the pancreas, preventing enzymes from reaching the intestines to help break down and digest food. CF patients also suffer from persistent coughing, wheezing or pneumonia; excessive appetite but poor weight gain and bulky stools. The sweat test is a common diagnostic test for CF. This test measures the amount of salt in the skin and a high salt level indicates that a person has CF.

The treatment of CF depends upon the stage of the disease and which organs are involved. One measure of treatment, chest physical therapy, requires vigor percussion (by using cupped hands) on the back chest to dislodge the thick mucus from the lungs. Antibiotics are also used to treat lung infections administered intravenously, via pills, and/or medical vapors that are inhaled to open up clogged airways. When CF affects the digestive system, the body does not absorb enough nutrients. Therefore, people with CF may need to eat an enriched diet and take both replacement vitamins and enzymes.

CF is known to be caused by a large number of mutations, at least 25 have been identified as major contributors to the disease. In August 2001, the American College of Gynecologists (ACOG) recommended testing the general group of potential parents for the 25 separate genetic markers to identify asymptomatic carriers who risk passing the disease to children. Because of the need to screen a large group of patients, a test for CF should rapidly and accurately screen multiple patient samples for the presence of any one or a set of known markers followed by the identification of one or more specific markers in those patients who test positive for at least one member of the set. Detection of whether or not any single one or more of the mutations exists provides a rapid screening method, and the detection and identification of the single mutation or number of mutations in a patient allows diagnosis of the disease or identification of a patient as a potential carrier.

In such situations, the design of the assay and methodology that efficiently achieves the goals described above is critical. Specifically, the assay must be rapid, accurate, and cost effective such that the assay can be performed as a routine part of patient care thereby expanding the utility of the assay from diagnosing individual patients to screening entire groups. The assay should be able to rapidly test multiple patient samples and be flexible enough to selectively recognize predominant mutations or markers for a disease. Through the ability to screen and identify a large number of genetic polymorphisms, the assay could both diagnose disease as well as yield epidemiological data about the prevalence of specific polymorphisms and the relation to the existence or severity of a condition that may be correlated to a specific disease or that exists in a number of pathologies. Because many diseases have underlying genetic markers that have been identified and localized to identified regions of a patient's DNA that can be analyzed, once the specific genetic markers are identified, any number of diseases can be analyzed using the same assay format by simply altering the gene specific reagents in the assay that hybridize with a patient's DNA to detect the known marker and correlating the presence of the marker with one or more diseases. Accordingly, once the assay design and methodology are realized, one additional disease, a group of diseases, or a group of polymorphisms that are directly or indirectly correlated to several diseases, can be detected with the assay format. As the genetic bases of other diseases are discovered, the gene specific assay reagents are readily modified to take advantage of the existing format to detect and analyze new diseases. For example, while cystic fibrosis is susceptible of detection by screening an identification of a discrete set of markers or mutations that are known to contribute to the disease, in other circumstances, the screening process may identify other polymorphisms that are not directly related to a single disease, but that are related to multiple diseases or that accompany different conditions such as a panel of diseases that may affect a certain population group.

SUMMARY OF THE INVENTION

The present invention provides methods, apparatus and compositions comprising reagents to screen patient DNA samples for the presence of one or more of a predetermined group or set of known genetic markers occurring at identified loci, together with the identification of specific markers in the sample. A number of patient samples may be individually screened to locate patients that test positive for any one or more of the markers in the set, followed by identifying the specific patients with one of a set of markers for further analyses to identify the specific polymorphism present. In preferred embodiments, a plurality of patient samples are simultaneously assayed for a group or set of markers by amplification of the identified regions of a patient's DNA that are known to include the mutation or polymorphism of interest and the localization or immobilization of the amplification products ("amplicons") on discrete test sites of an electronically addressable microchip. The microchip is comprised of an array of the test sites at which concentrations of the amplicons are localized for further reaction with specialized reagents. Once the amplicons are localized at the test site, several strategies are employed to interrogate the amplification products for the presence of any member of the known set of markers, followed by identification of the specific member of the set that was detected. Specifically preferred is the use of wild-type and/or mutant discriminator probes that engage in hybridization reactions to selectively detect any one of a set of mutations, followed by reaction with one or more universal reporters that provide universal detection capability such that a detectable signal is generated if any one of the members of a set of markers is present.

When an appropriate signal is detected in the amplified sample from an individual patient during the screening phase of the assay, the amplification products may then be analyzed in a genotyping assay to identify the specific mutation that generated the positive signal. Depending on the prevalence of specific, predominant mutations that are known for a particular disease, the assay may isolate a subset of predominant mutations for individual analysis in a patient sample before proceeding to the analysis of less prevalent mutations. The analysis of a prevalent mutation may occur as a discreet step or in parallel with other tests that comprise the entire screening or genotyping process. The predominant mutations may be directly correlated with a specific disease, or may be correlated with any of a number of conditions that exist in a certain group of diseases or other conditions where known genetic markers are identified.

Because of the large number of mutations that can be analyzed by the system of the invention, the amplification products of a patient's DNA sample may be electronically separated and localized onto specific microlocations or test sites of a microchip. In a preferred embodiment, immobilized amplicons are exposed to blocker sequences under hybridizing conditions such that the blocker sequences bind to the identified loci of the amplifications and prevent future hybridization reactions at the loci. Mutant or wild-type discriminator probes or both are introduced and hybridize with mutant or wild-type sequences that are not blocked by the blocker sequences. A universal reporter construct having a label indicates the presence or absence of the known set of markers tested in the assay. Mutant and wild-type discriminator probes may be used to screen for the presence or absence of any member of a set of known mutations, as well as to identify the individual members of the set that are present in patient sample. As described in further detail below, a universal reporter system provides an efficient strategy for screening the set of known mutations and identifying individual mutations within the set. Thus, in a preferred embodiment, amplification products of patient samples are exposed to any or all of blocker sequences, wild-type discriminator probes, mutant discriminator probes, universal reporters, and may be tested in parallel with control standards.

In a preferred embodiment, a first set of hybridization reactions, that may be referred to as a "screening phase" or "screening run" uses blocker sequences, mutant and wild-type discriminator probes, and a universal reporter to detect the signal generated by a label that indicates the binding of a mutant discriminator probe with the amplification products of any of a plurality of markers comprising a set of polymorphisms or mutations desired to be identified in a patient. The first hybridization occurs at discrete test sites that form an array on a microchip wherein selected members of the array of test sites are dedicated to the amplicons of a single patient sample. The first set of hybridization reactions yields a positive signal that is correlated to a specific patient by identification of the test sites. Where a positive signal occurs, a second set of hybridization reactions is performed at the specific test sites dedicated to the patient. The second set of reactions may be termed a "genotyping phase" or "genotyping run" and uses different groups of blockers together with the universal reporters and discriminator probes to distinguish the individual mutations or polymorphisms within the set. The microchip component of the system is preferred to be electronically addressable so that individual patient samples can be localized at predetermined test sites within the array identified by patient. As is described in more detail below, the sequential use of different groups of blocker sequences at the microlocations of the array is useful in both the screening aspect of the invention as well as in the genotyping process. Moreover, the advantageous use of universal reporters enables the assay to detect any member of a set of mutations using a minimal number of different labels, typically a number that is far fewer than the total number of markers tested by the assay. In a preferred embodiment, the assay both screens and genotypes for patient samples using universal reporters carrying a minimal number of separate label species including at least and typically less than 6 and all integral values therein.

In another embodiment, no "screening run" is performed and only "genotyping runs" are performed. Preferably, the genotyping runs are performed on an electronic array on a microchip. In a preferred embodiment, the array has 100 individually-addressable sites. More preferably, the array has 400 individually individually-addressable sites.

The preferred methodologies of the invention feature the advantageous use of the blocker sequences to separate and distinguish selected subsets of markers, wild type and mutant discriminator probes selectively detect the presence and/or identity of members of the known set of mutations, and universal reporters have labels that generate a signal upon hybridization with a common sequence of either the mutant or wild-type discriminator probes. In one embodiment of the invention, amplification products of a single patient are electronically addressed to a number of predetermined specific microlocations or on a microchip. As part of a screening step, different mixtures or groups of blockers specifically hybridize with identified loci of the amplicons. Loci that are not blocked hybridize with mutant or wild-type discriminator probes. By selecting mixtures of blocker sequences that are complementary to the identified loci of different subsets of the set of known markers, the detection of specific subsets can be localized at specific test sites for a specific patient. The reaction each discriminator probe generates a discrete signal that is detected by a signal detection and processing apparatus. Detection and signal processing steps distinguish the labels attached to mutant versus wild-type discriminator probes, subtract background signal, and generate a signal or report that identifies the assay results for a particular patient.

In the preferred embodiments described below, the specific mixtures of blocker sequences are selected so that every one of the set of known mutations is analyzed within the plurality of test sites dedicated to a single patient. Once the selected groups of blockers are applied, mutant and wild-type discriminator probes are added to each test site followed by the universal reporters to indicate the presence of one or more of a selected subgroup of markers tested at each microlocation and as defined by the blocker sequences. The universal reporters may be added at the same time as the discrimination probes or after the discrimination probes. By adding the universal reporters after the discrimination probes, the amount of universal reporter used in the assay can be reduced and the amount of non-specific binding of the universal reporter to the permeation layer can be minimized. The identity of the marker subset screened at each test site is a function of the specific group of blockers used at the test site, the subsequent reaction of the wild-type and mutant discriminator probes, the second application of a different group of blocker sequences, i.e. that block different loci than the first group. Because the universal reporter may generate the same signal when more than one mutation sequence is present, the identification of the specific mutations is derived from comparing the signal generated by the reporter following both applications of blocker groups and the application of the discriminator probes.

In CF for example, in the first set of hybridization reactions comprising the screening run, the assay may test for a total of 25 markers by testing, for example, a subset of between one and five mutations at each test site. In this example, the set of markers is comprised of 25 mutations or polymorphisms with a single predominant mutations and the amplicons from a single patient sample may be addressed to each of six test sites. One test site may be used for the predominant mutation, such that a group of 24 species of blocker sequences is introduced to the site to interrogate only the one remaining marker. At one other test site, blockers may block 20 of the identified loci and the remaining five markers are interrogated. Four other test sites are used analogously with different groups of blockers such that each marker is interrogated at one of the test sites. Because the predominant marker is interrogated individually at a dedicated test site, if the test site dedicated to the predominant marker tests positive, then the final result for that marker is achieved. If one of the other test sites generates a positive signal, the assay indicates that a member of a first subset, i.e. one or more of the markers interrogated at the site is present. Because more than one marker was interrogated at the test site, a subsequent set of reactions is required to distinguish which one or more of the five possible mutations is present. By removing the blockers and discriminators that were applied in the first hybridization reaction, a second set of blocker sequences can be applied to discriminate between the members of the subset of known mutations identified in the first reaction. The second set of hybridization reactions separates the members of the group of five identified in the first set by applying a second group of blockers that separate and distinguish the individual members of the subset. In this example, the second group of blockers is introduced to the test sites such that one test site interrogates one of the 5 members of the first subset identified in the screening run. Thus, the subsequent application of selected blocker groups identifies the individual within the subset identified in the screening step. In an alternative embodiment, the screening run may be skipped and only the genotyping runs may be performed. Preferably, the genotyping runs are performed on an array containing 400 individually-addressable sites or microlocations. The reaction of a universal reporter generates the signal, as above, and the identity of the mutation is indicated by the specific test site at which signal is generated. The example of cystic fibrosis is an embodiment of the invention where a defined group of markers is directly correlated to a particular disease. Because the invention provides the ability to detect a very large number of mutations, substantially larger than the 25 mutations detected for CF, the invention can be used to screen patient DNA samples for dozens of mutations that may directly or indirectly correlate to a number of diseases or which may be identified as accompanying other mutations that are associated with a disease or are of other clinical or research interest. As will be appreciated from the description of the invention, the assay is capable of generating a signal for the presence of a heterozygous mutation as well as a homozygous mutation. As described above in the context of cystic fibrosis, the presence of a heterozygous mutation may indicate the carrier of a disease while the presence of a homozygous mutation may indicate the symptomatic presence of the disease. Because the detection of a heterozygous mutation will inherently generate a different signal than the presence of the homozygous mutation, the assay methodology and apparatus distinguishes between a heterozygous and homozygous mutation. For example, when the first universal reporter hybridizes with a mutant discriminator probe, the signal generated by the label of the first universal reporter is different than the signal generated by a second universal reporter that hybridizes with a wild-type discriminator probe. Where no mutation is present, mutant discriminator will not be bound and the signal will be generated by the second universal reporter binding to wild-type discriminator probes. For a heterozygous mutation, a signal will be generated by a universal reporter binding to both a wild-type discriminator probe and a mutant discriminator probe. For a homozygous mutation, wild-type discriminator will not be bound and the signal generated will be from a universal reporter binding to both mutant discriminator probes. The detection and data processing components of the invention process these results by establishing parameters that separate signal from noise for each of the three possibilities outlined above, as well as establishing a heterozygous ratio reference to utilize the signal generated by two different species of label that result from the binding of two different universal reporters. To facilitate both qualitative and quantitative analysis of the various reactions described herein, the apparatus also employs reference and control reactions to ensure that the mutation detection functions are valid.

In another embodiment, a system for detecting members of a set of known polymorphisms that occur at identified loci in samples of patient DNA comprises loading amplified DNA from the identified loci at an addressable site, mutant discriminator probes comprising oligonucleotides selective for a member of the set of known polymorphisms and a first common nucleotide sequence, and a universal reporter comprising a label and a nucleotide sequence complementary to the first common nucleotide sequence of the mutant discriminator probe.

In another embodiment, a method is provided for detecting members of a set of known polymorphisms that occur at identified loci in samples of patient DNA. Initially, the patient sample containing multiple loci is loaded at a site. Blockers, which are selected for particular loci, hybridize with the patient sample, leaving at least two loci unblocked. Discriminators, which are capable of binding with the at least two loci, can then be hybridized with the patient sample. Hybridization events between the discriminators and unblocked loci can then be detected, thereby identifying the unblocked loci. Where a hybridization event is detected, the blocker mix can be changed in such a way that enables identification of the loci involved in the hybridization event. Preferably, the identity of the loci involved in the hybridization event is determined by selectively blocking the previously unblocked loci. This may be accomplished by changing the blocker mixes sequentially at a single site or changing the blocker mix simultaneously at the multiple sites.

In another embodiment, a method for detecting members of a set of known polymorphisms that occur at identified loci in samples of patient DNA comprises loading a patient sample containing multiple loci at multiple sites. Preferably, there is at least a first and second site. A first set of blockers is selectively provided for a subset of the loci to the first site and a second set of blockers, which are different from the first set of blockers, is selectively provided for a different subset of the loci at the second site. Discriminators are then provided for detecting the unblocked loci. The use of an actively addressable electronic microarray facilitates the selective provision of the blocker set to a desired site.

In another embodiment, a method is provided for detecting members of a set of known polymorphisms that occur at identified loci in samples of patient DNA. The sample of patient DNA to be analyzed is attached to a test site, the patient sample having multiple identified loci. A blocker set is provided to the patient sample so as to block some, but not all, of the loci. Discriminators are then provided for detecting unblocked loci.

Variations on the techniques described herein include where: the patient samples are amplified by in vitro methods, such as polymerase chain reaction (PCR), the ligase chain reaction (LCR), strand displacement amplification (SDA), the transcription-based amplification system (TAS), the self-sustained sequence replication system (3SR) and the Qβ replicase amplification system (Qβ). In one embodiment, multiple amplifications are accomplished in multiplex polymerase-based reactions with specially selected primers for identified loci of genomic DNA containing the known polymorphisms.

Considering yet further optional variations, the discriminators are capable of binding to both wild-type and mutant loci. The discriminator probes preferably include a common tail capable of hybridizing with or complementary to a universal reporter. Preferably, the common tails for the mutant discriminators and wild-type discriminators have different sequences and therefore, bind to different universal reporters. The method may also include the addition of stabilizers capable of binding to the patient sample. The stabilizers are chosen for their base-stacking ability. Optionally, the stabilizers may also serve a blocking function.

To facilitate rapid and automated performance of the assays of the invention, the apparatus has a computer controller, dedicated reagent supplies, a detector, and a software program to execute the several chemical reactions to detect generated signals, and to process the data generated by the assay methodology.

DETAILED DESCRIPTION OF THE INVENTION

Figure 1:
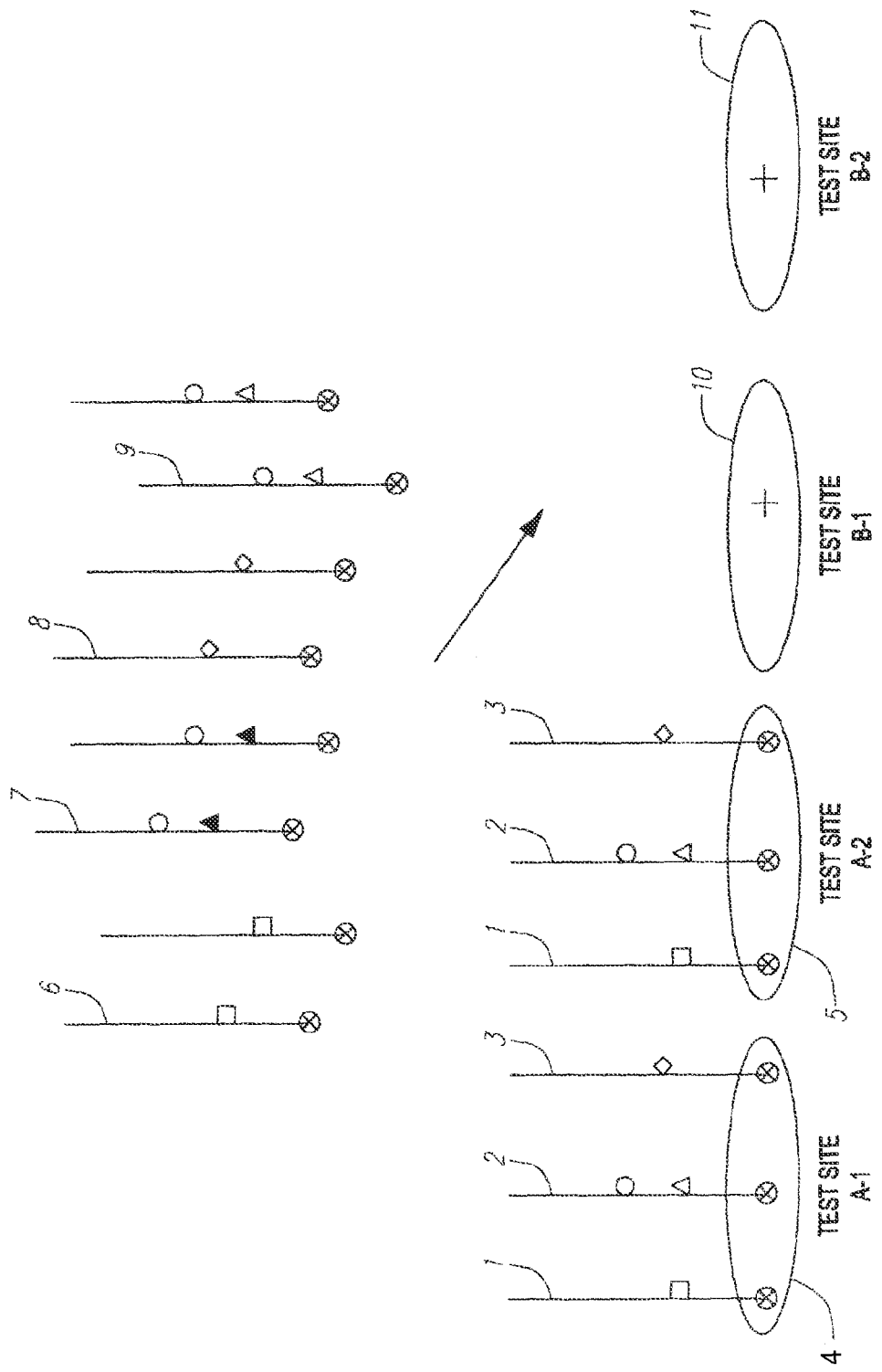
FIG. 1 is a schematic example of localization of amplified DNA from 2 individual patients indicated as to A,B two predetermined groups of test sites labeled A-1, A-2 for patient A and B-1, B-2 for patient B.

The present invention provides an assay system, method, and integrated components and reagents for screening and detection of multiple markers in a high throughput format. In this assay, specific regions of chromosomal DNA, which will also be referred to herein as identified loci, in patient samples are amplified and analyzed in an assay device comprised of a microchip that facilitates reacting the amplified DNA with reagents that facilitate identification of specific markers. The amplified sample is analyzed in the assay to simultaneously determine the presence or absence of one or more polymorphisms and to determine whether the polymorphism is present in one or both of a patient's chromosomes. The assay may be conducted in two steps wherein, in a first step, one or more patient samples are screened for any one or more of a set of markers. When a number of the set of markers is identified, a separate reaction identifies the individual members of the set that may be present. In preferred embodiments, the apparatus and methodologies have the capability to analyze several patient samples using a set of reagents that is specifically selected for the assay. The following definitions are used herein to describe the several embodiments of the invention.

An "amplicon" is an amplified polynucleotide sequence derived from a primer in an amplification reaction wherein a selected sequence is reproduced under reaction conditions that extend a primer sequence by sequential addition of nucleotides to encompass a target sequence.

"Amplification" refers to the process by which a region of a polynucleotide sequence is copied and expanded into a large number of amplicons. The polynucleotides contained in the patient samples are amplified by in vitro methods, such as the polymerase chain reaction (PCR), the ligase chain reaction (LCR), rolling circle, strand displacement amplification (SDA), nucleic acid sequence based amplification (NASBA) the transcription-based amplification system (TAS), the self-sustained sequence replication system (3SR) and the Q.beta replicase amplification system (Qβ).

"Blockers" are polynucleotides that hybridize specifically to polynucleotide sequences, usually amplicons, and that are designed to prevent binding by wild-type and mutant discriminator probes.

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second. Thus, the polynucleotide whose sequence 5'-TATAC-3' is complementary to a polynucleotide whose sequence is 5'-GTATA-3'.

"Detectable moiety" or "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantitate the amount of bound detectable moiety in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second directly or indirectly detectable moiety to the detectable moiety. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P. D. Fahrlander and A. Klausner, Bio/Technology (1988) 6:1165.) Quantitation of the signal generated by a label is achieved by known detection and measurement techniques, e.g., scintillation counting, densitometry, or flow cytometry.

A "discriminator" or "discriminator probe" is a polynucleotide that selectively binds to a polymorphic region of an amplicon, wherein the region may or may not contain a mutation. Specific discriminator binding to a known, predetermined mutation is sometimes referred to herein as "querying." Each different polymorphic region may be referred to as a "variant." "Wild-type discriminators" bind to wild-type sequence, while "mutant" discriminators bind to variants including recognized mutations, or simple variants of the wild-type sequence that may be described as markers or polymorphisms. A "pair of discriminators" typically consists of the wild-type discriminator and the corresponding mutant discriminator for a specific polymorphism. Discriminators may consist of one that specifically binds to the sequence of a specific variant or of two polynucleotides that specifically bind, in direct apposition, to a contiguous sequence of a specific variant and are designed so that a first stabilizes the binding of a second by base stacking. The use of two polynucleotides and base stacking to obtain highly stable hybridization complexes capable of precise discrimination is described in Radtkey R. et al., *Nucleic Acids Research*, 28(7): i-vi (2000) and Yershov, G. et al., *Proc. Nat'l Acad. Sci. USA*, 93: 4913-18 (May 1996).

"E-stripping" is electronic denaturation of double stranded polynucleotides or removal of hybridized polynucleotides.

"Heterozygous" means that one chromosome from a patient sample contains a mutant variant and the other contains the corresponding wild-type variant.

"Heterozygous ratio references" are polynucleotides that each bind specifically to one discriminator pair. Each heterozygous ratio reference contains one or more polynucleotides that bind to one pair of discriminators.

"Homozygous" means that both chromosomes from a patient sample contain a mutant variant or that both contain a wild-type variant.

"Hybridizing specifically to" or "specific hybridization" or "hybridize to," refers to the binding, duplexing, or hybridizing of a nucleic acid molecule preferentially to a particular nucleotide sequence under stringent conditions when that sequence is present in a complex mixture.

"Localized" means that a composition is concentrated at a test site to a level greater than in ordinary solution and which is greater than would occur through passive hybridization. In the context of an amplicon localized at a test site, the amplicon has a greater concentration achieved through chemical, electrical, or biochemical reaction, as opposed to mere selective placement at the test site.

The terms "mutation" or "polymorphism" describe nucleotide sequences that vary from a wild-type sequence by a known parameter such that the distinction can be interrogated with a discriminator probe. In typical usage, mutation usually refers to variant the wild-type sequence that is correlated to disease. A polymorphism may also be a mutation, but may also refer to a difference from the wild-type sequence that has no known correlation to disease. Both mutations and polymorphisms may broadly be described as "markers" for a disease or a marker may simply represent an identifiable sequence in comparison to wild-type. Markers, mutations, or polymorphisms may be deletions, substitutions, repeats, transpositions, etc.

An "oligonucleotide" is a polymer of nucleotides.

A "primer" refers to a polynucleotide that is capable of specifically hybridizing to a designated polynucleotide template and providing a point of initiation for synthesis of a complementary polynucleotide under synthesis inducing conditions i.e., in the presence of nucleotides, a complementary polynucleotide template, and an agent for polymerization such as DNA polymerase. A primer is typically single-stranded deoxyribonucleic acid, but a wide variety of synthetic and naturally occurring primers are useful. A primer is complementary to the template to which it hybridizes to serve as a site for the initiation of synthesis.

A "reflex test" occurs when a positive genotyping result requires an additional test.

A "reporter" refers to a polynucleotide that is capable of specifically hybridizing to a designated sequence of another polynucleotide and that contains a label. A probe specifically hybridizes to a target complementary polynucleotide, but need not reflect the exact complementary sequence of the template. In such a case, specific hybridization of the probe to the target depends on the stringency of the hybridization conditions. Probes can be labeled with e.g., chromogenic, radioactive, chemiluminescent, enzymatic, colorimetric, or fluorescent moieties and used as detectable moieties.

"Screening" is a step in the assay during which it is determined whether or not a sample contains any one of a group of polymorphism that are usually mutations that are known to be related to disease. If a sample tests positive, the presence of a mutation within the subset is indicated and the sample can then be further analyzed or "genotyped." "Genotyping" refers to determining whether a patient sample is homozygous for wild-type, homozygous for a particular mutant variant, or heterozygous for a particular variant.

The terms "selective for" or "selectively hybridize to" describe differential reactivity between wild type and a mutant variant of a probe in a hybridization reaction with a complementary sequence of an amplicon. A mutant discriminator probe is selective for a specific known polymorphism or mutation such that hybridization does not occur to a wild-type sequence. Similarly, a wild-type discriminator probe is selective for the wild-type sequence such that hybridization only occurs to the wild-type sequence and not to a polymorphism or mutation.

The terms "stringent conditions" refer to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays," Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

A "universal reporter" refers to a polynucleotide that 1) possesses a moiety (e.g. a nucleotide sequence) that interacts with a series of nucleotide sequences, each in the series having the same moiety complementary to the universal reporter and a region specific for differing genetic loci, and 2) possesses a detectable moiety.

Device for Simultaneous Detection of Multiple Markers

The apparatus of this invention includes an electronically addressable microchip device, many of the components of which are described in the following applications and patents, which are specifically incorporated herein by reference:

application Ser. No. 09/671,954, filed Sep. 27, 2000, and entitled "ELECTRONIC SYSTEMS, COMPONENT DEVICES, MECHANISMS, METHODS, AND PROCEDURES FOR MACROSCOPIC AND MICROSCOPIC MOLECULAR BIOLOGICAL REACTIONS, ANALYSES AND DIAGNOSTICS", now U.S. Pat. No. 6,780,584, application Ser. No. 08/986,065, filed Dec. 5, 1997, entitled "methods and procedures for molecular biological analysis and diagnostics", now issued as U.S. Pat. No. 6,051,380, which is a continuation-in-part of application Ser. No. 08/855,058, filed May 14, 1997, entitled "METHODS FOR ELECTRONIC FLUORESCENT PERTURBATION FOR ANALYSIS AND ELECTRONIC PERTURBATION CATALYSIS FOR SYNTHESIS", now issued as U.S. Pat. No. 6,048,690, which is a continuation-in-part of application Ser. No. 08/534,454, filed Sep. 27, 1995, entitled "APPARATUS AND METHODS FOR ACTIVE PROGRAMMABLE MATRIX DEVICES", now issued as U.S. Pat. No. 5,849,486, which is a continuation-in-part of application Ser. No. 08/304,657, filed Sep. 9, 1994, entitled "AUTOMATED MOLECULAR BIOLOGICAL DIAGNOSTIC SYSTEM," now issued as U.S. Pat. No. 5,632,957, which is a continuation-in-part of application Ser. No. 08/271,882, filed Jul. 7, 1994, entitled "METHODS FOR ELECTRONIC STRINGENCY CONTROL FOR MOLECULAR BIOLOGICAL ANALYSIS AND DIAGNOSTICS," now issued as U.S. Pat. No. 6,017,696, and which is a continuation-in-part of Ser. No. 08/146,504, filed Nov. 1, 1993, entitled "ACTIVE PROGRAMMABLE ELECTRONIC DEVICES FOR MOLECULAR BIOLOGICAL ANALYSIS AND DIAGNOSTICS", now issued as U.S. Pat. No. 5,605,662. The microchip device described in the applications and patents includes an array of microlocations or test sites each associated with an electrode. The electrode is overlaid with a permeation layer that separates the polynucleotides from the surface of the electrode. The device also includes an attachment layer to which molecules such as nucleic acids are bound. Specific binding entities such as affinity binding pairs are immobilized on the attachment layer. For example, streptavidin can be incorporated into the permeation layer, providing an affinity binding site for nucleic acids that have been derivatized with biotin. The amplification primers may be biotinylated such that the amplicons are comprised of amplified loci of a patient sample and a first member of a binding pair wherein the second member of the binding pair is integral with the microchip. Charged molecules are electronically addressed to a specific test site by biasing the electrode underlying the test site with a charge opposite that of the target molecule. This process also results in localization of the molecule at the test site. In addition, the surrounding test sites may be biased with the same charge as the charged molecule such that the charged molecule is repelled.

In a preferred embodiment, the microchip device is coupled to a reader that detects signal generated by the labels attached to universal reporters that are hybridized to discriminator probes at the various test sites. In a particularly preferred embodiment, the reader detects at least two discrete wavelengths of fluorescent light generated by fluorescent labels incorporated into the universal reporters. The reader may be comprised of a discrete light source and a detector designed to detect a signal from the interaction between light from the source and a label used in the assay. Alternatively, the reader may obtain an image of the device during the assay, followed by image analysis to determine the results of the assay. In either embodiment, the reader detects the signal(s) generated by the reporter label(s) and determines intensity as well as a comparative value compared to like signals generated by the same label, or distinct signals generated by a different label or combination of labels. Where labeling by different reporters yields different signals, such as different fluorescent wavelengths, the detector measures the relative strengths of the signals at one or more locations, such as the test sites of the microchip, and may translate any of these detections into a signal for further processing by electronic means or through computer software that manipulates the signal to generate a data report of the results of the assay. In a particularly preferred embodiment, the microchip is also coupled to a loader capable of transferring sample from one container, such as a microtiter plate, to the microchip device and is capable of transferring members of the reagent set of the invention to the microchip.

The invention also includes a specific reagent set used in the system. In a preferred embodiment, the system encompasses integral containers for reagents such as sets of primers, discrete groups of blockers, including the arrangement of blockers in predetermined subsets to interrogate subsets of known mutations, wild-type and mutant discriminator probes, universal reporters comprising labels and heterozygous ratio references. In a particularly preferred embodiment, the apparatus also includes a background control and a reagent set of amplification controls.

The blocker compositions each contain groups of sequences that are specifically hybridized to identified loci on an amplicon that contains one or more of the variants being assayed. The individual blocker groups are substantially homogenous mixtures of discrete nucleotide sequences that specifically hybridize to identified loci at the amplicon and prevent the selective binding of mutant or wild-type discriminator probes. One blocker group may bind a set of identified loci or may block only a single locus. In the latter case, blocking more than one identified locus requires more than one blocker group. In a preferred embodiment, the blockers are of sufficient length to remain hybridized through sequential rounds of discriminator hybridization and subsequent denaturation of the discriminators. This length is determined empirically. The blocker mixtures are electronically addressed to selected microlocations and hybridize to amplicons which prevents the reaction of the amplicons with selected mutant and/or wild-type discriminators binding of the mutant and/or wild-type discriminator probes to the amplified polynucleotides does not occur above a threshold level that is capable of being removed as a background signal.

In preferred embodiments of the assay, the blockers are organized into screening mixes and genotyping mixes. Each screening mix is unique, consists of one or more blockers, and is designed to block a particular subset of the known markers being assayed, with each mixture blocking some, but not all, loci. The loci not blocked by a particular blocking group will be referred to as a "screening loci group." Each genotyping mix is unique, consists of one or more blockers, and is designed to block some variants but to leave unblocked one loci from each screening loci group. Thus, if blocker mix A blocks all loci except 1-3, blocker mix B blocks all loci except 4-6, and blocker mix C blocks all loci except 7-9, genotyping mix A will block all loci except 1, 4, and 7, genotyping mix B will block all loci except 2, 5, and 8, and genotyping mix C will block all loci except 3, 6, and 9.

In a preferred embodiment, the apparatus also includes amplification controls. The amplification process, one example of which is described in more detail below, is comprised of any process that accurately and reproducibly copies a defined and identified region of a gene wherein an identified locus exists that contains a polymorphism. Because the sequence of at least a portion of the identified locus is known, a group of primers can be selected to amplification of discrete genetic loci in a patient sample where the mutations are known to occur. The identification of the sequence of a primer useful for amplifying a specific locus in a patient sample is a routine matter for one of ordinary skill in the art and a preferred set of reaction parameters and amplification reagents are described in the examples herein. The amplification controls are polynucleotides that bind specifically to portions of each amplicon in order to verify the presence of a specific amplicon and to verify that the amplification reaction has successfully amplified the desired regions of the pertinent sample when certain mutations occur. Each amplification control binds to a different amplicon, such that a full set of amplification controls contains one amplification control per amplicon. In addition, the amplification controls are designed so that they can be denatured from the amplicons under less stringent conditions than are the blockers. In a preferred embodiment these amplification controls are wild-type discriminators. Also, in a preferred embodiment, amplification controls are designed to have a melting temperature within the operation temperature of the testing platform and a temperature empirically determined to be low enough to allow removal by chemical, thermal or e-stripping without denaturing blockers.

In a preferred embodiment the apparatus also includes a set of heterozygous ratio references. Each heterozygous ratio reference contains sequences that are complementary to one discriminator pair. The heterozygous ratio references are capable of attachment to the attachment layer of the microchip device. In a preferred embodiment, the polynucleotides comprising each heterozygous ratio sequence are biotinylated.

The system of the invention also includes a selected group of reagents including a set of discriminators that are specific for all of the wild-type and mutant variants associated with the particular disease being assayed. Each individual discriminator species contains a nucleotide sequence that is complementary to a sequence in an amplicon. Wild-type and mutant discriminators differentially and selectively react with either wild-type or discriminator sequences, respectively, present in the amplicons, when those regions of the amplicons are not blocked by the blocker sequences. The discriminators are preferably designed so that an entire set of discriminator pairs can be denatured from the amplicons under less stringent conditions than are the blockers. In one embodiment, wild-type and mutant discriminator probes are about 30-40 nucleotides in length and have a melting temperature between 35° C. and 45° C. In a preferred embodiment, the wild-type and mutant discriminator probes have a melting temperature that is about 20° C. less than the melting temperature of the blocker(s) that bind to the same variant as does the discriminator.

The apparatus also includes labels for detecting the binding of at least the mutant discriminator, and preferably the wild-type discrimination and the amplification controls to the amplicons. Amplification controls and discriminators are associated with distinguishable labels so that more than one amplification control or discriminator can be detected at one microlocation. In one embodiment, the label is attached directly to the amplification controls and discriminators.

In the preferred embodiment, the label is coupled to a construct that acts as a universal reporter to specifically hybridize to a common region in the amplification controls and either of the discriminators sometimes referred to herein as a "tail." In this embodiment, each amplification control and discriminator is designed to contain at least one tail. To distinguish the wild-type discriminators from the mutant discriminators, the tail sequence of a mutant discriminator may be complementary to the nucleotide sequence of a first universal reporter that has a first label. Accordingly, the tail sequence of the wild-type discriminator probe may be common and complementary to the nucleotide sequence of a second universal reporter having a second label. Detection of the different signals generated by the first and second labels distinguishes the reaction by the wild-type and mutant discriminators with the amplified patient DNA. Thus, in the preferred embodiment, the universal reporter contains a polynucleotide sequence that is complementary to the above-described tail such that the universal reporter binds to the tail of the discriminators under the hybridization conditions of the assay. The universal reporters that specifically bind to one tail are coupled to a label that is distinguishable from the label coupled to any other universal reporter that specifically binds to another tail. Thus, a first tail is associated with a first label, a second tail with a second label, and a third tail with a third label, and so on, wherein the first, second, third and additional labels are distinguishable. In a preferred embodiment more than one amplification control contains the same tail or tails. In a particularly preferred embodiment a first group of the amplification controls contain a first tail while a second group contains a second tail.

In the preferred embodiment, wild-type and mutant discriminators contain different tails, but all of the wild-type discriminators contain a common first tail and all of the mutant discriminators contain a common second tail that are different from the first tail. In another embodiment, at least one discriminator has a first tail, at least one discriminator has a second tail, at least one discriminator has a third tail, and at least one discriminator has a fourth tail, wherein the first, second, third, and fourth tails are different. To facilitate generating stronger signals for one type or species of discriminator probe, the discriminator probes may contain more than one tail so that a plurality of individual universal reporter molecules bind to the same discriminator probe. Thus, to increase the signal generated by the binding of a mutant discriminator probe to an amplicon, the mutant discriminator probe could be designed to have two tail regions such that two universal reporters, and accordingly two labels, are bound to the same mutant discriminator probe. In a preferred embodiment, the wild-type and mutant discriminator probes have the same sequence. In this embodiment, the wild-type sequence is of a sufficient length that it is still able to bind to the amplicon containing the mutation.

Compounds commonly used to label nucleic acid probes are enzymatic compounds, fluorescent compounds, phosphorescent compounds, chemiluminescent compounds, and/or compounds providing a colorimetric, enzymatic, radioactive, or other detectable signal. These compounds can be coupled to polynucleotides by methods well known to those of skill in the art. In a preferred embodiment, the labels will be a minimum number of fluorescent labels that generate a signal read by the reader that is integral to the assay device. The synthesis of polynucleotides with defined sequences, such as those described herein, is well known to one of ordinary skill in the art. For instance, the various polynucleotides described above may be ordered from several commercial sources, such as Integrated DNA Technologies (Coralville, Iowa) or Oligos, Etc. Inc. (Wilsonville, Oreg.), or synthesized using a commercially available polynucleotide synthesizer such as the ABI 3900 High Throughout DNA Synthesizer (Applied Biosystems, Foster City, Calif.).

Simultaneous Assay for Multiple Mutations

The present invention also relates to a method for simultaneously assaying multiple markers related to the same disease or to a panel of diseases, or to a set of known polymorphisms in multiple patient samples to determine whether a patient is heterozygous, homozygous wild-type, or homozygous mutant for each marker, using the above-described device. Several diseases, groups of diseases, or polymorphisms of clinical or research interest are associated with the presence of one or more known mutations in the human genome and can be detected using this assay. Examples of disease-related mutations that can be detected with this assay are the mutations associated with any one or more of Cystic Fibrosis, Beta-Thalassemia, hereditary hemochromatosis, Gaucher, Tay-Sachs, Nieman-Pick, HIV, epilepsy, and others. In addition to identifying diseases in patient samples, the simultaneous assay for multiple markers may also be used for identification in DNA fingerprinting.

The assay is performed on any sample that contains DNA, such as, for example, blood, urine, sputum, amniotic fluid, or buccal. The loci of the DNA in the sample that are identified as containing the known polymorphism(s) are amplified. The amplification methods include polymerase chain reaction (PCR), the ligase chain reaction (LCR), strand displacement amplification (SDA), the transcription-based amplification system (TAS), the self-sustained sequence replication system (3SR) and the Qβ replicase amplification system (Qβ). In one embodiment, multiple amplifications are accomplished in multiplex polymerase-based reactions with specially selected primers for identified loci of genomic DNA containing the known polymorphisms. Polymerase chain reaction and, more specifically, multiplex polymerase chain reaction are described in Innis, M. A. et al., *PCR Applications: Protocols for Functional Genomics*, (San Diego: Academic Pres. 1999).

The resulting amplified polynucleotides for an individual patient are localized, preferably by electronic addressing, to a discrete set of test sites on the microchip device. Preferably, the group of amplicons for an individual patient are addressed to a number of target sites that is less than the total number of polymorphisms to be detected in the assay. Once the amplicons are electronically addressed, the detection of polymorphisms is achieved through hybridization reactions occurring at the microlocations. A first run of hybridizations is primarily a screening run, however, genotyping of single mutations, typically one or more predominant mutations that is most commonly associated with a disease, may also occur during the screening run. A second run of hybridizations is a "genotyping run" to determine which particular mutation or mutations is present in the sample and whether the sample is homozygous or heterozygous for that mutation. Additional hybridization runs may be added to identify additional mutations or further characterize specific mutations related to those identified through the first two runs.

Screening Run

During the screening run, amplicons and blockers are electronically hybridized to predetermined test sites on the microchip device that are preferably assigned or dedicated to an individual patient. Data from a particular test site so identified can be correlated with 1) a particular patient and presence or absence of a particular amplicon and/or 2) a particular patient and presence or absence of a particular marker or markers. In addition, the full set of mutant discriminators, and in some embodiments certain wild-type discriminators, are loaded onto the device. Amplification controls and discriminators, which may also be associated with labels, are provided along with the universal reporter constructs.

Hybridizing Amplicons, Blockers, and Controls

A complete set of amplicons from one patient, when electronically addressed to each of a specific number of predetermined microlocations will be collectively referred to as a "suite." Electronic addressing of amplicons to a permeation layer of the microchip is described in, for example, U.S. Pat. No. 6,051,380, which is expressly incorporated herein by reference. The attachment of the amplicon to the microlocation can be achieved by covalent chemical binding, or through the use of a binding pair of any type. The binding pair may be comprised of any two species that react to maintain the location of the amplicon at a specific test site. Specifically preferred is the use of an affinity binding pair such as streptavidin, which is incorporated into the permeation layer of the microchip device, and biotin-labeled amplicons such that the streptavidin immobilizes the amplicons by the biotin streptavidin affinity bindings, thereby fixing the amplicons to the permeation layer. As noted, the amplicons may also be chemically modified with a linking moiety to provide covalent binding to the substrate.

In addition, in a particularly preferred embodiment, each set of amplicons is addressed to non-adjacent test sites, such that amplicon sets derived from the same patient are not addressed to adjacent microlocations. In a preferred embodiment one predetermined test site is used to provide a background reading. In one embodiment this background test site is empty. In another embodiment, this background test site is addressed with a synthetic polynucleotide.

If one of the mutations in the known set is predominant, such as the delta F508 deletion with cystic fibrosis, that mutation may be both screened and genotyped simultaneously in the first set of hybridization reactions. As described in detail below, a heterozygous ratio reference that specifically binds the discriminator pair for delta 508 is then used to query the predominant mutation.

Once electronic addressing of the amplicons is complete, the amplicons are denatured leaving single stranded polynucleotide. As an option to electronic addressing of the amplicons, the amplicons can be generated on the microchip by the electronic addressing of sense and antisense primer pairs to microlocations followed by electronic addressing of patient genomic DNA as template and addition of amplification reaction components and incubation of the microchip under conditions for amplification. This process results in generation of both the sense and antisense strands attached to the microlocation. Denaturation of the amplicons occurs as described with the exception that both single strands remained attached to the test site. Those of skill in the art will recognize that there are several ways to denature double-stranded polynucleotides. In one embodiment, the amplicons are denatured using sodium hydroxide. In a particularly preferred embodiment the amplicons are e-stripped in a similar way to electronic addressing. The electrodes underlying the test site to which the sets of amplicons are addressed are positively biased to denature the amplicons, repelling the non-biotinylated strand as described in U.S. Pat. No. 6,051,380.

After denaturation of the amplicons, different screening blocker groups are electronically addressed to a predetermined test sites within each suite and bind to the complementary regions of the amplicon as described in more detail herein, the sequences of the blocker groups are specifically designed to hybridize to the regions of the amplicons that contain the mutant or wild-type sequences and hybridize to the amplicons to prevent further reaction with the mutant or wild-type discriminator probes. The blocker groups each include a unique mix of blocker sequences such that, at each of the test sites in a suite, a different known group of variants, i.e., the screening variant group, remains unhybridized.

In one embodiment, where a mutation is commonly associated with a disease, which will be referred to as a "predominant mutation," is genotyped in the first run, one blocker group blocks all of the variants except the predominant mutation. This predominant mutation blocker group is electronically addressed to one test site per suite. Test sites at which screening will be performed are referred to as "screening sites," while test sites at which genotyping will be performed are referred to as "genotyping sites."

In a preferred embodiment, after addressing of the blocker groups, amplification controls are introduced to each amplicon-bearing test site. This can be optional if other methods of amplification confirmation are used. Each amplification control is introduced to the particular test site in each of the suites on the microchip device that should contain an un-hybridized (i.e. unblocked) region for which the particular amplification control is specific. The amplification controls bind to the unblocked amplicon region to which at least part of the amplification control is complementary. The amplification controls are hybridized in such a way that, at each test site per suite, the presence or absence of at least one amplicon is detected.

In a preferred embodiment, after different blocker sets are electronically addressed to each amplicon-bearing test site, the amplification controls are hybridized to the particular test site in each of the suites on the microchip device that should contain an un-hybridized (i.e. unblocked) region for which the particular amplification control is specific.

As described above, these amplification controls are associated with a construct containing a label. In a preferred embodiment, the construct is a universal reporter. After the amplification controls are hybridized the universal reporter is loaded onto the microchip device and specifically binds to the tail portion of the amplification control. In a particularly preferred embodiment, before hybridizing the amplification controls, the universal reporters are mixed with the amplification controls and specifically bind to the tail portion of the amplification control.

After hybridizing of the amplification controls and, in preferred embodiments, hybridization to universal reporters, a reader scans the microchip device, detecting the signal associated with the amplification controls and with the background control. These scans will be referred to as "amplification scans." In embodiments in which multiple labels are detected, the reader performs one scan of the microchip device per label. In a preferred embodiment in which fluorescent labels are used, each scan will detect a different wavelength of fluorescent light.

In the embodiment where amplification controls are used, the controls are denatured after scanning along with their labels to leave the groups of blockers hybridized to the amplicons. Denaturation can occur in a variety of ways, including thermal denaturation, chemical denaturation, and e-stripping. In a preferred embodiment the amplification controls are removed by thermal denaturation.

Mutant discriminators that are selected for each polymorphism are then loaded onto the microchip device under stringent conditions conducive to selective hybridization of discriminator probes to the amplicons. In a preferred embodiment, discriminator probes are hybridized by a touch down thermal method in which the microchip device is heated before and for a short period after the discriminator probes are added and then the temperature is slowly decreased. These temperature changes are followed by or performed in conjunction with several high salt washes to further increase specificity of the discriminator probe binding. In another preferred embodiment, discriminators are hybridized using non-stringent conditions such that both wild-type and mutant signals are approximately equal. Following hybridization, discrimination occurs using thermal, chemical, or e-stripping, leaving only matched signals.

If the presence of all amplicons could not be verified with the hybridizing of amplification controls described above, e.g., if the number of amplicons in a set exceeds the number of screening test sites multiplied by the number of different labels that can be detected at each test site, the presence of the remaining amplicons can be verified during the discriminator probe hybridization step, preferably using wild-type discriminators. When so used, the wild-type discriminator probes must be associated with a different label from the label associated with the mutant discriminator probes.

In a preferred embodiment in which at least one predominant mutation is screened and genotyped in the first hybridization run, the wild-type discriminator that specifically binds to the identified loci on the amplicons containing the predominant mutation is also loaded onto the microchip device such that either the mutant or wild-type discriminator will bind to the amplicons at the test site to which all blocker groups were addressed. In addition, this set of discriminators will bind to the heterozygous ratio reference for the predominant mutation.

In one embodiment in which the universal reporter construct contains a label, after the discriminators and amplification controls have hybridized to the amplicons, the universal reporter is loaded onto the microchip device and specifically binds to the common sequence of the tail of the discriminator probes. In a preferred embodiment, before the discriminator probes and amplification controls are loaded onto the microchip device, the universal reporters are mixed with the amplification controls and/or discriminator probes and hybridize to the common tail portion of the amplification controls and/or discriminators.

After hybridizing of the amplification controls and, in some embodiments, hybridization to universal reporters, a reader scans the microchip device, detecting the signal associated with the discriminator probes, with the amplification controls, if any, and with the background control. The scans will be referred to as "discriminator scans." In embodiments in which multiple labels are detected, the reader performs one scan of the microchip device per label. In a preferred embodiment in which fluorescent labels are used, each scan will detect a different wavelength of fluorescent light.

In a preferred embodiment at least some of the steps described above can be accomplished using a computer system coupled to the device in the manner described below. In a preferred embodiment, at least some of the steps described above are automated.

Analysis of Signal

Once the hybridization reactions are completed and the labels detected to yield a signal, the signal gathered from each test site in the amplification scans and/or the discriminator scans is then analyzed. The analysis outlined below may be performed by a computer system coupled to the reader. Signal from each test site except the background control test site will be referred to as "raw test site signal" or "RTSS." Signal used as background signal in the calculations described below will be referred to as "background signal." The signal collected from the background control test site in a particular scan can be used as the background signal in the calculations described below for all test sites. In a particularly preferred embodiment, the background signal used in the calculation of signal from the label corresponding to mutant discriminator probes at screening test sites is the lowest signal detected at those test sites per suite.

To determine presence of signal from the amplification scans and from the screening test sites in the discriminator scans, the signal from each amplification control and/or each discriminator probe gathered from each scan is compared to the background signal gathered from that particular scan. The background signal from a particular scan will be subtracted from the RTSS gathered from each test site during a particular scan to calculate the "adjusted signal." For each scan of each patient test site, the background subtracted signal must be greater than a threshold value, which will be referred to as a "minimum signal criteria," in order to indicate the presence of a useful signal. In one embodiment, the minimum signal criteria is determined empirically.

In addition to the above calculation, the ratio of RTSS to background signal is calculated for each microlocation from each scan to give a "signal to noise ratio (SNR)." The SNR must be greater than a threshold value to indicate a readable signal. In one embodiment the SNR is determined empirically. In another embodiment, the threshold signal value for the SNR is set to a value of 5:1, which has been shown to be a meaningful setting to permit further processing.

Because it is known which blocker group, amplification controls, and discriminator probes were hybridized to each test site, once a useable signal is indicated by the above calculations the signal can be correlated to a particular patient, a particular amplicon, a particular screening variant group, a particular variant, or a particular heterozygous ratio reference based on from which test site and from which scan the signal was derived. Such correlation is described in more detail below.

Verifying Presence of Amplicons

In the amplification scans presence of signal at a particular test site indicates presence of a certain amplicon for a certain patient. For example, if two amplification controls (AC), AC-1 with a first label and AC-2 with a second label distinguishable from the first, were addressed to a first test site in each suite, detection of the first label at a first test site in a particular suite would indicate presence of the amplicon to which AC-1 hybridized for a particular patient. Similarly, presence of the second label at the first test site in a particular suite would indicate presence of the amplicon to which AC-2 specifically hybridizes. In this way, presence of each amplicon in a set for each patient can be analyzed. If absence of an amplicon for a certain patient is indicated by lack of signal, the discriminator scans for that patient are not analyzed and the assay must be performed again for that patient.

Presence of certain amplicons is also indicated by presence of signal from label corresponding to amplification controls at screening test sites in the discrimination scans.

Screening for Groups of Variants

Also in the discriminator scans, presence of signal corresponding to the label(s) associated with the mutant discriminator probes at a particular screening test site indicates presence of one of the variants in the screening variant group left unblocked at that test site. For example, if screening blocker mix D which left unblocked screening variant group D, was addressed to a first test site in each suite, then the presence of signal at the first test site in a particular suite would indicate presence of a mutation in one of the variants in screening variant group D in a particular patient sample.

Genotyping the Predominant Mutation

Usable signal from the genotyping test site and the heterozygous ratio reference test site must be manipulated further before presence of signal can be correlated with heterozygosity or homozygosity of a particular variant. In a preferred embodiment in which label one corresponds to the wild-type variant and label two to the mutant variant, a label one/label two scale factor, which will be referred to as a "multiplier," is calculated from the heterozygous ratio references, and will be applied to the signal gathered from the genotyping test site. This multiplier adjusts the lower of the label one or label two signals that correspond to the ratio references in such a way that after adjustment the signal from the wild-type ratio reference equals the signal from the mutant ratio reference.

In the discussion that follows, raw signal from which the background control reading from the appropriate scan has been subtracted will be referred to as adjusted signal. Raw signal from the ratio reference associated with label one will be referred to as "RR-1," while raw signal from the ratio references associated with label two will be referred to as "RR-2." Adjusted signal for RR-1 will be referred to as "ARR-1," while adjusted signal for RR-2 will be referred to as "ARR-2."

The multiplier will be calculated as follows. If ARR-1 is greater than or equal to ARR-2, then the multiplier for all label 1 adjusted signal will be one, while the multiplier for all label 2 adjusted signal will be ARR-1/ARR-2. If ARR-2 is greater than or equal to ARR-1, then the multiplier for all label 2 adjusted signal will be one, while the multiplier for all label 1 adjusted signal will be ARR-2/ARR-1.

The appropriate multiplier will then be multiplied to the adjusted signal from each genotyping test site from each scan (i.e., the scan to detect label one and the scan to detect label two). The resulting numbers will be referred to as "indicators." The indicator corresponding to label one at each genotyping test site will be referred to as I1, while the indicator corresponding to label two will be referred to as I2.

Finally, to correlate I1 and I2 from the genotyping test site to homozygosity for the predominant wild-type variant, heterozygosity, or homozygosity for the predominant mutation, I1 and I2 from each test site must be compared. If I1 is greater than I2* upper threshold factor (UTF), the patient is homozygous for the wild-type variant. If I2 is greater than I1* UTF, the patient is homozygous for the mutation. If I1 is less than I2* lower threshold factor (LTF) or I2 is less than I1* LTF, then the patient is heterozygous for this particular variant. If I1 is between the UTF and the LTF, then no determination as to heterozygosity or homozygosity can be made. In one embodiment the threshold factors are empirically determined. In another embodiment the UTF is 5 and the LTF is 2. In a preferred embodiment in which the microchip device is coupled to a computer system, these results (i.e., whether a particular patient is homozygous mutant, homozygous wild-type or heterozygous for a particular variant) are reported to the user by the computer.

In other embodiments in which more than two labels are used, such that more than one variant can be identified per genotyping test site, multiple heterozygous ratio references corresponding to the discriminator probes used to query the variants would be required. In addition, the reader would have to scan the chip multiple times in order to obtain readings from each label. Finally, the calculations and analysis outlined above would have to be done for each variant using the corresponding heterozygous ratio reference.

If no polymorphisms are detected at the screening test sites, the assay is complete as to the variants assayed at the screening test sites. In a preferred embodiment, if the assay is complete at this point, the computer system generates a report of the results of the assay. Referring to FIG. 1, in one embodiment, the reportable data are stored as a separate file, such as a database file or a text file. For example, the report can be downloaded to a report directory on storage device 107 and formatted for print or display by a database management system. In another embodiment, the report is created or formatted in a file suitable for viewing by display device 121, such as an HTML file within a browser. In still another embodiment, the report is stored in a format suitable for printing to a printer or archiving to a permanent archive, such as a tape storage device, compact disc, or microfiche.

If a polymorphism is detected at one or more screening test sites, a second run of hybridizations is needed to identify which of the polymorphisms in the known set is present in the sample. In addition, a second or third run of hybridization may be made to further identify the predominant mutation if its presence in the genome has been correlated to the presence of some other polymorphism of interest that also needs to be genotyped. In a preferred embodiment, the computer system creates a genotyping run protocol for each screening variant group identified as containing a polymorphism, and after a protocol is implemented, prompts the user as to which discriminator pairs should be added.

Genotyping Run

During the genotyping run, blocker mixes and heterozygous ratio references are electronically addressed to assigned, predetermined test sites. Thus, data from a particular test site can be correlated with a particular patient and the presence or absence of a particular member of a set of known polymorphisms determined.

In addition, discriminator pairs corresponding to one or more screening variant groups identified in the screening run as containing a mutation are loaded onto the microchip device to query the screening variant group. If the presence of a polymorphism in more than one screening variant group was identified at one or more test site suites in the screening run, more than one query will be needed. In that case, discriminator pairs for the polymorphisms in one screening variant group will be loaded and detected. Then, these discriminator probes will be removed, and another query performed using a set of discriminator pairs corresponding to the other screening variant group. As many queries as different screening variant groups identified as containing a polymorphism will be performed. If the same screening variant group was identified in multiple test site suites, only one query will be needed. Discriminators are labeled such that signal from labels at the various test sites is detected and analyzed to determine whether a sample is heterozygous, homozygous wild-type, or homozygous mutant.

Addressing the Array with Genotyping Blocker Groups and Heterozygous Ratio References After a positive reading in the screening run, the determination is made that a genotyping run is needed and that the mutation belongs to one or more screening variant groups. Accordingly, all of the probes are removed, leaving the single-stranded set of amplicons from each patient, the background control, and the heterozygous ratio reference for the predominant variant attached to their predetermined assigned test sites on the microchip device. The polynucleotide probes can be removed in a variety of ways, including thermal denaturation, chemical denaturation, or e-stripping. In a preferred embodiment, all probes are removed by washing the array with sodium hydroxide. Then, heterozygous ratio references and genotyping blockers are addressed to predetermined test sites.

Groups of heterozygous ratio references are then electronically addressed to predetermined test sites, with each group assigned to a different test site. The heterozygous ratio references can be attached to the permeation layer in a variety of ways, as is described in U.S. Pat. No. 6,051,380, which is incorporated herein by reference. In a particularly preferred embodiment, streptavidin is attached to the permeation layer of the microchip device, such that the streptavidin immobilizes the heterozygous ratio references, that have been biotinylated, thereby fixing them to the permeation layer.

The heterozygous ratio references are grouped such that each group contains the sequence of one of the variants in each screening variant group. Thus, if screening variant group A contains variants 1-3, screening variant group B contains variants 4-6, and screening variant group C contains variants 7-9, then heterozygous ratio reference group D contains the polynucleotide sequence of variants 1, 4, and 7, heterozygous ratio reference group E contains the sequence of variants 2, 6, and 8, and heterozygous ratio reference group F contains the sequence of variants 3, 6, and 9.

Each genotyping blocker mix is also electronically addressed to a predetermined test site in each suite. The blockers in each mix bind to the amplicon regions to which they are complementary so that, at each test site in a suite, one of the polymorphisms from each of the screening variant groups remain unhybridized. Thus, at each test site one variant from the screening variant group identified in the screening run can be queried. The relationship between the polymorphisms left unhybridized or unblocked at each test site during the screening run and during the genotyping run is set forth in Table 1 below, where A-Y represent different variants.

TABLE 1

| Test Site | Genotyping Pad 1 | Genotyping Pad 2 | Genotyping Pad 3 | Genotyping Pad 4 | Genotyping Pad 5 |
| --- | --- | --- | --- | --- | --- |
| Screening Pad 1 | A | B | C | D | E |
| Screening Pad 2 | F | G | H | I | J |
| Screening Pad 3 | K | L | M | N | O |
| Screening Pad 4 | P | Q | R | S | T |
| Screening Pad 5 | U | V | W | X | Y |

After the blockers have been addressed, the discriminator pairs that specifically bind to the variants in one screening variant group identified in the screening run as containing a polymorphism are loaded onto the microchip device. If, for example, signal was detected at test site 1 in one suite, revealing that the mutation corresponds to polymorphism 7, 8, or 9, then only the discriminator sets corresponding to these polymorphisms will be loaded onto the microchip device in this query. These discriminators are loaded onto the microchip device under stringent conditions conducive to specific binding of the discriminator probes to the regions of the amplicons containing the polymorphism to which the discriminator is complementary and to the heterozygous ratio references. In a preferred embodiment, the discriminator probes are hybridized by a method in which the microchip device is heated before and for a short period after the discriminator probes are added and then the temperature is slowly decreased. These temperature changes are followed by or performed in conjunction with several high salt washes to further increase specificity of discriminator probe binding.

As described above, these discriminators are associated with a label. In a preferred embodiment in which the universal reporter construct contains a label, after the discriminator probes and amplification controls have hybridized to the amplicons, the universal reporter is loaded onto the microchip device and specifically binds to the common sequence or tail of the discriminators. In a particularly preferred embodiment, before the discriminator probes are loaded onto the microchip device the universal reporters are mixed with the discriminator probes and specifically bind to the common sequence to which they are complementary.

After addition of the discriminator probes and, in some embodiments, universal reporters, a reader scans the microchip device, detecting the signal associated with the discriminators, with the background control, and with the heterozygous ratio references. The reader will perform one scan of the microchip device per number of different labels used in the assay. In a preferred embodiment in which fluorescent labels are used, each scan will detect a different wavelength of fluorescent light.

If polymorphisms were detected in more than one screening variant group, after scanning, the discriminator probes used in the first query will be denatured along with their labels to leave the blocker sequences hybridized. Denaturation can occur in a variety of ways, including thermal denaturation, chemical denaturation, and e-stripping. In a preferred embodiment the amplification controls are removed by thermal denaturation. Then, discriminator pairs specific for the polymorphisms in another variant group identified in the screening run are loaded onto the microchip device. The labeling and detection steps described above are repeated. Then, these discriminator probes may be removed and another set used to query another variant group, if necessary. As many queries as different screening variant groups identified in the screening run will be performed.

In a preferred embodiment at least some of the steps described above can be accomplished using a computer system coupled to the device in the manner described below. In a preferred embodiment, at least some of the steps described above are automated.

Analysis of Signal

The signal gathered from each scan of each query is then analyzed. The analysis outlined below may be performed by a computer integral to the microchip device. The following description describes analysis of data from one query in the genotyping run. Thus, the analysis will be repeated for each query performed in the genotyping run. To determine presence of signal, raw test site signal (RTSS) from each test site being genotyped, and from each heterozygous ratio reference test site, is compared to the background signal gathered from a particular scan. The background signal from a particular scan will be subtracted from the RTSS gathered from each test site during a particular scan to calculate the "adjusted signal." For each scan of each patient test site, the adjusted signal must be greater than a threshold value, which will be referred to as a "minimum signal criteria," in order to indicate the presence of a useful signal. This minimum signal criteria may be determined in the same ways as described above in the section regarding analysis of signal from the screening run. In addition to the above calculation, the ratio of RTSS to background signal is calculated for each test site from each scan to give a "signal to noise ratio." The SNR must be greater than a threshold value, which will be referred to as a "minimum ratio criteria" to indicate a readable signal. This minimum ratio criteria may be determined in the same ways as described above in the section regarding analysis of signal from the screening run. If absence of useful signal is reported in a suite, that patient sample must be retested. If absence of useful signal is reported for a heterozygous ratio reference, all of the samples on the chip must be retested.

For all of the test sites for which useful signal is generated, the adjusted signal from each test site is calibrated using a multiplier calculated from the signal from the test site with the corresponding heterozygous ratio reference (i.e., the heterozygous ratio reference that contains the same sequence as the variant being queried at a particular test site). In a preferred embodiment, in which a first label corresponds to the wild-type and second label to the polymorphism, a label one/label two scale factor, which will be referred to as a "multiplier," is calculated from each group of heterozygous ratio references. This multiplier adjusts the lower of the label one or label two signals that correspond to the ratio references in such a way that after adjustment the signal from the wild-type ratio reference equals the signal from the mutant ratio reference.

In the discussion that follows, raw signal from the ratio reference associated with label one will be referred to as "RR-1," while raw signal from the ratio references associated with label two will be referred to as "RR-2." Adjusted signal for RR-1 will be referred to as "ARR-1," while adjusted signal for RR-2 will be referred to as "ARR-2."

The multiplier will be calculated as follows. If ARR-1 is greater than or equal to ARR-2, then the multiplier for all label 1 adjusted signal will be one, while the multiplier for all label 2 adjusted signal will be ARR-1/ARR-2. If ARR-2 is greater than or equal to ARR-1, then the multiplier for all label 2 adjusted signal will be one, while the multiplier for all label 1 adjusted signal will be ARR-2/ARR-1.

The appropriate multiplier will then be multiplied to the adjusted signal from each test site for each scan (i.e., the scan to detect label one and the scan to detect label two). The resulting numbers will be referred to as "indicators." The indicator corresponding to label one at each test site will be referred to as I1, while the indicator corresponding to label two at each test site will be referred to as I2.

Finally, to correlate I1 and I2 from the genotyping test site to homozygosity for the predominant wild-type variant, heterozygosity, or homozygosity for the predominant mutant variant, I1 and I2 from each test site must be compared. If I1 is greater than I2* upper threshold factor (UTF), the patient is homozygous for the wild-type variant. If I2 is greater than I1* UTF, the patient is homozygous for the mutant variant. If I1 is less than I2* lower threshold factor (LTF) or I2 is less than I1* LTV, then the patient is heterozygous for this particular variant. If I1 is between the UTF and the LTF, then no determination as to heterozygosity or homozygosity can be made. In one embodiment the threshold factors are empirically determined. In another embodiment the UTF is 5 and the LTF is 2.

In other embodiments in which more than two labels are used, such that more than one polymorphism can be identified per test site, multiple heterozygous ratio references corresponding to the discriminator probes used to query the polymorphisms would be required to provide sufficient multipliers for each test site. In addition, the reader would have to scan the chip multiple times in order to obtain readings from each label. Finally, the calculations and analysis outlined above would have to be done for each variant detected at each test site using the corresponding heterozygous ratio reference.

In one embodiment, after the genotyping run the computer system generates a report of the results of the assay. In one embodiment, the reportable data is stored as a separate file, such as a database file or a text file. For example, the report can be downloaded to a report directory on storage device 107 and formatted for print or display by a database management system. In another embodiment, the report is created or formatted in a file suitable for viewing by display device 121, such as an HTML file within a browser. In still another embodiment, the report is stored in a format suitable for printing to a printer or archiving to a permanent archive, such as a tape storage device, compact disc, or microfiche.

Reflex Run

If a mutation is identified in either the screening or genotyping runs that is associated with another mutation or mutations, that associated mutation can be screened in a reflex run. For example, in cystic fibrosis, intron 8 possesses a regulatory element with a variable length thymidine tract (T-tract). A run of 5 T's on the same chromosome as a R117H mutation results in an altered phenotype. Thus, this T-tract mutation is analyzed if an R117H mutant is identified in a sample.

After it is determined that a reflex run is needed, all of the probes and blockers are removed, leaving the single-stranded set of amplicons from each patient, the background control, and the heterozygous ratio references at their predetermined assigned test sites. Polynucleotides can be removed in a variety of ways, including thermal denaturation, chemical denaturation, or e-stripping. In a preferred embodiment, all oligos are removed by washing the array with sodium hydroxide.

Heterozygous ratio references for the reflex variant are addressed to one test site in the same manner as described above for the other heterozygous ratio references. These heterozygous ratio references are complementary to the discriminator that specifically binds to the region of the amplicon containing the reflex variant. In a preferred embodiment the heterozygous ratio reference can be addressed to the same test site as the previously addressed heterozygous ratio references. In a particularly preferred embodiment, in which the predominant mutation is genotyped in the screening run, the heterozygous ratio references for the reflex run are addressed to the same test site at the same time as is the heterozygous ratio reference for the predominant mutation.

A pair of discriminator probes that binds to the reflex variant are loaded onto the microchip device under stringent conditions conducive to specific binding of the discriminator probes to sequence on the amplicon including reflex variants and to the heterozygous ratio references. In a preferred embodiment, the discriminators are hybridized by a touch down thermal method in which the microchip device is heated before and for a short period after the discriminator probes are added and then the temperature is slowly decreased. These temperature changes are followed by or performed in conjunction with several high salt washes to further increase specificity of discriminator binding.

As described above, these discriminator probes are associated with a label. In a preferred embodiment in which this label is a universal reporter, the universal reporter is loaded onto the microchip device after the discriminator probes are hybridized. In a particularly preferred embodiment, the universal reporters are mixed with the discriminator probes before the probes are loaded onto the microchip device. The discriminator probes are then detected and analyzed as described above in the genotyping run.

This reflex run can be modified to detect various types of mutations. For instance, with the T-tract reflex run described in the examples below, the T-tract variant has either the T5, T7, or T9 sequence. To determine which of the T-tracts a patient sample which is positive for the R117H mutation has and whether the patient is heterozygous, T5/T7 or T7/T9 or T5/T9 or homozygous, T5/T5, T7/T7, or T9/T9, the T5 and T7 variants are assayed and then they are removed and the T5 and T9 variants assayed. This specific embodiment will be described in detail in the examples below.

EXAMPLE 1

The following is a simplified example of the invention showing an assay of a genetic sample for 2 patients, and demonstrating the principle of the invention with 3 amplicons, 2 test sites, and blockers, discriminators, and universal reporters for only 4 polymorphisms.

Referring to FIG. 1, the example shows amplicons from a single patient 1, 2, 3, localized at test sites A-1 4 and A-2 5. The polymorphism interrogated is represented by (wild-type) and closed (mutant) circles, triangles, squares, and diamonds. In FIG. 1, the amplicons 1, 2, 3 from a first patient are already localized at test sites A-1 4 and A-2 5 while the amplicons of a second patient 6, 7, 8, 9, are in the process of being addressed to test sites B-1 10 and B-2 11. In this example, the patient whose amplicons are addressed at test sites at B-1 10 and B-2 11 is heterozygous for the mutation represented by the triangle.

Figure 2:
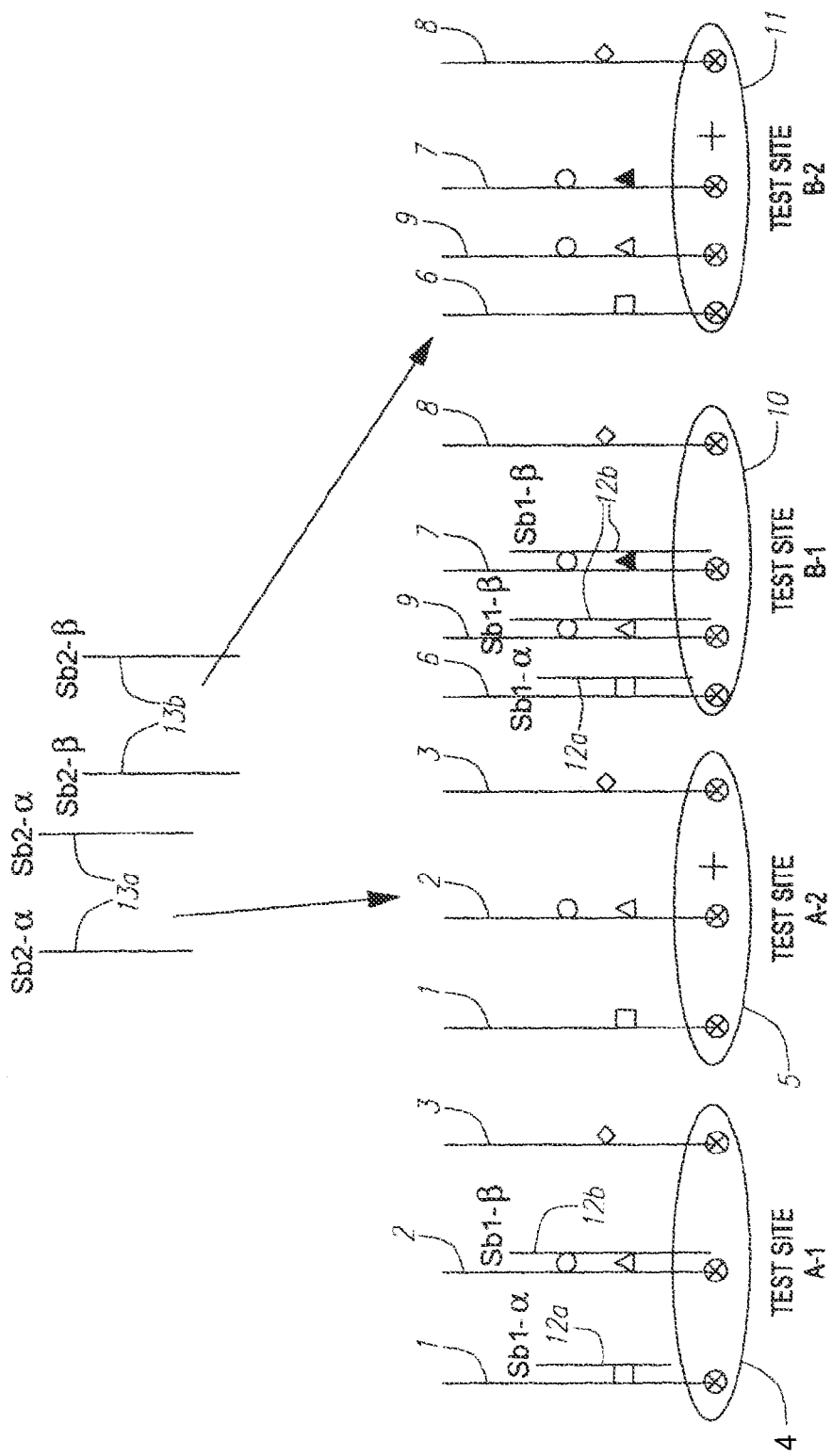
FIG. 2 is a schematic of the introduction of a first group of blockers to the amplicons at the test sites.

Referring to FIG. 2, groups of blockers are sequentially electronically addressed to each test site in test site specific groups. In the example of FIG. 2, the blocker group 12a, 12b specific for test sites A-1 4 and B-1 10, designed Sb2-α and Sb2-β respectively have been introduced and are specifically hybridized to the amplicons 1, 2, 3, at the identified loci. In this particular example, the blockers 12a, 12b, have hybridized to the locus comprising the square polymorphism and the locus comprising the circle and triangle polymorphisms. Referring to the test site B-1 10, the blockers 12a, 12b have specifically hybridized to both the wild-type and the mutant in the amplified patient sample. A second group of blockers 13a, 13b are specifically addressed to test sites A-2 5 and B-2 11. This group is designated Sb2-alpha and Sb2-beta to indicate a screening blocker mix specific for test sites A-2 5 and B-2 11 in this example and having individual blocker sequences corresponding to 2 identified loci (alpha, beta).

Figure 3:
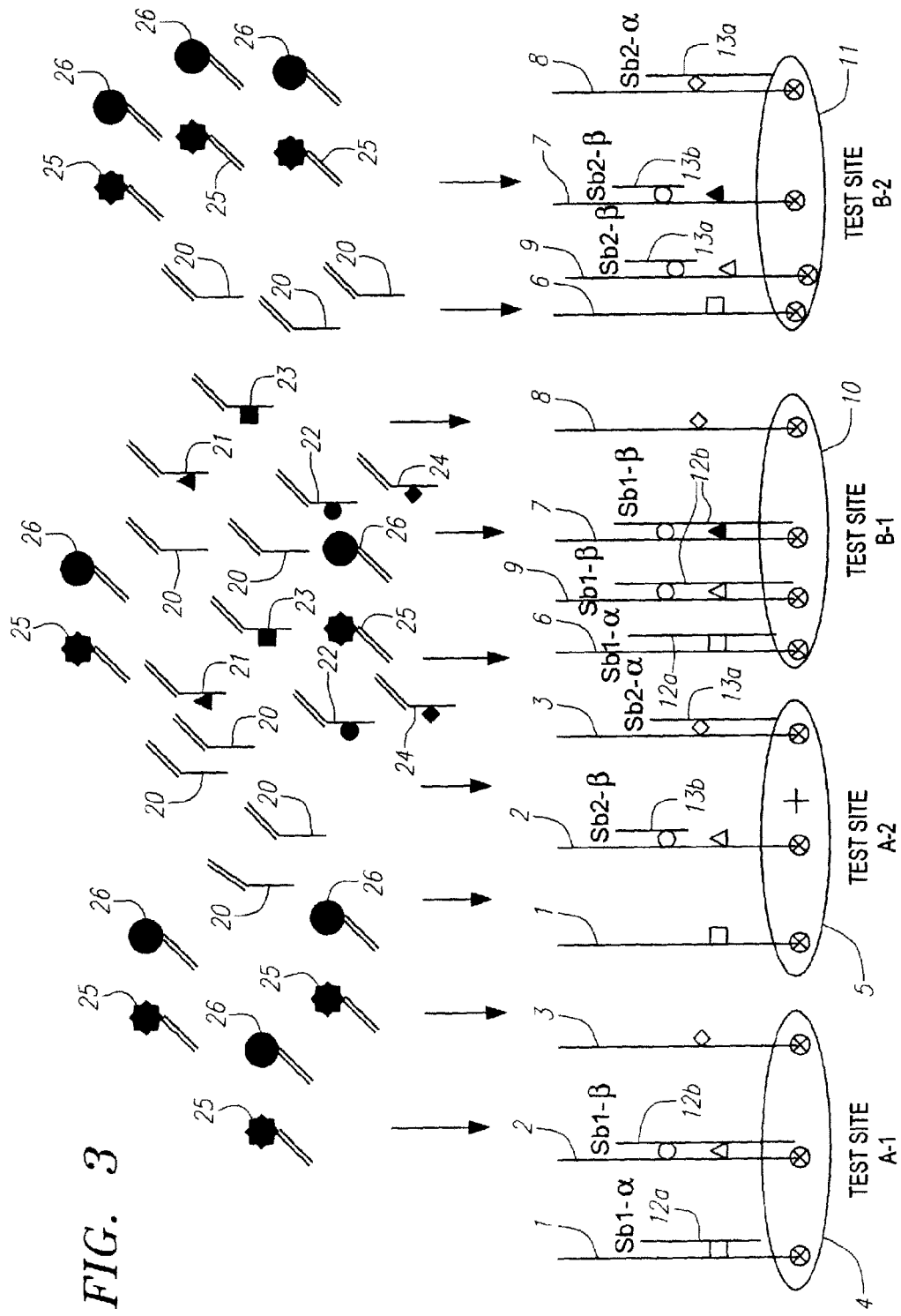
FIG. 3 shows the complete specific hybridization of both groups of blockers and the application of PCR control probes mutant discriminators and the first and second universal reporter.

Referring to FIG. 3, the hybridization of both groups of blockers 12a, 12b 13a, 13b is shown. Referring to test sites A-2 5 and B-2 11, the second group of blockers is specifically hybridized at the locus comprising the circle only and the locus comprising the diamond. FIG. 3 is a representation of the screening run showing the introduction of amplification control probes 20-1 to 20-9 complementary to specific amplicons of patient sample 1-9, mutant discriminator probes selective for the triangle, circle, square, and diamond 21, 22, 23, 24, and first and second universal reporters 25, 26. As described above, the discriminators are selective for the wild-type and mutant sequences in the amplicons but are prevented from hybridizing by the blockers specifically hybridized at the selected identified loci. The first universal reporter 25 and second universal reporter 26 have different labels (represented by the star-shaped and circle respectively) that yield different signals as described above. Although not shown in FIG. 3, wild-type discriminators would also be added to the mixture and would be selective for the wild-type sequences present in the amplicons. The amplification control run is omitted from this example.

Figure 4:
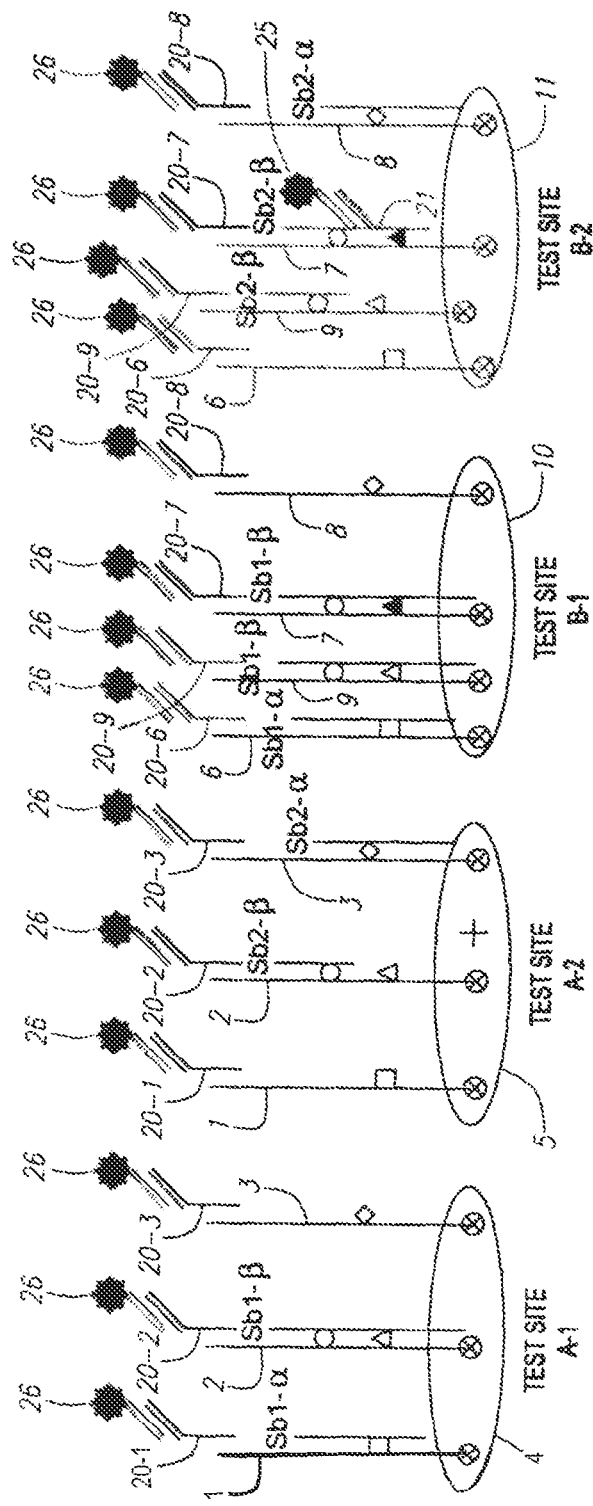
FIG. 4 shows the results of an example of a screening run wherein a confirmation of the amplification is provided by the second universal reporter and the presence of a mutation is indicated by the first universal reporter.

Referring to FIG. 4, the invention yields information from the selective binding of the mutant discriminators 21 at the identified loci not blocked by the specific hybridization of the blockers as indicated. Specifically, the signal from the first universal reporter 25 and second universal reporter 26 is measured to determine that the amplification has occurred and that a mutation is present in the patient sample. In this specific example, the signals generated by the universal reporters 25, 26 indicate that all three amplicons from both patients are present. The absence of any signal from the first universal reporter 25 on test sites A-1 4 or A-2 5 dedicated to the first patient indicates that no mutations are reported for this patient and the software program of the invention would recognize that the genotyping run need not be performed at test sites A-1 4 and A-2 5. With respect to test sites B-1 10 and B-2 11, the signal from the first universal reporter 25 indicates the presence of at least one mutation from amongst the first subset comprised of the square, triangle, circle, and diamond mutations. The software program would indicate that the genotyping run must be conducted on test sites B-1 10 and B-2 11 to determine whether the mutation is the triangle or square. The diamond and circle mutations are foreclosed by knowledge of the content of the blocker group 13a, 13b, applied to test site B-2 11 as opposed to test site B-1 10. To perform the genotyping run, the blockers and discriminators are stripped from the amplicons and a specific genotyping blocker group is introduced to test site B-1 10 and test site B-2 11.

Figure 5:
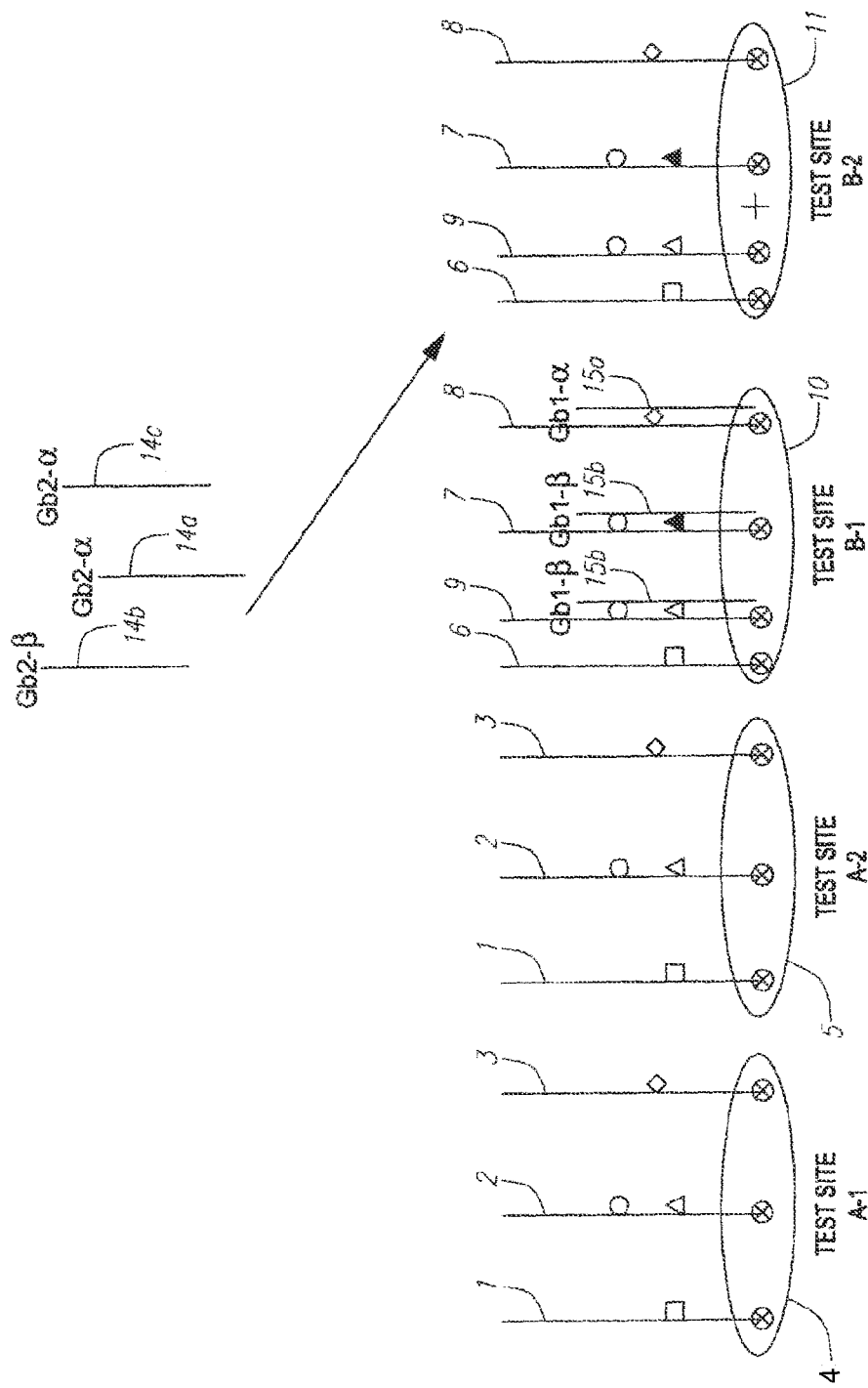
FIG. 5 is the strategic application of a first group of blockers in a genotyping run.

Referring to FIG. 5, a blocker group 15a, 15b, 15c designated as G1α-β is introduced to the test site B-1 10 and a second group of genotype blockers, designated Gb-2α, β, λ are introduced to test site B-2 11. In this example, the blockers at test site B-1 10, specifically hybridize to the identified loci containing the circle and triangle and the diamond polymorphisms. The second group of blockers 14a, 14b, 14c addressed to site B-2, specifically hybridize to the circle polymorphism only and the diamond polymorphism as shown in FIG. 6.

Figure 6:
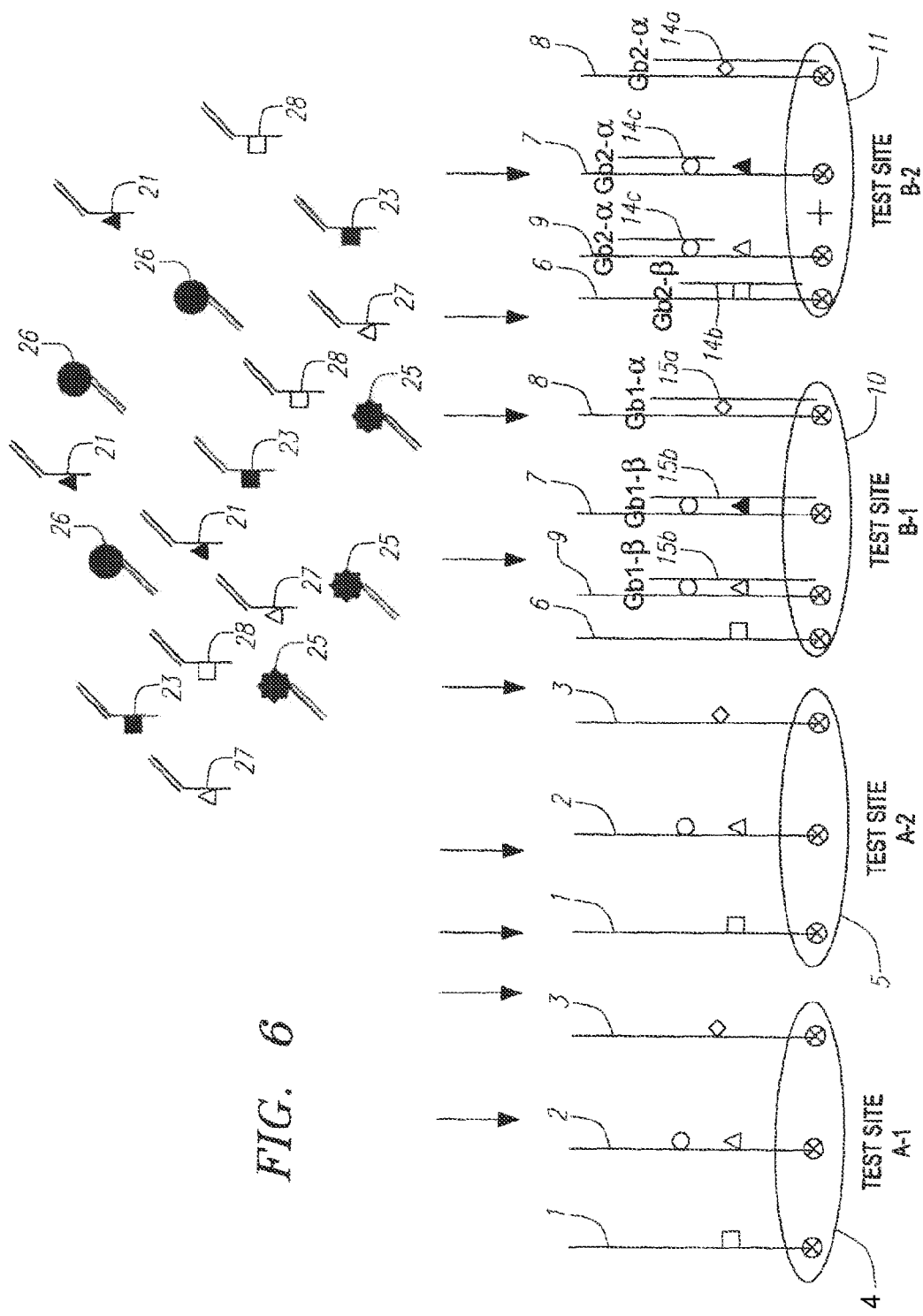
FIG. 6 shows the specific hybridization of two blocker groups in a genotyping run together with the application of mutant and wild-type discriminators and the first and second universal reporters.

Referring specifically to FIG. 6, test site B-1 10 shows that the blocker groups 14a, 14b, 14c have specifically hybridized to each mutation except for the square. Analogously, at test site B-2 11, the blockers have specifically hybridized to each mutation except for the triangle. This strategy interrogates the two polymorphisms that could possibly have resulted in the signal generated at test site B-2 in the screening run. The application of mutant discriminators 21, 23 and wild-type discriminators 27, 28 for the triangle and square polymorphisms together with the first universal reporter 25 and second universal reporter 26 specifically identify the mutation in the sample of the second patient.

Figure 7:
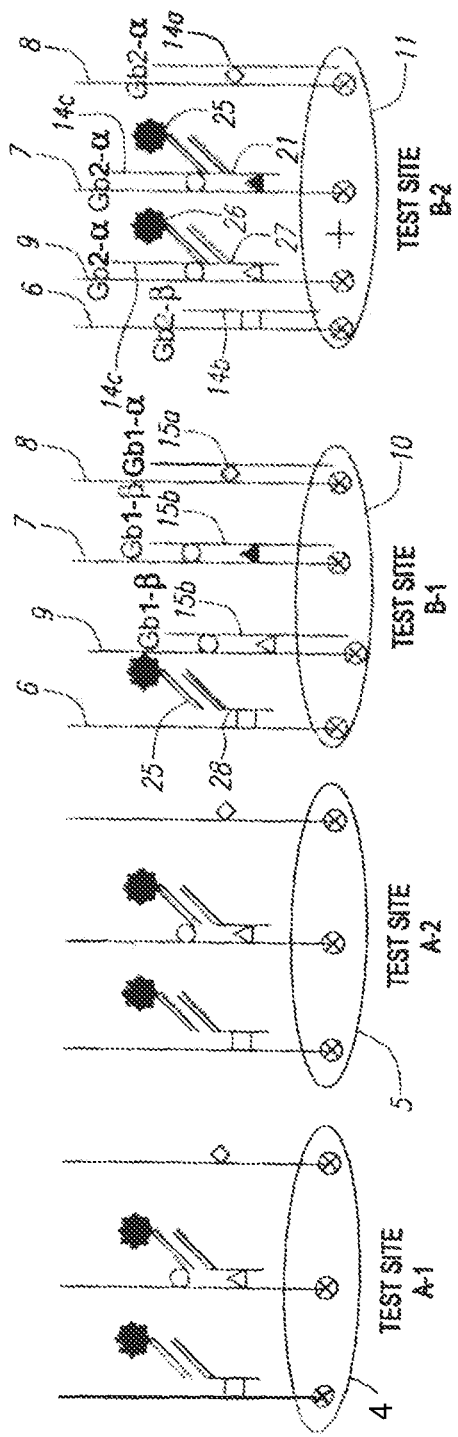
FIG. 7 shows the results of a genotyping run wherein first and second groups of blockers are specifically hybridized to the amplicons and the hybridization of the discriminators and the first and second universal reporters indicate a heterozygous mutation in the sample from an individual patient.

Referring to FIG. 7, the labels of the first universal reporter 25 and second universal reporter 26 are indicative that the second patient's sample contains the wild-type sequence of the square mutation and a mutant of the triangle. Because both the first universal reporter 25 and second universal reporters 26 generate a signal at test site B-2 11, the assay indicates that the patient is heterozygous for the triangle mutation.

EXAMPLE 2

Using the system, apparatus, reagents and methods described above, Applicants detected the cystic fibrosis-related mutations set forth in Table 2 below. These mutations are those that the American College of Gynecologists (ACOG) has recommended for testing in couples planning to have children.

TABLE 2

CF Mutation Panel

| Mutation | Relevant References |
|---|---|
| G 85 E | Tsui 6,001,588 |
| R 117 H | (1990) Dean, M, Cell 61: 863-870 |
| I 148 T | (1994) Bozon D, Hum. Mut. 3: 330-332 |
| R 334 W | (1991) Gasparini P, Genomics, 10: 193-200 |
| R 347 P | (1990) Dean, M, Cell 61: 863-870 |
| A 455 E | Tsui 6,001,588 |
| ΔF 508 | Tsui 5,776,677 |
| ΔI 507 | Tsui 6,001,588 |
| G 542 X | Tsui 6,001,588 |
| G 551 D | Cutting 5,407,796 |
| R 553 X | Cutting 5,407,796 |
| R 560 T | Tsui 6,001,588 |
| R 1162 X | (1991) Gasparini P, Genomics, 10: 193-200 |
| W 1282 X | (1990) Vidaud M, Hum Genet., 85: 446-449 |
| N 1303 K | (1991) Osborne L, Am J. Hum Genet. 48: 608-612 |
| 621 + 1G→T | Tsui 6,001,588 |
| 711 + 1G→T | Tsui 6,001,588 |
| 1078 delT | (1992) Claustres M Genomics, 13: 907-908 |
| 1717 − 1G→A | Tsui 6,001,588 |
| 1898 + 1G→A | (1990) Guillermit H Hum Genet. 85(4): 450-453 |
| 2184 delA | 2183 AA → G (1994) Bozon D, Hum. Mut. 3: 330-332 |

TABLE 2-continued

CF Mutation Panel

| Mutation | Relevant References |
|---|---|
| 2789 + 5G→A | (1993) Ferec C Hum Mol. Genet. 2(10): 1557-60 |
| 3120 + 1G→A | (1996) Bienvenu Hum Hered 46(3): 168-71 |
| 3659 delC | Tsui 6,001,588 |
| 3849 + 10kbC→T | (1994) Highsmith WE, New Engl. J Med. 331: 974-980 |
| Reflex test 5T/7T/9T* | (1997) Friedman KJ Hum Mut 10: 108-115 |

*5T in cis can modify R117H phenotype or alone can contribute to congenital bilateral absence of vas deferens (CBAVD); in the standard assay 5T analysis is performed only as a reflex test for R117H positives, but the user may choose to enable the reflex test upon positive results for any or all other mutations.

Amplification of the Chromosome Regions Related to Cystic Fibrosis

Two multiplex polymerase chain reactions were performed to amplify portions of the human genome that include one or more cystic fibrosis mutations using standard techniques well known in the art. The exons and introns amplified and the polymorphisms corresponding to each mutation are set forth in Table 3 below. Exons 3, 4, 9, 11, 12, and 21 were amplified in polymerase chain reaction one. Exons 5, 7, 10, 13, 14b, 16, 19, 20 and Intron 19 were amplified in polymerase chain reaction two.

The contents of each reaction are set forth in Table 4 below, and the primers, biotinylated and non-biotinylated, are set forth in Tables 5 and 6. Primers were ordered from Integrated DNA Technologies, Inc. (Coralville, Iowa) The temperature cycling parameters for the reactions were 96° C. for 10 minutes, followed by 35 cycles of 95° C. for 30 seconds, 55° C. for 1 minute, 72° C. for 2 minutes, followed by 72° C. for 7 minutes, followed by a 4° C. hold. After amplification the two reactions were mixed and then desalted using Millipore plates. Samples were recovered in 50 mM histidine.

TABLE 3

Exons/Intron and Related Mutations

| Exon/Intron | Related Mutation(s) |
|---|---|
| Exon 3 | G85E |
| Exon 4 | 621 + 1(G > T), R117H, I148T |
| Exon 5 | 711 + 1(G > T) |
| Exon 7 | R334W, 1078delT, R347P |
| Exon 9 | A455E |
| Exon 10 | ΔI507, ΔF508 |
| Exon 11 | G542X, 1717 − 1(G > A), G551D, R560T, R553X |
| Exon 12 | 1898 + 1(G > A) |
| Exon 13 | 2184delA |
| Exon 14b | 2789 + 5(G > T) |
| Exon 16 | 3120 + 1(G > A) |
| Exon 19 | 3659delC, R1162X |
| Intron 19 | 3849 + 10kb(C > T) |
| Exon 20 | W1282X |
| Exon | N1303K |

TABLE 4

Content of Multiplex PCRs

| | 9 plex Volume (uL) per Rxn | 6 plex Volume (uL) per Rxn |
|---|---|---|
| 10X Taq buffer | 5 | 5 |
| MgCl$_2$ (25 mM) w/Taq | 9 | 9 |

TABLE 4-continued

Content of Multiplex PCRs

| | 9 plex<br>Volume (uL) per Rxn | 6 plex<br>Volume (uL) per Rxn |
|---|---|---|
| rgt | | |
| dNTPs (10 mM ea) | 3 | 3 |
| AmpliTaq Gold Enz | 1 | 1 |
| H2O | 28.5 | 28.5 |
| Template (100 ng/uL) | 0.5 | 0.5 |
| Primer volume total | 3 | 3 |
| Total | 50 | 50 |
| Primer concentrations | E10, 20, I19, E19 = 100 nM each<br>E5, 7, 13, 14 = 200 nM each<br>E16 = 300 nM each | E3, 12, 21 = 200 nM each<br>E9, 11, 4 = 300 nM each |

TABLE 5

Biotinylated Primers

1. Exon 11   5'biotin-TCAACTGTGGTTAAAGCAATAGTGTGATA-3' SEQ ID NO: 1
2. Exon 4    5'biotin-TTTATCCCTTACTTGTACCAGCTCACTACCTAA-3' SEQ ID NO: 2
3. Exon 21   5'biotin-TTCACAAGGGACTCCAAATATTGCTGTAG-3' SEQ ID NO: 3
4. Exon 7    5'biotin-ATTATGGTACATTACCTGTATTTTGTTTATTG3' SEQ ID NO: 4
5. Exon 10   5'biotin-GATGGGTTTTATTTCCAGACTTCACTTCTAATG3' SEQ ID NO: 5
6. Exon 19   5'biotin-AATTGTGAAATTGTCTGCCATTCTT3' SEQ ID NO: 6
7. Exon 16   5'biotin-GATATAGCAATTTTGGATGACCTTCTG3' SEQ ID NO: 7
8. Exon 20   5'biotin-AATATAATTTAGTTGCCTTTTTTCTGGCTAAGTCC3' SEQ ID NO: 8
9. Exon 12   5'biotin-TCAAGAGGTAAAATGCAATCTATGATG3' SEQ ID NO: 9
10. Exon 13  5'biotin-TGTCTGTAAACTGATGGCTAACAAAACTA3' SEQ ID NO: 10
11. Exon 14b 5'biotin-CACTACCATAATGCTTGGGAGAAAT3' SEQ ID NO: 11
12. Exon 3   5'biotin-ATGCAACTTATTGGTCCCACTTTTT3' SEQ ID NO: 12
13. Exon 5   5'biotin-TGTCAAGCCGTGTTCTAGATAAAATAAG3' SEQ ID NO: 13
14. Intron 19 5'biotin-GTTAAACAGTGTTGAATTTGGTGCTA3' SEQ ID NO: 14
15. Exon 9   5'biotin-AAGAACTACCTTGCCTGCTCCAG3' SEQ ID NO: 15

TABLE 6

Non-Biotinylated Primers

1. Exon 11   5'CAGAAACAGAATATAAAGCAATAGAGAAATG3' SEQ ID NO: 16
2. Exon 4    5'TCACCAAAGCAGTACAGCCTCTCTTA3' SEQ ID NO: 17
3. Exon 21   5'CCATATTTCTTGATCACTCCACTGTT3' SEQ ID NO: 18
4. Exon 7    5'CAGAACTGAAACTGACTCGGAAGG3' SEQ ID NO: 19
5. Exon 10   5'ATATAATTTGGGTAGTGTGAAGGGTT3' SEQ ID NO: 20
6. Exon 19   5'CCCTGAGGGCCAGATGTCA3' SEQ ID NO: 21
7. Exon 20   5'CCTATATGTCACAGAAGTGATCCCATC3' SEQ ID NO: 22
8. Exon 12   5'GAACTGTTTAAGGCAAATCATCTACAC3' SEQ ID NO: 23
9. Exon 13   5'TTCCCCAAACTCTCCAGTCT3' SEQ ID NO: 24
10. Exon 14b 5'AGGTGAAGATGTTAGAAAAAAAATCAACT3' SEQ ID NO: 25
11. Exon 3   5'CACAAAAATGCATATAGTTATGTGATACA3' SEQ ID NO: 26
12. Exon 5   5'AACTCCGCCTTTCCAGTTGTATAAT3' SEQ ID NO: 27

TABLE 6-continued

Non-Biotinylated Primers

13. Intron 19 5'GACTTGTCATCTTGATTTCTGGAGAC3' SEQ ID NO: 28

14. Exon 9    5'AGATCATGTCCTCTAGAAACCGTATGCTATA3' SEQ ID NO: 29

15. Exon 16   5'TCACATTTGCTTTTGTTATTGTTTTTTTA3' SEQ ID NO: 30

The Apparatus

All of the following steps were performed on a Molecular Biology workstation (MBW) comprising the NanoChip® from Nanogen Corporation. The MBW contained both a reader and a loader which were coupled together directly. The QNet protocol was used to permit communication between the reader and the loader.

The reader was coupled to a personal computer (PC) for data processing. The reader uploads and downloads MBW data directly to the computer. However, the system is equipped to handle data uploads and downloads over a network interface, such as a packet-switched local area network. File transfer between the reader and the PC uses the file transfer protocol (FTP), over a network that supports the transmission control protocol/Internet protocol (TCP/IP) suite. In this case, the reader functioned as the FTP host, and the PC functioned as the client, initiating file transfers.

The reader received its protocol and the loader's protocol from the PC and stored the protocols on the reader's storage device. The reader is responsible for sending and receiving data to and from the loader. Reader and loader data gathered during processing was collected by the reader and uploaded to the PC in preparation for further data analysis, processing, and reporting by the PC. The PC ran an automated software module (ASM) that performed the data analysis, processing, and reporting derived from the data uploaded from the reader. Data analysis included the signal analysis steps described in the screening and genotyping run headings of this example. The automated software module also generated the system reports that the system operator can use to analyze assay results. The automated software module was also responsible for downloading the reader and loader protocols to the MBW.

The reader used for the assaying methods described herein housed a main board with 128 megabytes of system memory and accommodated at least 10 gigabytes of permanent storage. The on-board processor controlling the operation of the reader was a 400 MHz Intel Pentium II. The loader used for the assaying methods described herein housed a main board with 32 megabytes of system memory and 16 megabytes of flash-type permanent storage. The on-board processor controlling the operation of the loader was a 50 MHz Intel i386. The operating system running on both the reader and the loader was the QNX operating system. These components represent the minimum reader and loader hardware and software specification suggested for optimal operation of the assay management application.

Assay Overview

Set-Up

Up to 15 patient samples were assayed on one microchip for 25 markers for CF set forth in the chart above. The assay included amplification verification, a screening run, a genotyping run, and a reflex run. The sequence of the discriminator probes used to query each variant and referred to throughout this example are set forth at the end of the example. The sequences of the blocker groups are set forth at the end of this example.

In this example, amplification verification was chosen and a reflex run was performed upon detection of mutations besides R117H. First, the full set of amplicons from up to 15 patients was electronically addressed to six test sites on the chip. The user added to particular places on the loader 1) a 96 well plate containing the de-salted amplicons from up to 15 patients and 2) the 10-well screening reagent pack, which contained the reagents set forth in Table 7. The user then implemented the loader protocol, the steps of which are set forth below.

TABLE 7

Screening Reagent Pack

| Well | Reagent | Description of Reagent |
|---|---|---|
| 1 | Blocker Group A1 | All blocked except 621 + 1(G > T), G542X, 1898 + 1(G > A), 2184delA, 3849 + 10kb(C > T) |
| 2 | Blocker Group A2 | All blocked except R334W, ΔI507, 1717 – 1(G > A), 3659delC, N1303K |
| 3 | Blocker Group A3 | All blocked except R117H, 1078delT, G551D, R1162X |
| 4 | Blocker Group A4 | All blocked except G85E, I148T, 711 + 1(G > T), A455E, R560T |
| 5 | Blocker Group A5 | All blocked except R347P, R553X, 2789 + 5(G > A), 3120 + 1(G > A), W1282X |
| 6 | Blocker Group A6 | All blocked except [[☐]]ΔF508 |
| 7 | ΔF508 Ratio Reference & T-tract Ratio References | |
| 8 | Empty | |
| 9 | ¼ low salt buffer | |
| 10 | ¼ low salt buffer | |

The loader 1) loaded the amplicons, the ΔF508 Ratio Reference & T-tract Ratio References, and the histidine background control onto predetermined test sites on a particular chip and 2) electronically addressed each to the assigned test site. Specifically, amplicons from each patient were addressed to six non-adjacent test sites. The ratio references were addressed to one of the seven test sites at the bottom of each chip that are reserved for the various ratio references and controls and a histidine buffer was applied to another of test site at the bottom of the chip. Finally, the system directed denaturation of the amplicons by adding ¼ low salt buffer to the chip and by e-stripping the amplicons to render them single stranded. Specifically, the loader introduced ¼ low salt buffer to the chip and e-stripped 45 of the 90 test sites used for sample addressing in a checkerboard pattern using an amplitude of −1.4V for 60 seconds. Then, the loader e-stripped the remaining 45 microlocations in the same manner.

Screening Run

PCR Amplification Verification, Screening, dF508 Genotyping

Next the loader directed the electronic addressing of the blocker mixes set forth in table 7 above. Each blocker group A1-A6 was addressed to the corresponding predetermined microlocation, 1-6, in each microlocation suite.

Because the user had chosen to include amplification verification in the assay, the user then manually added to each chip the amplification controls mix, which contained a high salt mix of 1) the amplification controls that specifically bind to exons 5, 7, 9, 12, 13, 14b, 19, and 20, 21 and 2) universal reporters. Two universal reporters, coupled to red and green fluorescent labels, Alexa Fluor® 532 (red) and Alexa Fluor® 647 (green), were used throughout this assay. The Alexa labels were purchased from Molecular Probes, Inc. (Eugene, Oreg.). See Table 8 below for the sequences of the universal reporters and the labels with which each is associated.

TABLE 8

Universal Reporters

| | |
|---|---|
| Universal Reporter, Red | 5'ctcaatgttcggactcag-Alexa Fluor 532-3' SEQ ID NO: 31 |
| Universal Reporter, Green | 5'tgtcaagcgatatactgc-Alexa Fluor 647-3' SEQ ID NO: 32 |

The amplification controls for exons 12, 21, 7, 9, and 14b were designed to bind to the red universal reporter, while the amplification controls for exons 13, 19, 5, and 20 were designed to bind to the green universal reporter. These amplification controls were wild-type discriminators with tails complementary to one of the universal reporters, as shown in the table below. Although generally in this assay red universal reporters bind to mutant variants and green universal reporters bind to wild-type variants, in this amplification control run some of these discriminators bound to the red universal reporter and some to the green universal reporter so that two amplicons could be detected per test site, as shown in Table 9 below.

TABLE 9

Amplification Controls Used in First Amplicon Verification Scan

| Exon Detected: | Micro-location | Wild-Type Discriminator For: | Universal Reporter to which Tail Is Complementary |
|---|---|---|---|
| 12 | 1 | 1898 + 1(G > A) | Red |
| 13 | 1 | 2184delA | Green |
| 21 | 2 | N1303 | Red |
| 19 | 2 | 3659delC | Green |
| 7 | 3 | 1078delT | Red |
| 9 | 4 | A455E | Red |
| 5 | 4 | 711 + 1(G > T) | Green |
| 14B | 5 | 2789 + 5(G > A) | Red |
| 20 | 5 | W1282X | Green |

After adding the amplification control mix, the user placed the microchip(s) onto the reader and implemented the following reader protocol. To promote hybridization and to remove unhybridized amplification controls, the reader automatically increased the temperature of the chip to 56° C. for 60 seconds, decreased the temperature of the chip to 40° C. for 30 seconds, and then performed eight high salt washes of the chip. Next, the reader performed scans of the test sites to which samples had been addressed and to which the background control was addressed—one to detect red label and one to detect green label—and offloaded the data collected to the PC.

The amplification controls were then removed. The reader automatically increased the temperature of the chip to 56° C., performed 3 high salt washes, and then lowered the temperature of the chip to 24° C. This temperature increase caused denaturation of the amplification controls but allowed the blocker sequences to remain hybridized.

Next, the user added to each microchip a screening reporter mix, which was a reagent mix in high salt containing 1) mutant discriminator probes for all of the variants queried 2) wild-type discriminator probes for ΔF508, 3) amplification controls that specifically bind to exons 3, 4, 10, 11, 16, and intron 19, (i.e., wild-type discriminator probes that bind specifically to the above exons) and 4) red and green universal reporters. In this portion of the assay, red universal reporters were bound specifically to mutant variants and green universal reporters were bound specifically to wild-type variants. The user then implemented the following reader protocol.

The reader increased the temperature of the chip to 56° C. for 60 seconds, decreased the temperature to 42° C. for 30 seconds, performed 8 high salt washes, and lowered the temperature to 24° C. The reader then performed two discriminator scans (to detect red and green label) of the test sites to which the samples, the background control, and the dF508 heterozygous ratio reference had been addressed and offloaded this data to the PC.

The ASM then analyzed the data collected from the test sites. The ASM calculated an adjusted signal and a signal to noise ratio for data gathered from each test site for each scan. The reading from the test site to which the histidine control was addressed was used as background signal for calculating adjusted signal for the amplification control readings from the first set of scans and for all of the dF508 readings (from test site 6 of each suite and from the test site with the dF508 heterozygous ratio reference). In contrast, to analyze the readings from test sites 1-5 in each suite, the lowest reading from all of the test sites in a suite was used as the background signal. For signal from each test site to be considered usable, the adjusted signal (raw test site signal (RTSS) minus background signal) had to be greater than 50, and the signal to noise ratio had to be greater than five for all signal except that from test sites 1-5, where the signal to noise ratio had to be greater than two.

The signal from each test site from the amplification scan was analyzed as follows. If any signal failed to meet the above criteria, the system reported, in a final report that was generated after all necessary runs had been completed, which PCR product failed in which suite and that the corresponding sample required a retest. Neither screening nor genotyping results were reported for any suite that had any failed PCR. Usable signal at each test site was analyzed as follows:

Exon12 presence indicated by RED on 1. If no RED signal, then there must be a RED signal on 1 in the subsequent screen run and the genotype for 1898+1(G>A) must be homozygous mutant.

Exon13 presence indicated by GREEN on 1. If no GREEN signal, then there must be a RED signal on 1 in the subsequent screen run and the genotype for 2184delA must be homozygous mutant.

Exon21 presence indicated by RED on 2. If no RED signal, then there must be a RED signal on 2 in the subsequent screen run and the genotype for N1303K must be homozygous mutant.

Exon19 presence indicated by GREEN on 2. If no GREEN signal, then there must be a RED signal on 2 in the subsequent screen run and the genotype for 3659delC must be homozygous mutant.

Exon7 presence indicated by RED on 3. If no RED signal, then there must be a RED signal on 3 in the subsequent screen run and the genotype for 1078delT must be homozygous mutant.

Exon9/Intron9 presence indicated by RED on 4. If no RED signal, then there must be a RED signal on 4 in the subsequent screen run and the genotype for A455E must be homozygous mutant.

Exon5/Intron5 presence indicated by GREEN on 4. If no GREEN signal, then there must be a RED signal on 4 in the subsequent screen run and the genotype for 711+1(G>T) must be homozygous mutant.

Exon14B presence indicated by RED on 5. If no RED signal, then there must be a RED signal on 5 in the subsequent screen run and the genotype for 2789+5(G>A) must be homozygous mutant.

Exon20 presence indicated by GREEN on 5. If no GREEN signal, then there must be a RED signal on 5 in the subsequent screen run and the genotype for W1282X must be homozygous mutant.

The various signals from the discriminator scan were also analyzed. First, presence of amplicons was analyzed by analysis of the signal from the red and green scans. If any signal failed to meet the above criteria, the ASM reported, in the final report, which PCR product in which suite failed and that the corresponding sample required a retest. Neither screening nor genotyping results were reported for any suite that had any failed PCR. Usable signal was analyzed as follows:

Intron19 presence indicated by GREEN or RED on 1. If using RED to indicate presence, the genotype for 3849+10 kb(C>T) must be homozygous mutant.

Exon11 presence indicated by GREEN or RED on 2. If using RED to indicate presence, the genotype for 1717-1(G>A) must be homozygous mutant.

Exon4 presence indicated by GREEN or RED on 3. If using RED to indicate presence, the genotype for R117H must be homozygous mutant.

Exon3 presence indicated by GREEN or RED on 4. If using RED to indicate presence, the genotype for G85E must be homozygous mutant.

Exon16/Intron16 presence indicated by GREEN or RED on 5. If using RED to indicate presence, the genotype for 3120+1(G>A) must be homozygous mutant.

Exon10 presence indicated by GREEN or RED on 6.

The ASM reported these results in the final report.

To determine presence of the various screening variant groups the data from the red scan was analyzed as follows. If the signal from a particular microlocation did not meet the minimum signal criteria or signal to noise criteria, the ASM discontinued analysis of the suite to which the test site belonged and reported, in the final report, "no designation" for that patient sample and that the sample required a retest. Usable signal was analyzed as follows.

621+1(G>T), G542X, 1898+1(G>A), 2184delA, 3849+10 kb(C>T) screening variant group indicated by RED on 1

R334W, ΔI507, 1717-1(G>A), 3659delC, N1303K screening variant group indicated by RED on 2

R117H, 1078delT, G551D, R1162X screening variant group indicated by RED on 3

G85E, I148T, 711+1(G>T), A455E, R560T screening variant group indicated by RED on 4

R347P, R553X, 2789+5(G>A), 3120+1(G>A), W1282X variant screening group indicated by RED on 5

The ASM reported presence of a particular screening variant group at a particular test site in a final report. If three or more mutations were detected for a single sample in the screening run, the system reported the following warning: "Alert: Three or more mutations indicated for sample X. This sample should be repeated for confirmation."

To genotype the dF508 variant, signal from the red and green scans of test site six in each suite and from the dF508 heterozygous ratio reference test site was analyzed. If the signal from a particular suite did not meet the minimum signal criteria or signal to noise criteria, the ASM discontinued analysis of that suite and, in the final report, reported "no designation" for that patient sample for dF508 and that the sample required a retest. And if the signal from the heterozygous ratio reference test site did not meet the minimum signal criteria or signal to noise criteria, the ASM discontinued analysis of all dF508 test sites on that chip and reported the failure and that a retest was required in the final report.

To convert the signal from the dF508 test sites in each suite to genotyping data, a multiplier was calculated as described in the detailed description above, using the red scan data and the green scan data from the test site to which the heterozygous ratio reference corresponding to the dF508 variant was addressed. If the adjusted red signal was greater than the adjusted green signal at the heterozygous ratio reference test site, the multiplier for red signal from the dF508 test site was 1, and the multiplier for all green signal was adjusted red signal/adjusted green signal; if the green signal was greater than the red signal, the multiplier for green signal was 1, and the multiplier for red signal was adjusted green signal/adjusted red signal. All signals from each dF508 test site in each suite were multiplied by the appropriate multiplier (i.e., signal from the red scan is multiplied by the red multiplier and signal from the green scan is multiplied by the green multiplier) to obtain an indicator. By comparing the indicators as follows, the following determinations could be made for each dF508 test site:

Red indicator to green indicator ratio is greater than 5:1 indicates a mutant (homozygous) genotype.

Green indicator to red indicator ratio is greater than 5:1, indicates a wild-type (homozygous) genotype.

Red indicator to green indicator ratio is less than 2:1 OR the green indicator to red indicator ratio is less than 2:1 indicates a heterozygous mutant.

If red indicator to green indicator ratio is between 2:1 and 5:1 OR the green indicator to red indicator ratio is between 2:1 and 5:1, no designation can be made.

The ASM reported "mutant," "wild-type," "heterozygote," or "no designation" for each dF508 test site in the final report.

If no mutations were indicated at any of the screening test sites, the analysis was complete and the ASM generated the final report. If one or more mutations were detected, the ASM created the necessary protocol(s) for genotyping. The protocols, which could be run in any order, were displayed on the PC monitor. When a user selected a protocol to run, the ASM prompted the user as to which microchip and discriminator mix to use. When the user finished running one protocol, the cartridge was ejected and a "complete" icon displayed next to that protocol. The user then selected one of the remaining protocols. The variants genotyped in each protocol depend on which microlocation contained a mutant in the screening run. This relationship is set forth below.

Test Site 1 Positive in Screen
3849+10 kb(C>T) genotyped at test site 1
G542X genotyped at test site 2

1898+1(G>A) genotyped at test site 3
2184delA genotyped at test site 4
621+1(G>T) genotyped at test site 5
Test Site 2 Positive in Screen
ΔI507 genotyped at test site 1
1717-1(G>A) genotyped at test site 2
R334W genotyped at test site 3
3659delC genotyped at test site 4
N1303K genotyped at test site 5
Test Site 3 Positive in Screen
Test site 1 NOT SCANNED
G551D genotyped at test site 2
1078delT genotyped at test site 3
R1162X genotyped at test site 4
R117H genotyped at test site 5
Test Site 4 Positive in Screen
G85E genotyped at test site 1
R560T genotyped at test site 2
A455E genotyped at test site 3
711+1(G>T) genotyped at test site 4
I148T genotyped at test site 5
Test Site 5 Positive in Screen
3120+1(G>A) genotyped at test site 1
R553X genotyped at test site 2
R347P genotyped at test site 3
2789+5(G>A) genotyped at test site 4
W1282X genotyped at test site 5

Genotyping Run

The user selected one of the protocols displayed on the monitor, washed the appropriate microchip with sodium hydroxide, and placed in the loader the chip and a genotyping reagent pack with the reagents set forth in the following table. The user then implemented the loader protocol, the steps of which are set forth below.

TABLE 10

Genotyping Reagent Pack

| Well | Reagent | Description of Reagent |
|---|---|---|
| 1 | Blocker Group B1 | All blocked except G85E, ΔI507, 3120 + 1(G > A), 3849 + 10kb(C > T) |
| 2 | Blocker Group B2 | All blocked except 1711 − 1(G > A), G542X, G551D, R553X, R560T |
| 3 | Blocker Group B3 | All blocked except 1078delT, R347P, R334W, A455E, 1898 + 1(G > A) |
| 4 | Blocker Group B4 | All blocked except 711 + 1(G > T), 2184delA, 2789 + 5(G > A), R1162X, 3659delC |
| 5 | Blocker Group B5 | All blocked except 621 + 1(G > T), R117H, I148T, W1282X, N1303K |
| 6 | HRR Group 1 | G85E, ΔI507, 3120 + 1(G > A), 3849 + 10kb(C > T) |
| 7 | HRR Group 2 | 1711 − 1(G > A), G542X, G551D, R553X, R560T |
| 8 | HRR Group 3 | 1078delT, R347P, R334W, A455E, 1898 + 1(G > A) |
| 9 | HRR Group 4 | 711 + 1(G > T), 2184delA, 2789 + 5(G > A), R1162X, 3659delC |
| 10 | HRR Group 5 | 621 + 1(G > T), R117H, I148T, W1282X, N1303K |

The loader 1) loaded the heterozygous ratio reference (HRR) groups onto the chip and 2) electronically addressed them to a predetermined test site. Then, it 1) loaded the blocker mixes onto the chip and 2) electronically addressed them to a predetermined test site.

The user then removed the chip from the loader and added the appropriate genotyping reporter mixes for that protocol, as prompted by the ASM. The genotyping reporter mix was a reagent mix in high salt containing 1) wild-type and mutant discriminators for each of the variants in the screening variant group identified as containing a mutant in the screening run and 2) red and green universal reporters. The user then placed the chip in the reader and implemented the following reader protocol.

The reader increased the temperature of the chip to 56° C. for 60 seconds, decreased the temperature to 42° C. for 30 seconds, performed 8 high salt washes, and lowered the temperature to 24° C. Then, the reader performed discriminator scans (to detect red and green label) of the test sites with the samples, the test site with the histidine background, and the microlocations with the heterozygous ratio references, off-loading this data to the computer system. The reader then increased the temperature of the chip to 56° C. for 60 seconds, performed four high salt washes of the chip to denature the discriminators and lowered the temperature of the chip to 24° C. Then, it ejected the microchip that was analyzed, displaying a "complete" icon next to that protocol. If more than one screening variant group was identified as containing a mutation in the screening run, the user selected another protocol to run, and the ASM again prompted the user as to which microchip and genotyping reporter mix to use. This process was repeated until all of the necessary protocols had been run.

After all protocols had been run, the ASM analyzed the data collected. Background calculations for the sample and heterozygous ratio reference test sites were calculated and analyzed. If the signal from a particular sample test site did not meet the minimum signal criteria or signal to noise criteria, the ASM discontinued analysis of the suite to which the test site belonged and reported "no designation" for that patient sample and that the sample required a retest in the final report. And if the signal from the heterozygous ratio reference test site did not meet the minimum signal criteria or signal to noise criteria, the ASM discontinued analysis of all test sites on that chip and reported the failure and that a retest was required in the final report.

If the signal was usable, adjusted signal from each genotyping test site was converted into a genotyping indication by performing the same calculations as were described above in analyzing the dF508 variant during the screening run. Multipliers for each test site were calculated using the heterozygous ratio reference corresponding to the variant being genotyped at a particular test site. For example, the multiplier calculated from the test site containing HRR 1 was used to adjust the signal from test site 1 in each suite in which screening variant group 1 was identified as containing a mutation; the multiplier calculated from the test site containing HRR-2 was used to adjust the signal from test site 2, and so on.

In the final report, the ASM reported "mutant," "wild-type," and "heterozygote," or "no designation" for each test site that was genotyped. If all of the test sites in a particular suite produced wild-type designations, the ASM displayed a warning on the PC monitor indicating that the user most likely used an incorrect reporter. The user may then return to the reader and re-run the query with the correct reporter mix. If three or more mutations were detected for a single sample in a genotyping run, the following alert would be reported for that sample: "Alert: Three or more mutations are indicated for sample X. This sample should be retested for confirmation."

Unless the T-tract analysis was required (i.e., when a positive result is indicated for the R117H mutation or for any other mutation selected by the user in the user configurable setup to reflex to T-tract), the assay was complete and the ASM generated a final report. If a mutation was detected that required a reflex run, the ASM created the necessary protocol(s).

Reflex Run

If a reflex run was required the user washed the appropriate microchip with sodium hydroxide and added a first set of T-tract reporters to the chip. This set of reporters contained a high salt mix of 1) discriminators complementary to the amplicon sequence containing the 5T variant 2) discriminators complementary to amplicon sequence containing the 7T variant, and 3) universal reporters. In this portion of the assay, the green universal reporter binds to the 5T variant while the red universal reporter binds to the 7T variant. The user then implemented a reader protocol, the steps of which are set forth below.

The reader increased the temperature to 56° C. for 60 seconds, decreased temperature to 38° C. for 30 seconds, performed eight low salt washes, and decreased temperature to 24° C. Then, the reader performed a red/green scan of test site 6, the background control test site, and the T-tract heterozygous ratio reference test site, which was addressed with the dF508 heterozygous ratio reference during the screening run. The data collected was offloaded to the PC. After the scan the reader increased the temperature of the chip to 56° C., performed four low salt washes, and then set the temperature at 24° C.

After the washes, the user added a second mix of T-tract reporters to the microchip. This set of reporters contained a high salt mix of 1) discriminator probes complementary to the amplicon sequence containing the 5T variant 2) discriminator probes complementary to amplicon sequence containing the 9T variant, and 3) universal reporters. In this portion of the assay, the green universal reporter binds to the 5T variant while the red universal reporter binds to the 9T variant. The user then implemented a reader protocol, using the same heating, washing, and scanning steps set forth above in the first T-tract analysis.

The ASM then analyzed the collected data. If the signal from a particular sample test site did not meet the minimum signal criteria or signal to noise criteria, the ASM discontinued analysis of the suite to which the test site belonged and reported "no designation" for that patient sample and that the sample required a retest in the final report. If the signal from the T-tract heterozygous ratio reference test site did not meet the minimum signal criteria or signal to noise criteria, the ASM discontinued analysis of the entire chip and reported the failure and that a retest was required in the final report.

The usable signal from each scan was analyzed in the same manner as was the data from the genotyping run, wherein an adjusted signal was scaled using a multiplier and the signal from both the red and the green scan of one microlocation compared to make a genotyping determination. In this run, the mutant, wild-type, or heterozygote indications collected from the 5/7 and 5/9 scans must then be further correlated to arrive at a the final genotype, as follows:

If the signal from the 5/7 scans indicated WT and the signal from the 5/9 scans indicated WT, this indicated presence of the 5T variant.

If the signal from the 5/7 scans indicated Mut and there was no signal from the 5/9 scans, this indicated presence of the 7T variant.

If there was no signal from the 5/7 scans and the signal from the 5/9 scans indicated Mut, this indicated presence of the 9T variant.

If the signal from the 5/7 scans indicated Het and the signal from the 5/9 scans indicated WT, this indicated presence of the 5T/7T heterozygote.

If the signal from the 5/7 scans indicated WT and the signal from the 5/9 scans indicated Het, this indicated presence of the 5T/9T heterozygote.

If the signal from the 5/7 scans indicated Mut and the signal from the 5/9 scans indicated Mut, this indicated the presence of the 7T/9T heterozygote.

No designation could be made for all other combinations.

At this point, the assay was complete and the ASM reported these results as well as all of the other results gathered in each run in the final report.

TABLE 11

Discriminator Sequences

| Discriminator for: | Sequence |
|---|---|
| dI507, Wild-type | 5'aagatgatattttctttaactgagtccgaacattgag3' SEQ ID NO: 33 |
| Screening, dI507 Mutant | 5'aaagatattttctttaatttgcagtatatcgcttgaca3' SEQ ID NO: 34 |
| dI507, Mutant | 5'aaagatattttctttaatggcagtatatcgcttgaca3' SEQ ID NO: 35 |
| I507V, Mutant | 5'aagacgatattttctttaactgagtccgaacattgag3' SEQ ID NO: 36 |
| I506V, Mutant | 5'aagatgacattttctttaactgagtccgaacattgag3' SEQ ID NO: 37 |
| F508C, Mutant | 5'ctgagtccgaacattgagggaaacaccacaga3' SEQ ID NO: 38 |
| 1717-1, Wild type | 5'ctgagtccgaacattgaggatgtcctattacc3' SEQ ID NO: 39 |

TABLE 11-continued

Discriminator Sequences

| Discriminator for: | Sequence |
| --- | --- |
| 1717-1, Mutant | 5'gcagtatatcgcttgacagatgtcttattacc3' SEQ ID NO: 40 |
| Screening, 1717-1, mutant | 5'gcagtatatcgcttgacaagatgtcttattacc3' SEQ ID NO: 41 |
| 3659delC, Wild-type | 5'ctgagtccgaacattgagttgacttggtaggt3' SEQ ID NO: 42 |
| Screening 3659delC, Mutant | 5'gcagtatatcgcttgacattgacttgtaggttt3' SEQ ID NO: 43 |
| 3659delC, Mutant | 5'gcagtatatcgcttgacattgacttgtaggtt3' SEQ ID NO: 44 |
| G542X, Wild-type | 5'ctgagtccgaacattgagcttctccaagaact-3' SEQ ID NO: 45 |
| G542X, Mutant | 5'gcagtatatcgcttgacaccttctcaaagaac-3' SEQ ID NO: 46 |
| R553X, Wild-type | 5'ctgagtccgaacattgagtgctcgttgacc3' SEQ ID NO: 47 |
| R553X, Mutant | 5'gcagtatatcgcttgacattgctcattgacct3' SEQ ID NO: 48 |
| Screening R553X, Mutant | 5'gcagtatatcgcttgacataattcttgctca' SEQ ID NO: 49 |
| G85E, Wild-type | 5'ctgagtccgaacattgagagattccatagaac3' SEQ ID NO: 50 |
| G85E, Mutant | 5'gcagtatatcgcttgacaaagatttcatagaac3' SEQ ID NO: 51 |
| I148T, Wild-type | 5'ctgagtccgaacattgagcatcacattggaatg' SEQ ID NO: 52 |
| I148T, Mutant | 5'gcagtatatcgcttgacaatcacactggaatg3' SEQ ID NO: 53 |
| R117H, Wild-type | 5'ctgagtccgaacattgagggaacgctctatc3' SEQ ID NO: 54 |
| R117H, Mutant | 5'gcagtatatcgcttgacaggaacactctatcg3' SEQ ID NO: 55 |
| 711 + 1, Wild-type | 5'ctgagtccgaacattgagggtacatacttcatc3' SEQ ID NO: 56 |
| 711 + 1, Mutant | 5'gcagtatatcgcttgacaaggtacataattcat3' SEQ ID NO: 57 |
| R334W, Wild type | 5'ctgagtccgaacattgagcatcctccggaaaa3' SEQ ID NO: 58 |
| R334W, Mutant | 5'gcagtatatcgcttgacacatcctctggaaaa3' SEQ ID NO: 59 |
| 1078delT, Wild-type | 5'ctgagtccgaacattgaggttctttgtggtgt3' SEQ ID NO: 60 |
| 1078delT, Mutant | 5'gcagtatatcgcttgacagttcttgtggtgtt3' SEQ ID NO: 61 |
| Screening, 1078delT, Mutant | 5'gcagtatatcgcttgacagttcttgtggtgt3' SEQ ID NO: 62 |
| A455E, Wild type | 5'ctgagtccgaacattgagtggcggttgc3' SEQ ID NO: 63 |
| A455E, Mutant | 5'gcagtatatcgcttgacattggaggttgct3' SEQ ID NO: 64 |
| Δ508, Wild type | 5'ctgagtccgaacattgaggaaacaccaaaga3' SEQ ID NO: 65 |
| Δ508, Mutant | 5'gcagtatatcgcttgacaataggaaacaccgat3' SEQ ID NO: 66 |
| G551D, Wild type | 5'ctgagtccgaacattgagcgttgacctccac3' SEQ ID NO: 67 |
| G551D, Mutant | 5'gcagtatatcgcttgacacgttgatctccact3' SEQ ID NO: 68 |
| Screening G551D, Mutant | 5'tctccactcagttgcagtatatcgcttgaca3' SEQ ID NO: 69 |
| R560T, Wild type | 5'ctgagtccgaacattgagtattcaccttgcta3' SEQ ID NO: 70 |
| R560T, Mutant | 5'gcagtatatcgcttgacaattcacgttgcta3' SEQ ID NO: 71 |
| 2184delA, Wild-type | 5'ctgagtccgaacattgagattgttttttgtttc3' SEQ ID NO: 72 |
| 2184delA, Mutant | 5'gcagtatatcgcttgacaattgtttttttgtttct3' SEQ ID NO: 73 |
| 2789 + 5, Wild type | 5'ctgagtccgaacattgagaagtgagtattcc3' SEQ ID NO: 74 |
| 2789 + 5, Mutant | 5'gcagtatatcgcttgacaaaagtgaatattcca3' SEQ ID NO: 75 |

TABLE 11-continued

Discriminator Sequences

| Discriminator for: | Sequence |
|---|---|
| 3120 + 1, Wild type | 5'ctgagtccgaacattgagacatacctggatg3' SEQ ID NO: 76 |
| 3120 + 1 Mutant | 5'-gcagtatatcgcttgacaacatatctggatg-3' SEQ ID NO: 77 |
| R1162, Wild type | 5'ctgagtccgaacattgagctcggctcaca3' SEQ ID NO: 78 |
| R1162, Mutant | 5'gcagtatatcgcttgacagactcagctcaca3' SEQ ID NO: 79 |
| N1303K, Wild type | 5'ctgagtccgaacattgaggatccaagttttttt3' SEQ ID NO: 80 |
| N1303K, Mutant | 5'gcagtatatcgcttgacaatccaacttttttc3' SEQ ID NO: 81 |
| R347P, Wild type | 5'ctgagtccgaacattgagcattgttctgcg3' SEQ ID NO: 82 |
| R347P, Mutant | 5'gcagtatatcgcttgacaattgttctgcc3' SEQ ID NO: 83 |
| Stabilizer, R347P | 5'catggcggtcactcggcaatttccctg3' SEQ ID NO: 84 |
| 1898 + 1, Wild type | 5'-ctgagtccgaacattgagtgaaaggtatgttc-3' SEQ ID NO: 85 |
| 1898 + 1, Mutant | 5'gcagtatatcgcttgacattgaaagatatgttct3' SEQ ID NO: 86 |
| 621 + 1 Wild type | 5' ctgagtccgaacattgagataagaaggtaatac 3' SEQ ID NO: 87 |
| 621 + 1, Mutant | 5' gcagtatatcgcttgacatataagaagttaatact 3' SEQ ID NO: 88 |
| W1282X, Wild type | 5'ctgagtccgaacattgagacagtggaggaaa3' SEQ ID NO: 89 |
| W1282X, Mutant | 5'gcagtatatcgcttgacaacagtgaaggaaag3' SEQ ID NO: 90 |
| 3849 + 10kb, Wild type | 5'ctgagtccgaacattgagaaatggcgagta3' SEQ ID NO: 91 |
| 3849 + 10kb, Mutant | 5'gcagtatatcgcttgacaaaaatggtgagtaa3' SEQ ID NO: 92 |
| T-tract, 5T | 5'ctgagtccgaacattgagtgtgtttttaacaggg3' SEQ ID NO: 93 |
| T-tract, 7T | 5'gcagtatatcgcttgacatgtgttttttttaacaggg3' SEQ ID NO: 94 |
| T-tract, 9T | 5'gcagtatatcgcttgacatgtgttttttttttaacagg3' SEQ ID NO: 95 |
| Amplicon Confirmation, Exon 12 | 5'gcagtatatcgcttgacatgaaaggtatgttc3' SEQ ID NO: 96 |
| Amplicon Confirmation, Exon 21 | 5'gcagtatatcgcttgacagatccaagttttttt3' SEQ ID NO: 97 |
| Amplicon Confirmation, Exon 7 | 5'gcagtatatcgcttgacaGTTCTTTGTGGTGT3' SEQ ID NO: 98 |
| Amplicon Confirmation, Exon 9 | 5'gcagtatatcgcttgacaTGGCGGTTGC3' SEQ ID NO: 99 |
| Amplicon Confirmation, Exon 14b | 5'gcagtatatcgcttgacaAaagtgagtattcc3' SEQ ID NO: 100 |

TABLE 12

Blocker Sequences

| Blocker | Sequence |
|---|---|
| 3849 + 10kb Blocker | 5'gttgcagtattaaaatggygagtaagacaccctgaaaggaaatgttctattcatgg3' SEQ ID NO: 101 |
| Δ507 Blocker screening run | 5'gatattttctttaatggtgccaggcataatccaggaaaactgagaacagaatg3' SEQ ID NO: 102 |
| Δ508 Blocker screening run | 5'tgctttgatgacgcttctgtatctatattcatcataggaaacacc3' SEQ ID NO: 103 |
| Δ507/Δ508 wild-type Blocker | 5'tattcatcataggaaacaccaaagatgatattttctttaatggtg3' SEQ ID NO: 104 |

TABLE 12-continued

Blocker Sequences

| Blocker | Sequence |
|---|---|
| Δ507 Blocker, mutant | 5'ctatattcatcataggaaacaccaaagatattttctttaatggtg3' SEQ ID NO: 105 |
| Δ508 Blocker, mutant | 5'ctatattcatcataggaaacaccgatgatattttctttaatggtg3' SEQ ID NO: 106 |
| 621 + 1 Blocker | 5'tatgtttagtttgatttataagaagktaatacttccttgcacaggccccatggcacata3' SEQ ID NO: 107 |
| 2184DelA Blocker Wild type | 5'gtctgtttaaaagattgttttttgtttctgtccaggag3' SEQ ID NO: 108 |
| 2184DelA Blocker Mutant | 5'gtctgtttaaaagattgttttttgtttctgtccaggag3' SEQ ID NO: 109 |
| 1898 + 1 Blocker | 5'gatgttttaacagaaaaagaaatatttgaaagrtatgttctttgaataccttact3' SEQ ID NO: 110 |
| N1303K Blocker | 5'cactgttcatagggatccaastttttctaaatgttccag3' SEQ ID NO: 111 |
| W1282X Blocker | 5'caataactttgcaacagtgraggaaagcctttggagtgataccac3' SEQ ID NO: 112 |
| 711 + 1 Blocker | 5'gtgcctaaaagattaaatcaataggtacatamttcatcaaatttgttc3' SEQ ID NO: 113 |
| R117H Blocker | 5'cggataacaaggaggaacrctctatcgcgatttatctaggc3' SEQ ID NO: 114 |
| I148T Blocker | 5'gccattttttggccttcatcacaytggaatgcagatgagaatagc3' SEQ ID NO: 115 |
| G85E Blocker | 5'ccttacccctaaatataaaaagattycatagaacataaatctcc3' SEQ ID NO: 116 |
| 1162 Blocker | 5'caatgaacttaaagactcrgctcacagatcgcatctgaaataaaaa3' SEQ ID NO: 117 |
| 3659DelC Blocker Wild Type | 5'gtatggtttggttgacttggtaggtttaccttctg3' SEQ ID NO: 118 |
| 3659DelC Blocker Mutant | 5'gtatggtttggttgacttgtaggtttaccttctg3' SEQ ID NO: 119 |
| 3120 + 1Blocker | 5'cggtacttattttacataYctggatgaagtcaaatatggtaaga3' SEQ ID NO: 120 |
| 2789 + 5 Blocker | 5'-gtgctgtggctccttggaaagtgartattccatgtcctattgtgtagattgtg-3' SEQ ID NO: 121 |
| A455E Blocker | 5'gaggacagttgttggmggttgctggatccactggagcaggcaagg3' SEQ ID NO: 122 |
| R334W Blocker | 5'ctaatcaaaggaatcatcctcyggaaaatattcaccaccatctca3' SEQ ID NO: 123 |
| 1078DelT Blocker Wild Type | 5'gctcagccttcttcttctcagggttcttgtggtgtttttatctg3' SEQ ID NO: 124 |
| 1078DelT Blocker Mutant | 5'gctcagccttcttcttctcagggttcttgtggtgtttttatctg3' SEQ ID NO: 125 |
| R347P Blocker | 5'ttctgcattgttctgcscatggcggtcactcggcaatttccctgggctgta3' SEQ ID NO: 126 |
| 1717-1 Blocker | 5'gagatgtcytattaccaaaaatagaaaattagagagtcac3' SEQ ID NO: 127 |
| G542X Genotyping Blocker | 5'actttctcmaagaactatattgtctttctctgcaaacttg3' SEQ ID NO: 128 |
| G551D Screening Blocker | 5'ttgacctccactcagtgtgattccaccttctccaac3' SEQ ID NO: 129 |

TABLE 12-continued

Blocker Sequences

| Blocker | Sequence |
|---|---|
| G551D/R553X/R560T Blocker | 5'-tat tca cct tgc taa aga aat tct tgc tcg ttg acc tcc act-3' SEQ ID NO: 130 |
| G542X/G551D/R553X Blocker | 5'-ttg ctc gtt gac ctc cac tca gtg tga ttc cac ctt ctc caa gaa cta ta-3' SEQ ID NO: 131 |
| R553/X Blocker | 5'caataattagttattcaccttgctaaagaaattcttgctcgttga3' SEQ ID NO: 132 |
| R560T Blocker | 5'cttgctagaccaataattagttattcacyttgcta3' SEQ ID NO: 133 |

In a preferred embodiment, at least some of the steps described above can be accomplished using a computer system coupled to the device in the manner described below. In a preferred embodiment, at least some of the steps described above are automated and the computer and software components are readily adapted for any disease, group of diseases, or set of known polymorphisms.

Figure 8:
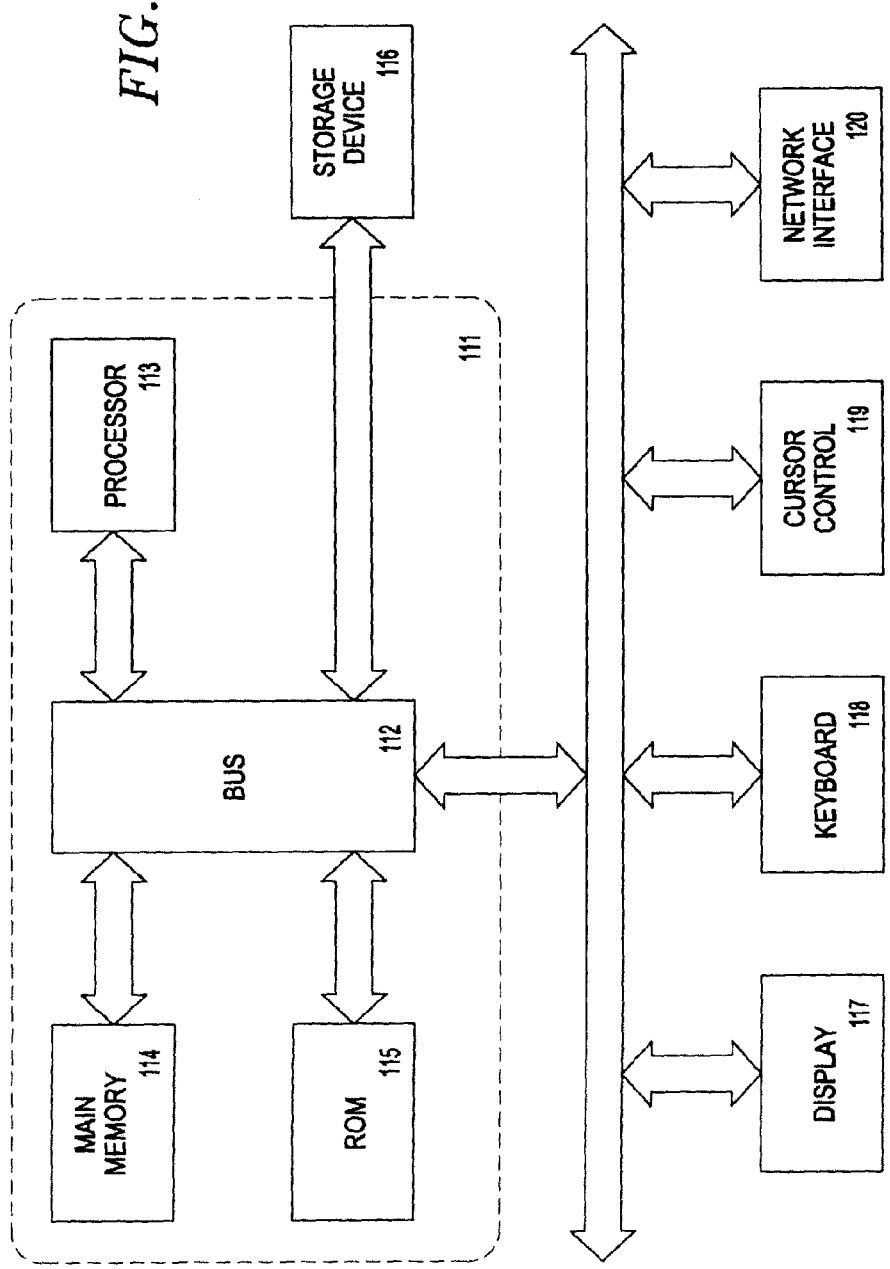
FIG. 8 is a block diagram of a computer system of the invention.

In a preferred embodiment the reader and the loader are coupled to a computer system capable of directing many of the steps described in the method for using the device set forth above and/or capable of analyzing the data gathered by the reader. FIG. 8 is a block diagram of a system 100 designed in accordance with the methods and systems disclosed herein. System 100 comprises Molecular Biology Workstation (MBW), which is comprised of a reader 102 having a dedicated CPU 103 and computer interface 104, and a loader 105 with a dedicated CPU 106.

Loader 105 is responsible for initiating and executing the steps leading to electronic addressing of the amplicons, heterozygous ratio references, background control, if any, and blockers to predetermined microlocations. In one embodiment, loader 105 comprises a processor for executing the instructions which make up the protocol responsible for accomplishing the above steps. In another embodiment, the system has a combined loader 105 and reader 102 which operate under the control of a central processor.

Reader 102 is responsible for detecting the hybridizing of amplification controls detecting signal, and offloading data to computer system 107 over communication link 108 for further processing. In a preferred embodiment, the reader 102 is also responsible for directing the loading of the discriminators onto the microchip device. In one embodiment, reader 102 comprises a processor for executing the instructions which make up the protocol responsible for the above-described hybridization of amplification controls, detecting signal, and offloading data for further processing. In another embodiment, reader 102 operates under the control of a central processor 103 included with MBW. In yet another embodiment, reader 102 operates under the control of a central processor included in computer system 107.

Computer interface 104 establishes electronic data communication between MBW and computer system 107. Computer interface 104 can comprise a physical link, such as a full-duplex USB connection, or other high-speed physical layer cable supporting an industry standard communication protocols. In another embodiment, communication link 108 can comprise a wireless link, supporting wireless data communications over an air interface. In still other embodiments, data communication over communication link 108 can occur as part of a private or public local area network (LAN), wide area network (WAN), or personal area network (PAN). In one embodiment, loading, reading and data analysis and processing is performed within a single integrated computer system 109 comprising multiple hardware and software subsystems programmed to execute the methods described herein and comprising a dedicated CPU 110. Thus, the assay methods can be a complete run-time environment including the loading, electronic addressing, reading, and data analysis steps that are implemented as loadable software modules. Such a modular system would permit a user to plug in those modules required for a particular customer environment. A further advantage to system modularity is the immediate feedback that the system can offer. For example, a system operator can know immediately if one step or microlocation in the assay has failed without having to wait until the entire assay run is complete. A modular system permits minimal user intervention by eliminating frequent tray changes and manual pipetting steps normally associated with assay management systems. The integrated system 109 may also have a communication link 108 to facilitate data communication to a separate computer system 107.

Figure 9:
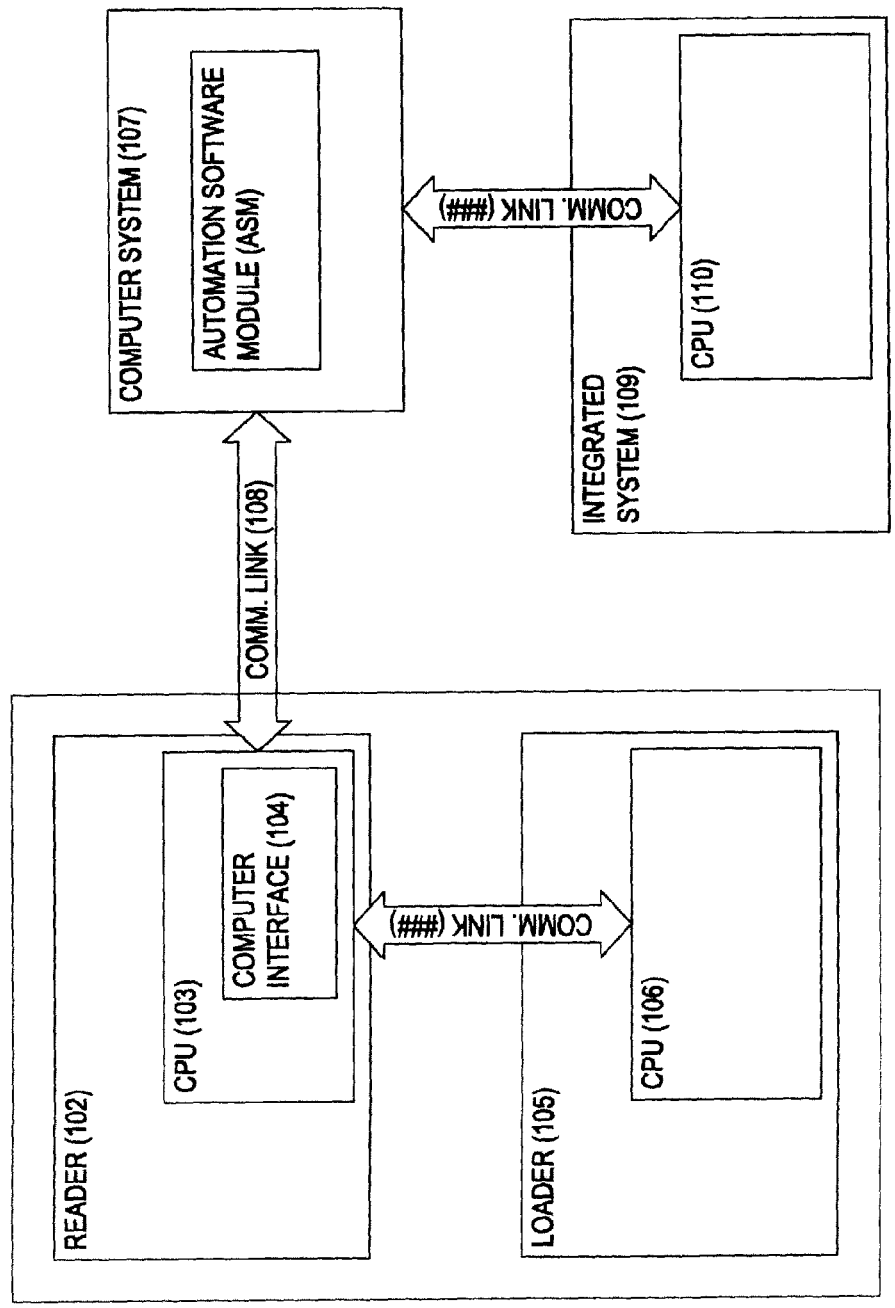
FIG. 9 is a block diagram of a work station useful in the system of the invention.

Computer system 107 can be a personal computer (PC) running a personal computer operating system, such as [Microsoft Windows 2000]. FIG. 9 is a block diagram of a computer system 111 upon which the methods for assaying can be implemented. Computer system 111 includes a bus 112 or other communication mechanism for communicating information, and a processor 113 coupled with bus 112 for processing information. Computer system 111 further comprises a random access memory (RAM) or other dynamic storage device 114 (referred to as main memory), coupled to bus 112 for storing information and instructions to be executed by processor 113. For example, RAM 114 can store the instructions comprising one or more software modules, such as an automation software module (ASM) for data analysis or a reader or loader software module for performing the steps involved in reading and loading respectively. Main memory 114 can also be used for storing temporary variables or other intermediate information during execution of instructions by processor 113. Computer system 111 also comprises a read only memory (ROM) and/or other static storage device 115 coupled to bus 112 for storing static information and instructions for processor 113. Data storage device 116, for storing information, (such as data collected from a reader), and instructions, (such as the instructions derived from an assay protocol), is connected to bus 112.

A data storage device 116 such as a magnetic disk or optical disk and its corresponding disk drive can be coupled to computer system 111. Computer system 111 can also be coupled via bus 112 to a display device 117, such as a cathode ray tube (CRT), for displaying information to a computer user. Computer system 111 can further include a keyboard 118 and a pointer control 119, such as a mouse.

The assaying methods described herein can also be deployed on computer system 111 in a stand-alone environment or in a client/server network having multiple computer systems 111 connected over a local area network (LAN) or a wide area network (WAN). Network interface 120 can be used to format data for transmission over such a network. In one embodiment, data is gathered from an MBW and passed via a protocol suite, such as TCP/IP, over the LAN or WAN infrastructure to a workstation or server attached to the network for further data processing. In another embodiment, the LAN or WAN is part of the Internet. In this embodiment, computer generated reports and forms can be formatted using a mark-up language, such as HTML or XML for static or dynamic data processing, messaging, and user input.

What is claimed is:

1. A kit for use in a process of detecting members of a set of polymorphisms that occur at identified loci in samples of a patient nucleic acid, said kit comprising:
- a group of unlabeled blockers capable of hybridizing under stringent conditions with markers in at least one locus contained in the patient sample nucleic acid thereby blocking said markers from further hybridizing to a detectable discriminator, wherein a specific nucleotide sequence of at least one unlabeled blocker of said group of unlabeled blockers is fully complementary to a nucleotide sequence comprising a mutation or a polymorphism in said at least one locus, and wherein the at least one unlabeled blocker is capable of hybridizing under said stringent conditions to the nucleotide sequence comprising the mutation or the polymorphism;
- more than one detectable discriminator, at least one of said more than one detectable discriminator capable of hybridizing under said stringent conditions with the nucleotide sequence comprising said mutation or polymorphism, said at least one unlabeled blocker being capable of blocking said at least one detectable discriminator from hybridizing with the nucleotide sequence comprising said mutation or polymorphism under said stringent conditions; and
- at least one universal reporter capable of binding with said more than one detectable discriminator,
- wherein said at least one of said more than one detectable discriminator is denatured from the nucleotide sequence comprising said mutation or said polymorphism in a hybridization product formed by said at least one detectable discriminator and the nucleotide sequence comprising said mutation or said polymorphism under denaturation condition while said at least one unlabeled blocker has a sufficient length so that said at least one unlabeled blocker remains to hybridize with the nucleotide sequence comprising said mutation or said polymorphism in a hybridization product formed by said at least one unlabeled blocker and the nucleotide sequence having said mutation or said polymorphism under said denaturation condition.

2. The kit of claim 1, further comprising at least one amplification control being capable of binding with the patient nucleic acid.

3. The kit of claim 2, further comprising an additional universal reporter capable of binding with the at least one amplification control.

4. The kit of claim 1, further comprising an actively addressable electronic microarray capable of being loaded with said patient sample nucleic acid at its individually addressable sites.

5. The kit of claim 1, wherein at least one of said unlabeled blockers and said at least one of said more than one detectable discriminator comprise oligonucleotides that are complementary to the at least one locus contained in the patient sample nucleic acid.

6. The kit of claim 5, wherein the universal reporter comprises a nucleotide sequence that is complementary to the nucleotides of said at least one of said more than one discriminator.

7. The kit of claim 1, wherein said at least one unlabeled blocker of said group of unlabeled blockers is capable of hybridizing to a locus contained in the patient sample nucleic acid that is different from a locus to which said at least one of said more than one detectable discriminator is capable of hybridizing.

* * * * *

SEQUENCE LISTING

<160> NUMBER OF SEQ ID NOS: 133

<210> SEQ ID NO 1
<211> LENGTH: 29
<212> TYPE: DNA
<213> ORGANISM: Human
<220> FEATURE:
<221> NAME/KEY: misc_feature
<223> OTHER INFORMATION: biotinylated exon 11

<400> SEQUENCE: 1
tcaactgtgg ttaaagcaat agtgtgata                                29

<210> SEQ ID NO 2
<211> LENGTH: 33
<212> TYPE: DNA
<213> ORGANISM: Human
<220> FEATURE:
<221> NAME/KEY: misc_feature
<223> OTHER INFORMATION: biotinylated exon 4

<400> SEQUENCE: 2
tttatccctt acttgtacca gctcactacc taa                           33

<210> SEQ ID NO 3
<211> LENGTH: 29
<212> TYPE: DNA
<213> ORGANISM: Human
<220> FEATURE:
<221> NAME/KEY: misc_feature
<223> OTHER INFORMATION: biotinylated exon 21

<400> SEQUENCE: 3
ttcacaaggg actccaaata ttgctgtag                                29

<210> SEQ ID NO 4
<211> LENGTH: 32
<212> TYPE: DNA
<213> ORGANISM: Human
<220> FEATURE:
<221> NAME/KEY: misc_feature
<223> OTHER INFORMATION: biotinylated exon 7

<400> SEQUENCE: 4
attatggtac attacctgta ttttgtttat tg                            32

<210> SEQ ID NO 5
<211> LENGTH: 33
<212> TYPE: DNA
<213> ORGANISM: Human
<220> FEATURE:
<221> NAME/KEY: misc_feature
<223> OTHER INFORMATION: biotinylated exon 10

<400> SEQUENCE: 5
gatgggtttt atttccagac ttcacttcta atg                           33

<210> SEQ ID NO 6

```
<211> LENGTH: 25
<212> TYPE: DNA
<213> ORGANISM: Human
<220> FEATURE:
<221> NAME/KEY: misc_feature
<223> OTHER INFORMATION: biotinylated exon 19

<400> SEQUENCE: 6
aattgtgaaa ttgtctgcca ttctt                                          25

<210> SEQ ID NO 7
<211> LENGTH: 27
<212> TYPE: DNA
<213> ORGANISM: Human
<220> FEATURE:
<221> NAME/KEY: misc_feature
<223> OTHER INFORMATION: biotinylated exon 16

<400> SEQUENCE: 7
gatatagcaa ttttggatga ccttctg                                        27

<210> SEQ ID NO 8
<211> LENGTH: 35
<212> TYPE: DNA
<213> ORGANISM: Human
<220> FEATURE:
<221> NAME/KEY: misc_feature
<223> OTHER INFORMATION: biotinylated exon 20

<400> SEQUENCE: 8
aatataattt agttgccttt tttctggcta agtcc                               35

<210> SEQ ID NO 9
<211> LENGTH: 27
<212> TYPE: DNA
<213> ORGANISM: Human
<220> FEATURE:
<221> NAME/KEY: misc_feature
<223> OTHER INFORMATION: biotinylated exon 12

<400> SEQUENCE: 9
tcaagaggta aaatgcaatc tatgatg                                        27

<210> SEQ ID NO 10
<211> LENGTH: 29
<212> TYPE: DNA
<213> ORGANISM: Human
<220> FEATURE:
<221> NAME/KEY: misc_feature
<223> OTHER INFORMATION: biotinylated exon 13

<400> SEQUENCE: 10
tgtctgtaaa ctgatggcta acaaaacta                                      29

<210> SEQ ID NO 11
<211> LENGTH: 25
<212> TYPE: DNA
<213> ORGANISM: Human
<220> FEATURE:
<221> NAME/KEY: misc_feature
<223> OTHER INFORMATION: biotinylated exon 14b

<400> SEQUENCE: 11
cactaccata atgcttggga gaaat                                          25

<210> SEQ ID NO 12
<211> LENGTH: 25
```

```
<212> TYPE: DNA
<213> ORGANISM: Human
<220> FEATURE:
<221> NAME/KEY: misc_feature
<223> OTHER INFORMATION: biotinylated exon 3

<400> SEQUENCE: 12
atgcaactta ttggtcccac ttttt                                        25

<210> SEQ ID NO 13
<211> LENGTH: 28
<212> TYPE: DNA
<213> ORGANISM: Human
<220> FEATURE:
<221> NAME/KEY: misc_feature
<223> OTHER INFORMATION: biotinylated exon 5

<400> SEQUENCE: 13
tgtcaagccg tgttctagat aaaataag                                     28

<210> SEQ ID NO 14
<211> LENGTH: 26
<212> TYPE: DNA
<213> ORGANISM: Human
<220> FEATURE:
<221> NAME/KEY: misc_feature
<223> OTHER INFORMATION: biotinylated intron 19

<400> SEQUENCE: 14
gttaaacagt gttgaatttg gtgcta                                       26

<210> SEQ ID NO 15
<211> LENGTH: 23
<212> TYPE: DNA
<213> ORGANISM: Human
<220> FEATURE:
<221> NAME/KEY: misc_feature
<223> OTHER INFORMATION: biotinylated exon 9

<400> SEQUENCE: 15
aagaactacc ttgcctgctc cag                                          23

<210> SEQ ID NO 16
<211> LENGTH: 31
<212> TYPE: DNA
<213> ORGANISM: Human
<220> FEATURE:
<221> NAME/KEY: misc_feature
<223> OTHER INFORMATION: Exon 11

<400> SEQUENCE: 16
cagaaacaga atataaagca atagagaaat g                                 31

<210> SEQ ID NO 17
<211> LENGTH: 26
<212> TYPE: DNA
<213> ORGANISM: Human
<220> FEATURE:
<221> NAME/KEY: misc_feature
<223> OTHER INFORMATION: Exon 4

<400> SEQUENCE: 17
tcaccaaagc agtacagcct ctctta                                       26

<210> SEQ ID NO 18
<211> LENGTH: 26
<212> TYPE: DNA
```

```
<213> ORGANISM: Human
<220> FEATURE:
<221> NAME/KEY: misc_feature
<223> OTHER INFORMATION: Exon 21

<400> SEQUENCE: 18
ccatatttct tgatcactcc actgtt                                              26

<210> SEQ ID NO 19
<211> LENGTH: 24
<212> TYPE: DNA
<213> ORGANISM: Human
<220> FEATURE:
<221> NAME/KEY: misc_feature
<223> OTHER INFORMATION: Exon 7

<400> SEQUENCE: 19
cagaactgaa actgactcgg aagg                                                24

<210> SEQ ID NO 20
<211> LENGTH: 26
<212> TYPE: DNA
<213> ORGANISM: Human
<220> FEATURE:
<221> NAME/KEY: misc_feature
<223> OTHER INFORMATION: Exon 10

<400> SEQUENCE: 20
atataatttg ggtagtgtga agggtt                                              26

<210> SEQ ID NO 21
<211> LENGTH: 19
<212> TYPE: DNA
<213> ORGANISM: Human
<220> FEATURE:
<221> NAME/KEY: misc_feature
<223> OTHER INFORMATION: Exon 19

<400> SEQUENCE: 21
ccctgagggc cagatgtca                                                      19

<210> SEQ ID NO 22
<211> LENGTH: 27
<212> TYPE: DNA
<213> ORGANISM: Human
<220> FEATURE:
<221> NAME/KEY: misc_feature
<223> OTHER INFORMATION: Exon 20

<400> SEQUENCE: 22
cctatatgtc acagaagtga tcccatc                                             27

<210> SEQ ID NO 23
<211> LENGTH: 27
<212> TYPE: DNA
<213> ORGANISM: Human
<220> FEATURE:
<221> NAME/KEY: misc_feature
<223> OTHER INFORMATION: Exon 12

<400> SEQUENCE: 23
gaactgttta aggcaaatca tctacac                                             27

<210> SEQ ID NO 24
<211> LENGTH: 20
<212> TYPE: DNA
<213> ORGANISM: Human
```

```
<220> FEATURE:
<221> NAME/KEY: misc_feature
<223> OTHER INFORMATION: Exon 13

<400> SEQUENCE: 24
ttccccaaac tctccagtct                                              20

<210> SEQ ID NO 25
<211> LENGTH: 29
<212> TYPE: DNA
<213> ORGANISM: Human
<220> FEATURE:
<221> NAME/KEY: misc_feature
<223> OTHER INFORMATION: Exon 14b

<400> SEQUENCE: 25
aggtgaagat gttagaaaaa aaatcaact                                    29

<210> SEQ ID NO 26
<211> LENGTH: 29
<212> TYPE: DNA
<213> ORGANISM: Human
<220> FEATURE:
<221> NAME/KEY: misc_feature
<223> OTHER INFORMATION: Exon 3

<400> SEQUENCE: 26
cacaaaaatg catatagtta tgtgataca                                    29

<210> SEQ ID NO 27
<211> LENGTH: 25
<212> TYPE: DNA
<213> ORGANISM: Human
<220> FEATURE:
<221> NAME/KEY: misc_feature
<223> OTHER INFORMATION: Exon 5

<400> SEQUENCE: 27
aactccgcct ttccagttgt ataat                                        25

<210> SEQ ID NO 28
<211> LENGTH: 26
<212> TYPE: DNA
<213> ORGANISM: Human
<220> FEATURE:
<221> NAME/KEY: misc_feature
<223> OTHER INFORMATION: Intron 19

<400> SEQUENCE: 28
gacttgtcat cttgatttct ggagac                                       26

<210> SEQ ID NO 29
<211> LENGTH: 31
<212> TYPE: DNA
<213> ORGANISM: Human
<220> FEATURE:
<221> NAME/KEY: misc_feature
<223> OTHER INFORMATION: Exon 9

<400> SEQUENCE: 29
agatcatgtc ctctagaaac cgtatgctat a                                 31

<210> SEQ ID NO 30
<211> LENGTH: 29
<212> TYPE: DNA
<213> ORGANISM: Human
<220> FEATURE:
```

```
<221> NAME/KEY: misc_feature
<223> OTHER INFORMATION: Exon 16

<400> SEQUENCE: 30
tcacatttgc ttttgttatt gttttttta                                              29

<210> SEQ ID NO 31
<211> LENGTH: 18
<212> TYPE: DNA
<213> ORGANISM: Human
<220> FEATURE:
<221> NAME/KEY: misc_feature
<223> OTHER INFORMATION: Universal Reporter, Red

<400> SEQUENCE: 31
ctcaatgttc ggactcag                                                          18

<210> SEQ ID NO 32
<211> LENGTH: 18
<212> TYPE: DNA
<213> ORGANISM: Human
<220> FEATURE:
<221> NAME/KEY: misc_feature
<223> OTHER INFORMATION: Universal Reporter, Green

<400> SEQUENCE: 32
tgtcaagcga tatactgc                                                          18

<210> SEQ ID NO 33
<211> LENGTH: 37
<212> TYPE: DNA
<213> ORGANISM: Human
<220> FEATURE:
<221> NAME/KEY: misc_feature
<223> OTHER INFORMATION: dI507, Wild-type

<400> SEQUENCE: 33
aagatgatat tttcttaac tgagtccgaa cattgag                                      37

<210> SEQ ID NO 34
<211> LENGTH: 38
<212> TYPE: DNA
<213> ORGANISM: Human
<220> FEATURE:
<221> NAME/KEY: misc_feature
<223> OTHER INFORMATION: Screening dI507 Mutant

<400> SEQUENCE: 34
aaagatattt tctttaattt gcagtatatc gcttgaca                                    38

<210> SEQ ID NO 35
<211> LENGTH: 37
<212> TYPE: DNA
<213> ORGANISM: Human
<220> FEATURE:
<221> NAME/KEY: misc_feature
<223> OTHER INFORMATION: dI507 Mutant

<400> SEQUENCE: 35
aaagatattt tctttaatgg cagtatatcg cttgaca                                     37

<210> SEQ ID NO 36
<211> LENGTH: 37
<212> TYPE: DNA
<213> ORGANISM: Human
<220> FEATURE:
<221> NAME/KEY: misc_feature
```

```
<223> OTHER INFORMATION: I507V, Mutant

<400> SEQUENCE: 36
aagacgatat tttctttaac tgagtccgaa cattgag                         37

<210> SEQ ID NO 37
<211> LENGTH: 37
<212> TYPE: DNA
<213> ORGANISM: Human
<220> FEATURE:
<221> NAME/KEY: misc_feature
<223> OTHER INFORMATION: I506V, Mutant

<400> SEQUENCE: 37
aagatgacat tttctttaac tgagtccgaa cattgag                         37

<210> SEQ ID NO 38
<211> LENGTH: 32
<212> TYPE: DNA
<213> ORGANISM: Human
<220> FEATURE:
<221> NAME/KEY: misc_feature
<223> OTHER INFORMATION: F508C, Mutant

<400> SEQUENCE: 38
ctgagtccga acattgaggg aaacaccaca ga                              32

<210> SEQ ID NO 39
<211> LENGTH: 32
<212> TYPE: DNA
<213> ORGANISM: Human
<220> FEATURE:
<221> NAME/KEY: misc_feature
<223> OTHER INFORMATION: 1717-1, Wild-type

<400> SEQUENCE: 39
ctgagtccga acattgagga tgtcctatta cc                              32

<210> SEQ ID NO 40
<211> LENGTH: 32
<212> TYPE: DNA
<213> ORGANISM: Human
<220> FEATURE:
<221> NAME/KEY: misc_feature
<223> OTHER INFORMATION: 1717-1, Mutant

<400> SEQUENCE: 40
gcagtatatc gcttgacaga tgtcttatta cc                              32

<210> SEQ ID NO 41
<211> LENGTH: 33
<212> TYPE: DNA
<213> ORGANISM: Human
<220> FEATURE:
<221> NAME/KEY: misc_feature
<223> OTHER INFORMATION: Screening 1717-1, Mutant

<400> SEQUENCE: 41
gcagtatatc gcttgacaag atgtcttatt acc                             33

<210> SEQ ID NO 42
<211> LENGTH: 32
<212> TYPE: DNA
<213> ORGANISM: Human
<220> FEATURE:
<221> NAME/KEY: misc_feature
<223> OTHER INFORMATION: 3659delC, Wild-type
```

```
<400> SEQUENCE: 42
ctgagtccga acattgagtt gacttggtag gt                                    32

<210> SEQ ID NO 43
<211> LENGTH: 33
<212> TYPE: DNA
<213> ORGANISM: Human
<220> FEATURE:
<221> NAME/KEY: misc_feature
<223> OTHER INFORMATION: Screening 3659delC, Mutant

<400> SEQUENCE: 43
gcagtatatc gcttgacatt gacttgtagg ttt                                   33

<210> SEQ ID NO 44
<211> LENGTH: 32
<212> TYPE: DNA
<213> ORGANISM: Human
<220> FEATURE:
<221> NAME/KEY: misc_feature
<223> OTHER INFORMATION: 3659delC, Mutant

<400> SEQUENCE: 44
gcagtatatc gcttgacatt gacttgtagg tt                                    32

<210> SEQ ID NO 45
<211> LENGTH: 32
<212> TYPE: DNA
<213> ORGANISM: Human
<220> FEATURE:
<221> NAME/KEY: misc_feature
<223> OTHER INFORMATION: G542X, Wild-type

<400> SEQUENCE: 45
ctgagtccga acattgagct tctccaagaa ct                                    32

<210> SEQ ID NO 46
<211> LENGTH: 32
<212> TYPE: DNA
<213> ORGANISM: Human
<220> FEATURE:
<221> NAME/KEY: misc_feature
<223> OTHER INFORMATION: G542X, Mutant

<400> SEQUENCE: 46
gcagtatatc gcttgacacc ttctcaaaga ac                                    32

<210> SEQ ID NO 47
<211> LENGTH: 30
<212> TYPE: DNA
<213> ORGANISM: Human
<220> FEATURE:
<221> NAME/KEY: misc_feature
<223> OTHER INFORMATION: R553X, Wild-type

<400> SEQUENCE: 47
ctgagtccga acattgagtg ctcgttgacc                                       30

<210> SEQ ID NO 48
<211> LENGTH: 32
<212> TYPE: DNA
<213> ORGANISM: Human
<220> FEATURE:
<221> NAME/KEY: misc_feature
<223> OTHER INFORMATION: R553X, Mutant
```

<400> SEQUENCE: 48
gcagtatatc gcttgacatt gctcattgac ct                               32

<210> SEQ ID NO 49
<211> LENGTH: 31
<212> TYPE: DNA
<213> ORGANISM: Human
<220> FEATURE:
<221> NAME/KEY: misc_feature
<223> OTHER INFORMATION: Screening R553X, Mutant

<400> SEQUENCE: 49
gcagtatatc gcttgacata attcttgctc a                                31

<210> SEQ ID NO 50
<211> LENGTH: 32
<212> TYPE: DNA
<213> ORGANISM: Human
<220> FEATURE:
<221> NAME/KEY: misc_feature
<223> OTHER INFORMATION: G85E, Wild-type

<400> SEQUENCE: 50
ctgagtccga acattgagag attccataga ac                               32

<210> SEQ ID NO 51
<211> LENGTH: 33
<212> TYPE: DNA
<213> ORGANISM: Human
<220> FEATURE:
<221> NAME/KEY: misc_feature
<223> OTHER INFORMATION: G85E, Mutant

<400> SEQUENCE: 51
gcagtatatc gcttgacaaa gatttcatag aac                              33

<210> SEQ ID NO 52
<211> LENGTH: 33
<212> TYPE: DNA
<213> ORGANISM: Human
<220> FEATURE:
<221> NAME/KEY: misc_feature
<223> OTHER INFORMATION: I148T, Wild-type

<400> SEQUENCE: 52
ctgagtccga acattgagca tcacattgga atg                              33

<210> SEQ ID NO 53
<211> LENGTH: 32
<212> TYPE: DNA
<213> ORGANISM: Human
<220> FEATURE:
<221> NAME/KEY: misc_feature
<223> OTHER INFORMATION: I148T, Mutant

<400> SEQUENCE: 53
gcagtatatc gcttgacaat cacactggaa tg                               32

<210> SEQ ID NO 54
<211> LENGTH: 31
<212> TYPE: DNA
<213> ORGANISM: Human
<220> FEATURE:
<221> NAME/KEY: misc_feature
<223> OTHER INFORMATION: R117H, Wild-type

<400> SEQUENCE: 54
ctgagtccga acattgaggg aacgctctat c                                31

<210> SEQ ID NO 55
<211> LENGTH: 32
<212> TYPE: DNA
<213> ORGANISM: Human
<220> FEATURE:
<221> NAME/KEY: misc_feature
<223> OTHER INFORMATION: R117H, Mutant

<400> SEQUENCE: 55
gcagtatatc gcttgacagg aacactctat cg                               32

<210> SEQ ID NO 56
<211> LENGTH: 33
<212> TYPE: DNA
<213> ORGANISM: Human
<220> FEATURE:
<221> NAME/KEY: misc_feature
<223> OTHER INFORMATION: 711+1, Wild-type

<400> SEQUENCE: 56
ctgagtccga acattgaggg tacatacttc atc                              33

<210> SEQ ID NO 57
<211> LENGTH: 33
<212> TYPE: DNA
<213> ORGANISM: Human
<220> FEATURE:
<221> NAME/KEY: misc_feature
<223> OTHER INFORMATION: 711+1, Mutant

<400> SEQUENCE: 57
gcagtatatc gcttgacaag gtacataatt cat                              33

<210> SEQ ID NO 58
<211> LENGTH: 32
<212> TYPE: DNA
<213> ORGANISM: Human
<220> FEATURE:
<221> NAME/KEY: misc_feature
<223> OTHER INFORMATION: R334W, Wild-type

<400> SEQUENCE: 58
ctgagtccga acattgagca tcctccggaa aa                               32

<210> SEQ ID NO 59
<211> LENGTH: 32
<212> TYPE: DNA
<213> ORGANISM: Human
<220> FEATURE:
<221> NAME/KEY: misc_feature
<223> OTHER INFORMATION: R334W, Mutant

<400> SEQUENCE: 59
gcagtatatc gcttgacaca tcctctggaa aa                               32

<210> SEQ ID NO 60
<211> LENGTH: 32
<212> TYPE: DNA
<213> ORGANISM: Human
<220> FEATURE:
<221> NAME/KEY: misc_feature
<223> OTHER INFORMATION: 1078delT, Wild-type

<400> SEQUENCE: 60
ctgagtccga acattgaggt tctttgtggt gt                               32

<210> SEQ ID NO 61
<211> LENGTH: 32
<212> TYPE: DNA
<213> ORGANISM: Human
<220> FEATURE:
<221> NAME/KEY: misc_feature
<223> OTHER INFORMATION: 1078delT, Mutant

<400> SEQUENCE: 61
gcagtatatc gcttgacagt tcttgtggtg tt                               32

<210> SEQ ID NO 62
<211> LENGTH: 31
<212> TYPE: DNA
<213> ORGANISM: Human
<220> FEATURE:
<221> NAME/KEY: misc_feature
<223> OTHER INFORMATION: Screening 1078delT, Mutant

<400> SEQUENCE: 62
gcagtatatc gcttgacagt tcttgtggtg t                                31

<210> SEQ ID NO 63
<211> LENGTH: 28
<212> TYPE: DNA
<213> ORGANISM: Human
<220> FEATURE:
<221> NAME/KEY: misc_feature
<223> OTHER INFORMATION: A455E, Wild-type

<400> SEQUENCE: 63
ctgagtccga acattgagtg gcggttgc                                    28

<210> SEQ ID NO 64
<211> LENGTH: 30
<212> TYPE: DNA
<213> ORGANISM: Human
<220> FEATURE:
<221> NAME/KEY: misc_feature
<223> OTHER INFORMATION: A455E, Mutant

<400> SEQUENCE: 64
gcagtatatc gcttgacatt ggaggttgct                                  30

<210> SEQ ID NO 65
<211> LENGTH: 31
<212> TYPE: DNA
<213> ORGANISM: Human
<220> FEATURE:
<221> NAME/KEY: misc_feature
<223> OTHER INFORMATION: delta-508, Wild-type

<400> SEQUENCE: 65
ctgagtccga acattgagga aacaccaaag a                                31

<210> SEQ ID NO 66
<211> LENGTH: 33
<212> TYPE: DNA
<213> ORGANISM: Human
<220> FEATURE:
<221> NAME/KEY: misc_feature
<223> OTHER INFORMATION: delta-508, Mutant

<400> SEQUENCE: 66
gcagtatatc gcttgacaat aggaaacacc gat                              33

<210> SEQ ID NO 67
<211> LENGTH: 31
<212> TYPE: DNA
<213> ORGANISM: Human
<220> FEATURE:
<221> NAME/KEY: misc_feature
<223> OTHER INFORMATION: G551D, Wild-type

<400> SEQUENCE: 67
ctgagtccga acattgagcg ttgacctcca c                          31

<210> SEQ ID NO 68
<211> LENGTH: 32
<212> TYPE: DNA
<213> ORGANISM: Human
<220> FEATURE:
<221> NAME/KEY: misc_feature
<223> OTHER INFORMATION: G551D, Mutant

<400> SEQUENCE: 68
gcagtatatc gcttgacacg ttgatctcca ct                         32

<210> SEQ ID NO 69
<211> LENGTH: 31
<212> TYPE: DNA
<213> ORGANISM: Human
<220> FEATURE:
<221> NAME/KEY: misc_feature
<223> OTHER INFORMATION: Screening G551D, Mutant

<400> SEQUENCE: 69
tctccactca gttgcagtat atcgcttgac a                          31

<210> SEQ ID NO 70
<211> LENGTH: 32
<212> TYPE: DNA
<213> ORGANISM: Human
<220> FEATURE:
<221> NAME/KEY: misc_feature
<223> OTHER INFORMATION: R560T, Wild-type

<400> SEQUENCE: 70
ctgagtccga acattgagta ttcaccttgc ta                         32

<210> SEQ ID NO 71
<211> LENGTH: 31
<212> TYPE: DNA
<213> ORGANISM: Human
<220> FEATURE:
<221> NAME/KEY: misc_feature
<223> OTHER INFORMATION: R560T, Mutant

<400> SEQUENCE: 71
gcagtatatc gcttgacaat tcacgttgct a                          31

<210> SEQ ID NO 72
<211> LENGTH: 34
<212> TYPE: DNA
<213> ORGANISM: Human
<220> FEATURE:
<221> NAME/KEY: misc_feature
<223> OTHER INFORMATION: 2184delA, Wild-type

<400> SEQUENCE: 72
ctgagtccga acattgagat tgttttttttg tttc                      34

<210> SEQ ID NO 73
<211> LENGTH: 34
<212> TYPE: DNA
<213> ORGANISM: Human
<220> FEATURE:
<221> NAME/KEY: misc_feature
<223> OTHER INFORMATION: 2184delA, Mutant

<400> SEQUENCE: 73
gcagtatatc gcttgacaat tgttttttgt ttct                      34

<210> SEQ ID NO 74
<211> LENGTH: 31
<212> TYPE: DNA
<213> ORGANISM: Human
<220> FEATURE:
<221> NAME/KEY: misc_feature
<223> OTHER INFORMATION: 2789+5, Wild-type

<400> SEQUENCE: 74
ctgagtccga acattgagaa gtgagtattc c                         31

<210> SEQ ID NO 75
<211> LENGTH: 33
<212> TYPE: DNA
<213> ORGANISM: Human
<220> FEATURE:
<221> NAME/KEY: misc_feature
<223> OTHER INFORMATION: 2789+5, Mutant

<400> SEQUENCE: 75
gcagtatatc gcttgacaaa agtgaatatt cca                       33

<210> SEQ ID NO 76
<211> LENGTH: 31
<212> TYPE: DNA
<213> ORGANISM: Human
<220> FEATURE:
<221> NAME/KEY: misc_feature
<223> OTHER INFORMATION: 3120+1, Wild-type

<400> SEQUENCE: 76
ctgagtccga acattgagac atacctggat g                         31

<210> SEQ ID NO 77
<211> LENGTH: 31
<212> TYPE: DNA
<213> ORGANISM: Human
<220> FEATURE:
<221> NAME/KEY: misc_feature
<223> OTHER INFORMATION: 3120+1, Mutant

<400> SEQUENCE: 77
gcagtatatc gcttgacaac atatctggat g                         31

<210> SEQ ID NO 78
<211> LENGTH: 29
<212> TYPE: DNA
<213> ORGANISM: Human
<220> FEATURE:
<221> NAME/KEY: misc_feature
<223> OTHER INFORMATION: R1162, Wild-type

<400> SEQUENCE: 78
ctgagtccga acattgagct cggctcaca                            29

```
<210> SEQ ID NO 79
<211> LENGTH: 31
<212> TYPE: DNA
<213> ORGANISM: Human
<220> FEATURE:
<221> NAME/KEY: misc_feature
<223> OTHER INFORMATION: R1162, Mutant

<400> SEQUENCE: 79
gcagtatatc gcttgacaga ctcagctcac a                              31

<210> SEQ ID NO 80
<211> LENGTH: 32
<212> TYPE: DNA
<213> ORGANISM: Human
<220> FEATURE:
<221> NAME/KEY: misc_feature
<223> OTHER INFORMATION: N1303K, Wild-type

<400> SEQUENCE: 80
ctgagtccga acattgagga tccaagtttt tt                             32

<210> SEQ ID NO 81
<211> LENGTH: 32
<212> TYPE: DNA
<213> ORGANISM: Human
<220> FEATURE:
<221> NAME/KEY: misc_feature
<223> OTHER INFORMATION: N1303K, Mutant

<400> SEQUENCE: 81
gcagtatatc gcttgacaat ccaacttttt tc                             32

<210> SEQ ID NO 82
<211> LENGTH: 30
<212> TYPE: DNA
<213> ORGANISM: Human
<220> FEATURE:
<221> NAME/KEY: misc_feature
<223> OTHER INFORMATION: R347P, Wild-type

<400> SEQUENCE: 82
ctgagtccga acattgagca ttgttctgcg                                30

<210> SEQ ID NO 83
<211> LENGTH: 29
<212> TYPE: DNA
<213> ORGANISM: Human
<220> FEATURE:
<221> NAME/KEY: misc_feature
<223> OTHER INFORMATION: R347P, Mutant

<400> SEQUENCE: 83
gcagtatatc gcttgacaat tgttctgcc                                 29

<210> SEQ ID NO 84
<211> LENGTH: 27
<212> TYPE: DNA
<213> ORGANISM: Human
<220> FEATURE:
<221> NAME/KEY: misc_feature
<223> OTHER INFORMATION: Stabilizer, R347P

<400> SEQUENCE: 84
catggcggtc actcggcaat ttccctg                                   27

<210> SEQ ID NO 85
```

```
<211> LENGTH: 32
<212> TYPE: DNA
<213> ORGANISM: Human
<220> FEATURE:
<221> NAME/KEY: misc_feature
<223> OTHER INFORMATION: 1898+1, Wild-type

<400> SEQUENCE: 85
ctgagtccga acattgagtg aaaggtatgt tc                                      32

<210> SEQ ID NO 86
<211> LENGTH: 34
<212> TYPE: DNA
<213> ORGANISM: Human
<220> FEATURE:
<221> NAME/KEY: misc_feature
<223> OTHER INFORMATION: 1898+1, Mutant

<400> SEQUENCE: 86
gcagtatatc gcttgacatt gaaagatatg ttct                                    34

<210> SEQ ID NO 87
<211> LENGTH: 33
<212> TYPE: DNA
<213> ORGANISM: Human
<220> FEATURE:
<221> NAME/KEY: misc_feature
<223> OTHER INFORMATION: 621+1, Wild-type

<400> SEQUENCE: 87
ctgagtccga acattgagat aagaaggtaa tac                                     33

<210> SEQ ID NO 88
<211> LENGTH: 35
<212> TYPE: DNA
<213> ORGANISM: Human
<220> FEATURE:
<221> NAME/KEY: misc_feature
<223> OTHER INFORMATION: 621+1, Mutant

<400> SEQUENCE: 88
gcagtatatc gcttgacata taagaagtta atact                                   35

<210> SEQ ID NO 89
<211> LENGTH: 31
<212> TYPE: DNA
<213> ORGANISM: Human
<220> FEATURE:
<221> NAME/KEY: misc_feature
<223> OTHER INFORMATION: W1282X, Wild-type

<400> SEQUENCE: 89
ctgagtccga acattgagac agtggaggaa a                                       31

<210> SEQ ID NO 90
<211> LENGTH: 32
<212> TYPE: DNA
<213> ORGANISM: Human
<220> FEATURE:
<221> NAME/KEY: misc_feature
<223> OTHER INFORMATION: W1282X, Mutant

<400> SEQUENCE: 90
gcagtatatc gcttgacaac agtgaaggaa ag                                      32

<210> SEQ ID NO 91
<211> LENGTH: 30
```

```
<212> TYPE: DNA
<213> ORGANISM: Human
<220> FEATURE:
<221> NAME/KEY: misc_feature
<223> OTHER INFORMATION: 3849+10kb, Wild-type

<400> SEQUENCE: 91
ctgagtccga acattgagaa atggcgagta                                          30

<210> SEQ ID NO 92
<211> LENGTH: 32
<212> TYPE: DNA
<213> ORGANISM: Human
<220> FEATURE:
<221> NAME/KEY: misc_feature
<223> OTHER INFORMATION: 3849+10kb, Mutant

<400> SEQUENCE: 92
gcagtatatc gcttgacaaa aatggtgagt aa                                       32

<210> SEQ ID NO 93
<211> LENGTH: 34
<212> TYPE: DNA
<213> ORGANISM: Human
<220> FEATURE:
<221> NAME/KEY: misc_feature
<223> OTHER INFORMATION: T-tract, 5T

<400> SEQUENCE: 93
ctgagtccga acattgagtg tgtttttaac aggg                                     34

<210> SEQ ID NO 94
<211> LENGTH: 36
<212> TYPE: DNA
<213> ORGANISM: Human
<220> FEATURE:
<221> NAME/KEY: misc_feature
<223> OTHER INFORMATION: T-tract, 7T

<400> SEQUENCE: 94
gcagtatatc gcttgacatg tgttttttta acaggg                                   36

<210> SEQ ID NO 95
<211> LENGTH: 37
<212> TYPE: DNA
<213> ORGANISM: Human
<220> FEATURE:
<221> NAME/KEY: misc_feature
<223> OTHER INFORMATION: T-tract, 9T

<400> SEQUENCE: 95
gcagtatatc gcttgacatg tgttttttttt taacagg                                 37

<210> SEQ ID NO 96
<211> LENGTH: 32
<212> TYPE: DNA
<213> ORGANISM: Human
<220> FEATURE:
<221> NAME/KEY: misc_feature
<223> OTHER INFORMATION: Amplicon Confirmation, Exon 12

<400> SEQUENCE: 96
gcagtatatc gcttgacatg aaaggtatgt tc                                       32

<210> SEQ ID NO 97
<211> LENGTH: 32
<212> TYPE: DNA
```

<213> ORGANISM: Human
<220> FEATURE:
<221> NAME/KEY: misc_feature
<223> OTHER INFORMATION: Amplicon Confirmation, Exon 21

<400> SEQUENCE: 97
gcagtatatc gcttgacaga tccaagttttt tt                             32

<210> SEQ ID NO 98
<211> LENGTH: 32
<212> TYPE: DNA
<213> ORGANISM: Human
<220> FEATURE:
<221> NAME/KEY: misc_feature
<223> OTHER INFORMATION: Amplicon Confirmation, Exon 7

<400> SEQUENCE: 98
gcagtatatc gcttgacagt tctttgtggt gt                              32

<210> SEQ ID NO 99
<211> LENGTH: 28
<212> TYPE: DNA
<213> ORGANISM: Human
<220> FEATURE:
<221> NAME/KEY: misc_feature
<223> OTHER INFORMATION: Amplicon Confirmation, Exon 9

<400> SEQUENCE: 99
gcagtatatc gcttgacatg gcggttgc                                   28

<210> SEQ ID NO 100
<211> LENGTH: 32
<212> TYPE: DNA
<213> ORGANISM: Human
<220> FEATURE:
<221> NAME/KEY: misc_feature
<223> OTHER INFORMATION: Amplicon Confirmation, Exon 14b

<400> SEQUENCE: 100
gcagtatatc gcttgacaaa agtgagtatt cc                              32

<210> SEQ ID NO 101
<211> LENGTH: 56
<212> TYPE: DNA
<213> ORGANISM: Human
<220> FEATURE:
<221> NAME/KEY: misc_feature
<223> OTHER INFORMATION: 3849+10kb Blocker

<400> SEQUENCE: 101
gttgcagtat taaaatggyg agtaagacac cctgaaagga aatgttctat tcatgg    56

<210> SEQ ID NO 102
<211> LENGTH: 53
<212> TYPE: DNA
<213> ORGANISM: Human
<220> FEATURE:
<221> NAME/KEY: misc_feature
<223> OTHER INFORMATION: delta-507 Blocker screening run

<400> SEQUENCE: 102
gatattttct ttaatggtgc caggcataat ccaggaaaac tgagaacaga atg       53

<210> SEQ ID NO 103
<211> LENGTH: 45
<212> TYPE: DNA
<213> ORGANISM: Human

-continued

```
<220> FEATURE:
<221> NAME/KEY: misc_feature
<223> OTHER INFORMATION: delta-508 Blocker screening run

<400> SEQUENCE: 103
tgctttgatg acgcttctgt atctatattc atcataggaa acacc              45

<210> SEQ ID NO 104
<211> LENGTH: 45
<212> TYPE: DNA
<213> ORGANISM: Human
<220> FEATURE:
<221> NAME/KEY: misc_feature
<223> OTHER INFORMATION: delta-507/delta-508 wild-type Blocker

<400> SEQUENCE: 104
tattcatcat aggaaacacc aaagatgata ttttctttaa tggtg              45

<210> SEQ ID NO 105
<211> LENGTH: 45
<212> TYPE: DNA
<213> ORGANISM: Human
<220> FEATURE:
<221> NAME/KEY: misc_feature
<223> OTHER INFORMATION: delta-507 Blocker, Mutant

<400> SEQUENCE: 105
ctatattcat cataggaaac accaaagata ttttctttaa tggtg              45

<210> SEQ ID NO 106
<211> LENGTH: 45
<212> TYPE: DNA
<213> ORGANISM: Human
<220> FEATURE:
<221> NAME/KEY: misc_feature
<223> OTHER INFORMATION: delta-508 Blocker, Mutant

<400> SEQUENCE: 106
ctatattcat cataggaaac accgatgata ttttctttaa tggtg              45

<210> SEQ ID NO 107
<211> LENGTH: 59
<212> TYPE: DNA
<213> ORGANISM: Human
<220> FEATURE:
<221> NAME/KEY: misc_feature
<223> OTHER INFORMATION: 621+1 Blocker

<400> SEQUENCE: 107
tatgtttagt ttgatttata agaagktaat acttccttgc acaggcccca tggcacata    59

<210> SEQ ID NO 108
<211> LENGTH: 39
<212> TYPE: DNA
<213> ORGANISM: Human
<220> FEATURE:
<221> NAME/KEY: misc_feature
<223> OTHER INFORMATION: 2184delA Blocker, Wild-type

<400> SEQUENCE: 108
gtctgtttaa aagattgttt ttttgtttct gtccaggag                     39

<210> SEQ ID NO 109
<211> LENGTH: 38
<212> TYPE: DNA
<213> ORGANISM: Human
<220> FEATURE:
```

<221> NAME/KEY: misc_feature
<223> OTHER INFORMATION: 2184delA Blocker, Mutant

<400> SEQUENCE: 109
gtctgtttaa aagattgttt tttgtttctg tccaggag                              38

<210> SEQ ID NO 110
<211> LENGTH: 55
<212> TYPE: DNA
<213> ORGANISM: Human
<220> FEATURE:
<221> NAME/KEY: misc_feature
<223> OTHER INFORMATION: 1898+1 Blocker

<400> SEQUENCE: 110
gatgttttaa cagaaaaaga aatatttgaa agrtatgttc tttgaatacc ttact           55

<210> SEQ ID NO 111
<211> LENGTH: 40
<212> TYPE: DNA
<213> ORGANISM: Human
<220> FEATURE:
<221> NAME/KEY: misc_feature
<223> OTHER INFORMATION: N1303K Blocker

<400> SEQUENCE: 111
cactgttcat agggatccaa stttttttcta aatgttccag                           40

<210> SEQ ID NO 112
<211> LENGTH: 45
<212> TYPE: DNA
<213> ORGANISM: Human
<220> FEATURE:
<221> NAME/KEY: misc_feature
<223> OTHER INFORMATION: W1282X Blocker

<400> SEQUENCE: 112
caataacttt gcaacagtgr aggaaagcct ttggagtgat accac                      45

<210> SEQ ID NO 113
<211> LENGTH: 48
<212> TYPE: DNA
<213> ORGANISM: Human
<220> FEATURE:
<221> NAME/KEY: misc_feature
<223> OTHER INFORMATION: 711+1 Blocker

<400> SEQUENCE: 113
gtgcctaaaa gattaaatca ataggtacat amttcatcaa atttgttc                   48

<210> SEQ ID NO 114
<211> LENGTH: 41
<212> TYPE: DNA
<213> ORGANISM: Human
<220> FEATURE:
<221> NAME/KEY: misc_feature
<223> OTHER INFORMATION: R117H Blocker

<400> SEQUENCE: 114
cggataacaa ggaggaacrc tctatcgcga tttatctagg c                          41

<210> SEQ ID NO 115
<211> LENGTH: 44
<212> TYPE: DNA
<213> ORGANISM: Human
<220> FEATURE:
<221> NAME/KEY: misc_feature
<223> OTHER INFORMATION: I148T Blocker

<400> SEQUENCE: 115 gccattttg gccttcatca caytggaatg cagatgagaa tagc                44

<210> SEQ ID NO 116
<211> LENGTH: 44
<212> TYPE: DNA
<213> ORGANISM: Human
<220> FEATURE:
<221> NAME/KEY: misc_feature
<223> OTHER INFORMATION: G85E Blocker

<400> SEQUENCE: 116
ccttacccct aaatataaaa agattycata gaacataaat ctcc                44

<210> SEQ ID NO 117
<211> LENGTH: 46
<212> TYPE: DNA
<213> ORGANISM: Human
<220> FEATURE:
<221> NAME/KEY: misc_feature
<223> OTHER INFORMATION: 1162 Blocker

<400> SEQUENCE: 117
caatgaactt aaagactcrg ctcacagatc gcatctgaaa taaaaa              46

<210> SEQ ID NO 118
<211> LENGTH: 35
<212> TYPE: DNA
<213> ORGANISM: Human
<220> FEATURE:
<221> NAME/KEY: misc_feature
<223> OTHER INFORMATION: 3659delC Blocker, Wild-type

<400> SEQUENCE: 118
gtatggtttg gttgacttgg taggtttacc ttctg                          35

<210> SEQ ID NO 119
<211> LENGTH: 34
<212> TYPE: DNA
<213> ORGANISM: Human
<220> FEATURE:
<221> NAME/KEY: misc_feature
<223> OTHER INFORMATION: 3659delC Blocker, Mutant

<400> SEQUENCE: 119
gtatggtttg gttgacttgt aggtttacct tctg                           34

<210> SEQ ID NO 120
<211> LENGTH: 45
<212> TYPE: DNA
<213> ORGANISM: Human
<220> FEATURE:
<221> NAME/KEY: misc_feature
<223> OTHER INFORMATION: 3120+1 Blocker

<400> SEQUENCE: 120
cggtacttat ttttacatay ctggatgaag tcaaatatgg taaga               45

<210> SEQ ID NO 121
<211> LENGTH: 53
<212> TYPE: DNA
<213> ORGANISM: Human
<220> FEATURE:
<221> NAME/KEY: misc_feature
<223> OTHER INFORMATION: 2789+5 Blocker

<400> SEQUENCE: 121
gtgctgtggc tccttggaaa gtgartattc catgtcctat tgtgtagatt gtg    53

<210> SEQ ID NO 122
<211> LENGTH: 45
<212> TYPE: DNA
<213> ORGANISM: Human
<220> FEATURE:
<221> NAME/KEY: misc_feature
<223> OTHER INFORMATION: A455E Blocker

<400> SEQUENCE: 122
gaggacagtt gttggmggtt gctggatcca ctggagcagg caagg    45

<210> SEQ ID NO 123
<211> LENGTH: 45
<212> TYPE: DNA
<213> ORGANISM: Human
<220> FEATURE:
<221> NAME/KEY: misc_feature
<223> OTHER INFORMATION: R334W Blocker

<400> SEQUENCE: 123
ctaatcaaag gaatcatcct cyggaaaata ttcaccacca tctca    45

<210> SEQ ID NO 124
<211> LENGTH: 45
<212> TYPE: DNA
<213> ORGANISM: Human
<220> FEATURE:
<221> NAME/KEY: misc_feature
<223> OTHER INFORMATION: 1078delT Blocker, Wild-type

<400> SEQUENCE: 124
gctcagcctt cttcttctca gggttctttg tggtgttttt atctg    45

<210> SEQ ID NO 125
<211> LENGTH: 44
<212> TYPE: DNA
<213> ORGANISM: Human
<220> FEATURE:
<221> NAME/KEY: misc_feature
<223> OTHER INFORMATION: 1078delT Blocker, Mutant

<400> SEQUENCE: 125
gctcagcctt cttcttctca gggttcttgt ggtgttttta tctg    44

<210> SEQ ID NO 126
<211> LENGTH: 51
<212> TYPE: DNA
<213> ORGANISM: Human
<220> FEATURE:
<221> NAME/KEY: misc_feature
<223> OTHER INFORMATION: R347P Blocker

<400> SEQUENCE: 126
ttctgcattg ttctgcscat ggcggtcact cggcaatttc cctgggctgt a    51

<210> SEQ ID NO 127
<211> LENGTH: 40
<212> TYPE: DNA
<213> ORGANISM: Human
<220> FEATURE:
<221> NAME/KEY: misc_feature
<223> OTHER INFORMATION: 1717-1 Blocker

<400> SEQUENCE: 127
gagatgtcyt attaccaaaa atagaaaatt agagagtcac　　　　　　　　　　　40

<210> SEQ ID NO 128
<211> LENGTH: 40
<212> TYPE: DNA
<213> ORGANISM: Human
<220> FEATURE:
<221> NAME/KEY: misc_feature
<223> OTHER INFORMATION: G542X Genotyping Blocker

<400> SEQUENCE: 128
actttctcma agaactatat tgtctttctc tgcaaacttg　　　　　　　　　　　40

<210> SEQ ID NO 129
<211> LENGTH: 36
<212> TYPE: DNA
<213> ORGANISM: Human
<220> FEATURE:
<221> NAME/KEY: misc_feature
<223> OTHER INFORMATION: G551D Screening Blocker

<400> SEQUENCE: 129
ttgacctcca ctcagtgtga ttccaccttc tccaac　　　　　　　　　　　　　36

<210> SEQ ID NO 130
<211> LENGTH: 42
<212> TYPE: DNA
<213> ORGANISM: Human
<220> FEATURE:
<221> NAME/KEY: misc_feature
<223> OTHER INFORMATION: G551D/R553X/R560T Blocker

<400> SEQUENCE: 130
tattcacctt gctaaagaaa ttcttgctcg ttgacctcca ct　　　　　　　　　　42

<210> SEQ ID NO 131
<211> LENGTH: 50
<212> TYPE: DNA
<213> ORGANISM: Human
<220> FEATURE:
<221> NAME/KEY: misc_feature
<223> OTHER INFORMATION: G542X/G551D/R553/X Blocker

<400> SEQUENCE: 131
ttgctcgttg acctccactc agtgtgattc caccttctcc aagaactata　　　　　　50

<210> SEQ ID NO 132
<211> LENGTH: 45
<212> TYPE: DNA
<213> ORGANISM: Human
<220> FEATURE:
<221> NAME/KEY: misc_feature
<223> OTHER INFORMATION: R553/X Blocker

<400> SEQUENCE: 132
caataattag ttattcacct tgctaaagaa attcttgctc gttga　　　　　　　　45

<210> SEQ ID NO 133
<211> LENGTH: 35
<212> TYPE: DNA
<213> ORGANISM: Human
<220> FEATURE:

```
<221> NAME/KEY: misc_feature
<223> OTHER INFORMATION: R560T Blocker

<400> SEQUENCE: 133
cttgctagac caataattag ttattcacyt tgcta                                    35
```